US011801295B2

(12) United States Patent
Croyle et al.

(10) Patent No.: US 11,801,295 B2
(45) Date of Patent: *Oct. 31, 2023

(54) IMMUNOGENIC COMPOSITIONS AND USES THEREOF

(71) Applicant: BOARD OF REGENTS, THE UNIVERSITY OF TEXAS SYSTEM, Austin, TX (US)

(72) Inventors: Maria A. Croyle, Austin, TX (US); Stephen Clay Schafer, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 510 days.

This patent is subject to a terminal disclaimer.

(21) Appl. No.: 16/941,481

(22) Filed: Jul. 28, 2020

(65) Prior Publication Data
US 2020/0353068 A1  Nov. 12, 2020

Related U.S. Application Data

(60) Division of application No. 16/392,137, filed on Apr. 23, 2019, now Pat. No. 10,751,409, which is a continuation of application No. 15/907,259, filed on Feb. 27, 2018, now Pat. No. 10,279,029, which is a division of application No. 15/081,601, filed on Mar. 25, 2016, now Pat. No. 9,974,850.

(60) Provisional application No. 62/137,922, filed on Mar. 25, 2015.

(51) Int. Cl.
A61K 39/12 (2006.01)
C12N 7/00 (2006.01)
A61K 39/39 (2006.01)
C12N 15/88 (2006.01)
A61K 39/00 (2006.01)

(52) U.S. Cl.
CPC .............. A61K 39/12 (2013.01); A61K 39/39 (2013.01); C12N 7/00 (2013.01); C12N 15/88 (2013.01); A61K 2039/543 (2013.01); A61K 2039/55555 (2013.01); C12N 2710/10343 (2013.01); C12N 2710/10351 (2013.01); C12N 2710/10371 (2013.01); C12N 2760/14134 (2013.01); C12N 2760/16134 (2013.01)

(58) Field of Classification Search
None
See application file for complete search history.

(56) References Cited

U.S. PATENT DOCUMENTS

| 2,595,793 A | 5/1952 | Kay |
| 4,251,509 A | 2/1981 | Hanson |
| 5,569,468 A | 10/1996 | Modi |
| 5,595,760 A | 1/1997 | Cherif-Cheikh |
| 6,552,024 B1 | 4/2003 | Chen et al. |
| 8,241,661 B1 | 8/2012 | Fuisz et al. |
| 9,974,850 B2 * | 5/2018 | Croyle ............... A61K 39/12 |
| 10,279,029 B2 * | 5/2019 | Croyle ............... A61K 39/12 |
| 10,751,409 B2 * | 8/2020 | Croyle ............... A61K 39/12 |
| 2002/0099001 A1 | 7/2002 | Habberfield |
| 2002/0164353 A1 | 11/2002 | Ertl et al. |
| 2004/0036193 A1 | 2/2004 | Berry et al. |
| 2007/0059807 A1 | 3/2007 | Wisniewski |
| 2007/0104734 A1 | 5/2007 | Oomens et al. |
| 2007/0172653 A1 | 7/2007 | Berland et al. |
| 2009/0092666 A1 | 4/2009 | Brown et al. |
| 2009/0155351 A1 | 6/2009 | Hejl et al. |
| 2010/0209359 A1 | 8/2010 | Foster |
| 2011/0059919 A1 | 3/2011 | Grassauer et al. |
| 2011/0305768 A1 | 12/2011 | Mao et al. |
| 2013/0259945 A1 | 10/2013 | Powell |
| 2014/0120139 A1 | 5/2014 | Croyle et al. |
| 2015/0125495 A1 | 5/2015 | Wood et al. |
| 2016/0296616 A1 | 10/2016 | Croyle et al. |
| 2020/0353068 A1 * | 11/2020 | Croyle ............... A61K 39/39 |

FOREIGN PATENT DOCUMENTS

| CA | 2853894 | 5/2013 |
| WO | WO 2002/101412 | 12/2002 |
| WO | WO 2012/018628 | 2/2012 |
| WO | WO 2018/085495 | 5/2018 |

OTHER PUBLICATIONS

Anatrace™ Specialty Detergents Products P5016-PMAL-C16 (poly (Maleic Anhydride-Alt-1-Octadecene) substituted with 3-(Dimethylamino) Propylamine from https://www.anatrace.com/Products/Specialty-Detergents-Pr0ducts/AMPHIPOL/P5016, accessed July 22, 2017.

Appledorn et al., "Sublingual Administration of an Adenovirus Serotype 5 (Ad5)-Based Vaccine Confirms Toll-Like Receptor Agonist Activity in the Oral Cavity and Elicits Improved Mucosal and Systemic Cell-Mediated Responses against HIV Antigens despite Preexisting Ad5 Immunity", Clin. Vaccine Immunol., 18(1):150-160, 2011.

Di Corato et al., "Water solubilization of hydrophobic nanocrystals by means of poly(maleic anhydride-alt-1-octadecene)," J. Mater. Chem., 18:1991-1996, 2008.

Gorzelle et al., "Amphipols can support the activity of a membrane enzyme," J. Am. Chem. Soc., 124:11594-11595, 2002.

Jonsson-Schmunk and Croyle, "A long-lasting, single dose nasal vaccine for Ebola: a practical armament for an outbreak with significant global impact", Expert Rev. Anti. Infect. Ther., 13(5):527-530, 2015.

Kerwin, "Polysorbates 20 and 80 Used in the Formulation of Protein Biotherapeutics: Structure and Degradation Pathways", J. Pharm. Sci., 97(8):2924-2935, 2008.

(Continued)

Primary Examiner — Shanon A. Foley
(74) Attorney, Agent, or Firm — Parker Highlander PLLC

(57) ABSTRACT

Immunogenic compositions comprising viral vectors and surfactants are provided. Methods for administration and preparation of such compositions are also provided.

20 Claims, 29 Drawing Sheets
(17 of 29 Drawing Sheet(s) Filed in Color)
Specification includes a Sequence Listing.

(56) References Cited

OTHER PUBLICATIONS

Popot et al., "Amphipols from A to Z," *Ann. Rev. Biophys.*, 40:379-408, 2011.
Rehermann et al., "The cytotoxic T lymphocyte response to multiple hepatitis B virus polymerase epitopes during and after acute viral hepatitis," *J. Exp. Med.*, 181:1047-1058, 1995.
Sigma-Aldrich, "Detergent Properties and Applications," retrieved from <URL=https://web.archive.org/web/20160222144312/https://www.sigmaaldrich.com/technical-documents/articles/biofiles/detergent-properties.html> on Mar. 22, 2018, published online on Feb. 22, 2016.
Voros et al., "Immunogenic compositions and uses thereof," *J. Virol.*, 88(5):2584-2594, 2014.
Wikipedia, "Immunogenicity," retrieved from <URL=https://en.wikipedia.org/w/index.php?title=Immunogenicity&oldid=710810712> on Mar. 22, 2018, published online on Mar. 19, 2016.
Wikipedia, "Receptor (biochemistry)," retrieved from <URL=https://en.wikipedia.org/w/index.php?title=Receptor_(biochemistry)&oldid=723830874> on Mar. 23, 2018, published online on Jun. 5, 2016.

\* cited by examiner

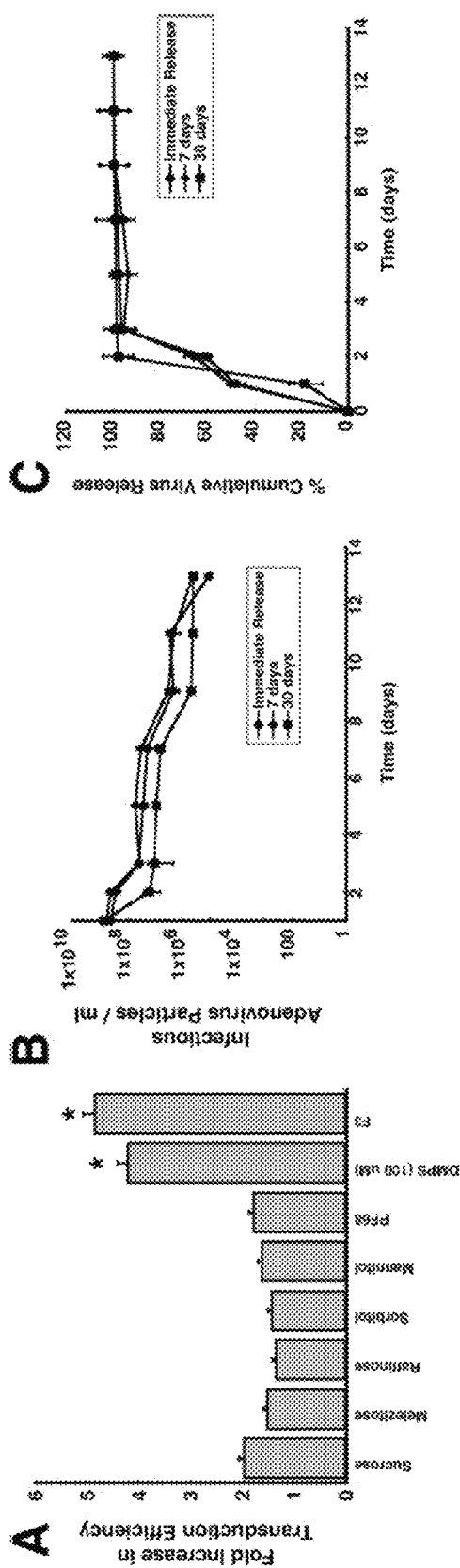
FIG. 1A
FIG. 1B
FIG. 1C
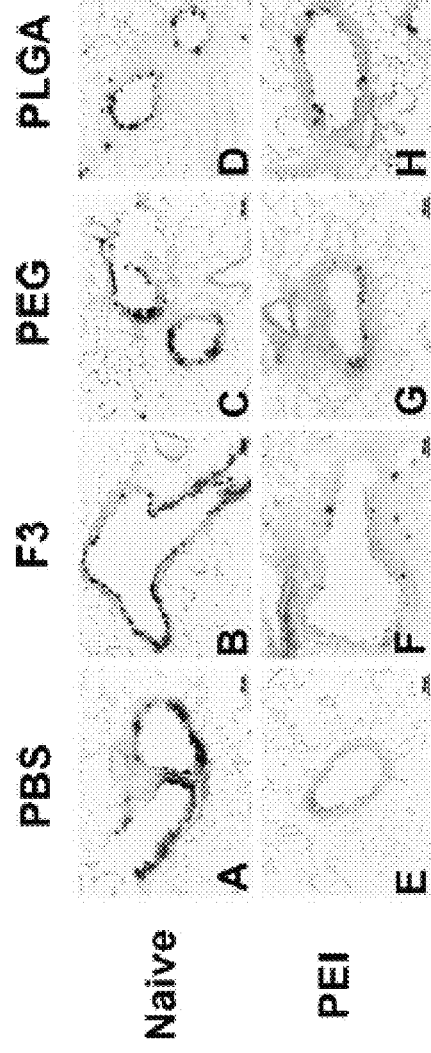
FIGS. 2A-2H

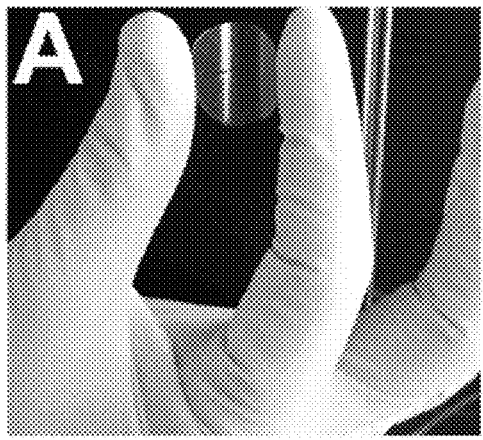
FIG. 23A  FIG. 23B
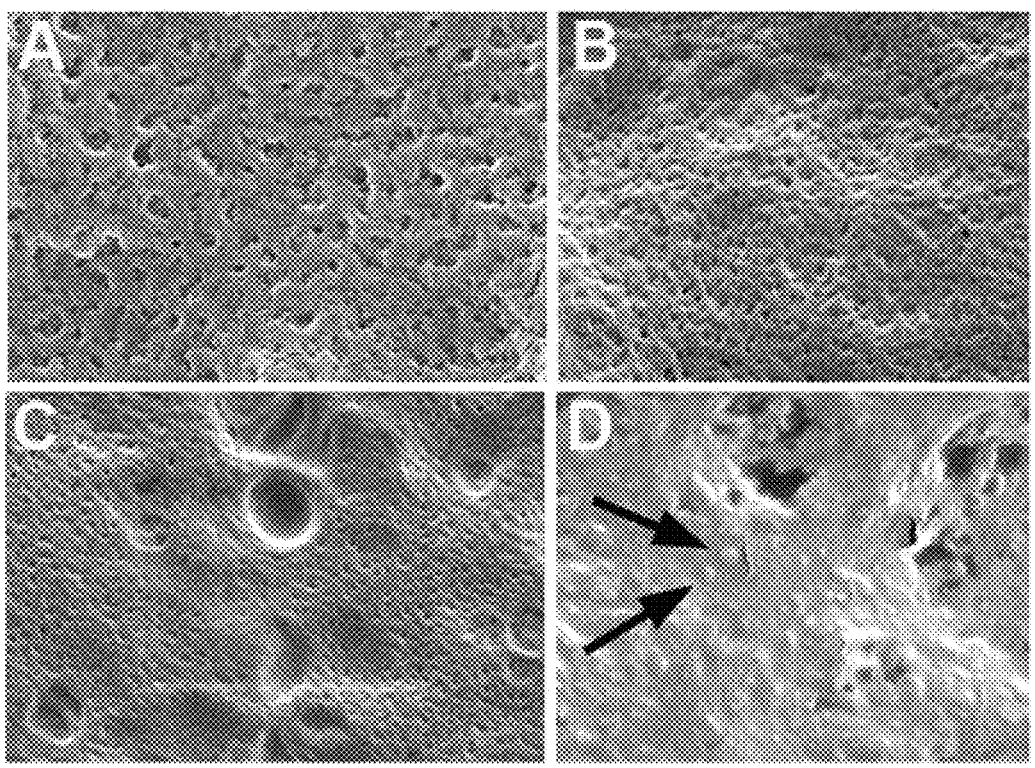
FIGS. 24A-24D

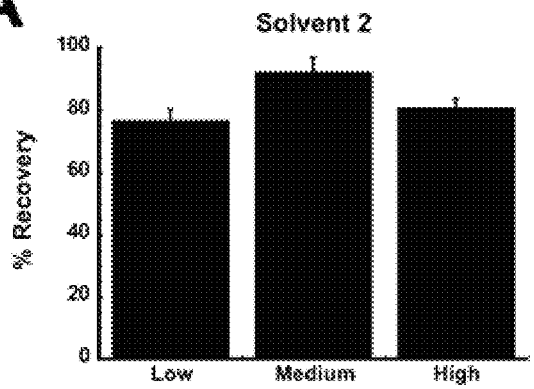
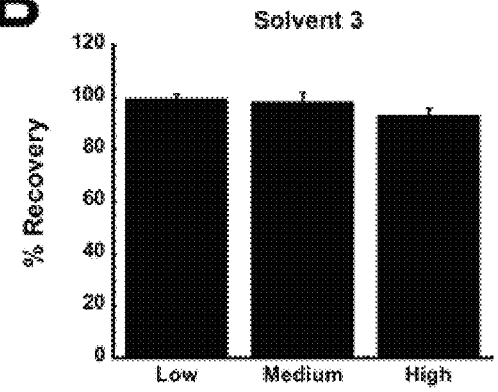
FIG. 31A                FIG. 31B
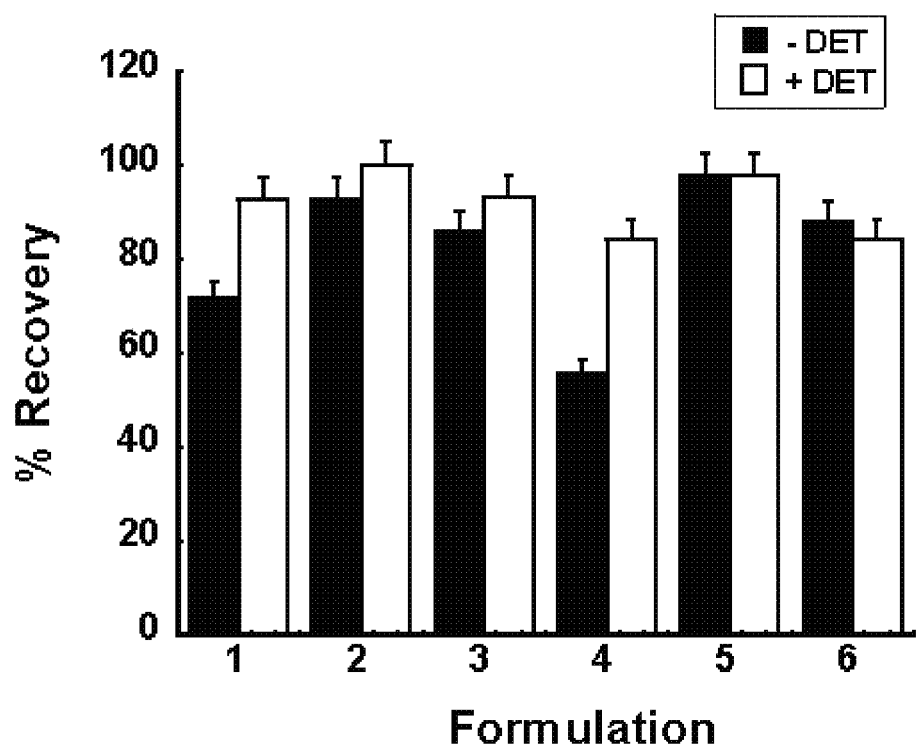
FIG. 32

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Thr Glu Leu Arg Thr Phe Ser Ile
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Tyr Pro Tyr Asp Val Pro Asp Tyr Ala
1               5

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
cagccagcaa tttcttccat                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
tttcggttgc tgtttctgtg                                              20
```

```
<210> SEQ ID NO 5
<211> LENGTH: 24
<212> TYPE: DNA
<213> ORGANISM: Artificial sequence
<220> FEATURE:
<223> OTHER INFORMATION: Synthetic primer

<400> SEQUENCE: 5
atcattggcg tactggagga gcag                                          24

<210> SEQ ID NO 6
<211> LENGTH: 25
<212> TYPE: DNA
<213> ORGANISM: Artificial sequence
<220> FEATURE:
<223> OTHER INFORMATION: Synthetic primer

<400> SEQUENCE: 6
actatatgga caacgtcaac ccatt                                         25

<210> SEQ ID NO 7
<211> LENGTH: 22
<212> TYPE: DNA
<213> ORGANISM: Artificial sequence
<220> FEATURE:
<223> OTHER INFORMATION: Synthetic primer

<400> SEQUENCE: 7
accttctgag gcacctggat gt                                            22

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
accaccgcaa tgctggcctg c                                             21
```

IMMUNOGENIC COMPOSITIONS AND USES THEREOF

CROSS-REFERENCE TO RELATED APPLICATIONS

This application is a division of U.S. patent application Ser. No. 16/392,137, filed Apr. 23, 2019, which is a continuation of U.S. patent application Ser. No. 15/907,259, filed Feb. 27, 2018, now U.S. Pat. No. 10,279,029, which is a division of U.S. patent application Ser. No. 15/081,601, filed Mar. 25, 2016, now U.S. Pat. No. 9,974,850, which claims the benefit of U.S. Provisional Patent Application No. 62/137,922, filed Mar. 25, 2015, the entirety of each of which is incorporated herein by reference. This application is also related to U.S. patent application Ser. No. 13/750,774, filed Jan. 25, 2013, the entirety of which is incorporated herein by reference.

STATEMENT OF GOVERNMENT INTEREST

This invention was made with government support under Grant no. U01 AI078045 awarded by National Institutes of Health, NIAID. The government has certain rights in the invention.

INCORPORATION OF SEQUENCE LISTING

The sequence listing that is contained in the file named "UTSBP1053USD2_ST25.txt", which is 2 KB (as measured in Microsoft Windows®) and was created on Jul. 26, 2020, is filed herewith by electronic submission and is incorporated by reference herein.

BACKGROUND

Vaccination has increased the average human lifespan worldwide more than 10 years during the 20th century. Breakthroughs in immunology, molecular biology and biochemistry in the last 25 years produced more than half of the vaccines used during the last 100 years. Despite this, little progress has been made in delivery since most are injectable and require strict maintenance of cold chain conditions.

Injectable vaccines have various drawbacks. Injections are the most common reason for iatrogenic pain in childhood and deter many from immunization. Injectable vaccines pose a significant risk to the safety of medical staff, patients and community. And most vaccines are unstable at ambient temperatures and require refrigeration.

SUMMARY

In a first embodiment, there is provided an immunogenic composition comprising a recombinant virus vector (e.g., a recombinant virus vector comprising an expression cassette encoding a heterologous antigen), said recombinant virus vector formulated in a pharmaceutically acceptable carrier comprising: (i) PMAL-C16 or (ii) from about 0.1% to 10% of a zwitterionic surfactant. In some aspects, the pharmaceutically acceptable carrier comprises PMAL-C16, such as about 0.1 to 50 mg/ml, 1 to 40 mg/ml, 1 to 30 mg/ml, 1 to 20 mg/ml, or 5 to 15 mg/ml (e.g., about 10 mg/ml) of PMAL-C16. In further aspects, the pharmaceutically acceptable carrier comprises about 0.1% to 10%, 0.5% to 10%, 0.5% to 5%, 1% to 10%, or 1% to 5% of PMAL-C16. In further aspects, the carrier comprises from about 0.1% to 10%, 0.5% to 10%, 0.5% to 5%, 1% to 10%, or 1% to 5% of a zwitterionic surfactant. In particular aspects, the zwitterionic surfactant has a lipid group having a carbon chain of 13-30 carbon atoms. In further aspects, the carrier also comprises a pH buffering agent (e.g., phosphate buffered saline). In certain aspects, the carrier has a pH of between 5.0 and 8.0, between 5.5 and 8.0, between 6.0 and 8.0, between 6.0 and 7.5 or between 6.1 and 7.4. In still a further aspect, the pharmaceutically acceptable carrier comprises a liquid and comprises between about $1\times10^5$ and $1\times10^{13}$, $1\times10^6$ and $1\times10^{13}$, $1\times10^7$ and $1\times10^{13}$, $1\times10^7$ and $1\times10^{12}$, $1\times10^8$ and $1\times10^{12}$, $1\times10^9$ and $1\times10^{12}$, or $1\times10^{10}$ and $1\times10^{13}$ infectious virus particles (e.g., of adenovirus) per ml. In yet further aspects, a composition of the embodiments is defined as able to retain at least about 10%, 50%, 70%, 80%, 90% or 95% (e.g., 80-95%) of the starting concentration of infectious virus after storage at room temperature for 2 months, 4 months, 6 months or 8 months.

In a further embodiment there is provided an immunogenic composition comprising a recombinant virus vector (e.g., a recombinant virus vector comprising an expression cassette encoding a heterologous antigen), said recombinant virus vector formulated in a substantially solid carrier comprising: (i) PMAL-C16 or (ii) from about 0.1% to 10% of a zwitterionic surfactant. In some aspects, the substantially solid carrier comprises less than about 10%, 5%, 4%, 3%, 2%, 1%, 0.5% or 0.1% water. In certain aspects, the substantially solid carrier comprises PMAL-C16, such as about 0.1 to 50 mg/ml, 1 to 40 mg/ml, 1 to 30 mg/ml, 1 to 20 mg/ml, or 5 to 15 mg/ml (e.g., about 10 mg/ml) of PMAL-C16. In further aspects, the substantially solid carrier comprises about 0.1% to 10%, 0.5% to 10%, 0.5% to 5%, 1% to 10%, or 1% to 5% of PMAL-C16. In further aspects, the substantially solid carrier comprises from about 0.1% to 10%, 0.5% to 10%, 0.5% to 5%, 1% to 10%, or 1% to 5% of a zwitterionic surfactant. In particular aspects, the zwitterionic surfactant has a lipid group having a carbon chain of 13-30 carbon atoms. In further aspects, the carrier also comprises a pH buffering agent (e.g., phosphate buffered saline). In certain aspects, the carrier has a pH of between 5.0 and 8.0, between 5.5 and 8.0, between 6.0 and 8.0, between 6.0 and 7.5 or between 6.1 and 7.4. In still a further aspect, the substantially solid carrier comprises a thin film and comprises a between about $1\times10^5$ and $1\times10^{13}$, $1\times10^6$ and $1\times10^{13}$, $1\times10^7$ and $1\times10^{12}$, $1\times10^7$ and $1\times10^{12}$, $1\times10^8$ and $1\times10^{12}$, $1\times10^9$ and $1\times10^{12}$, or $1\times10^{10}$ and $1\times10^{13}$ infectious virus particles (e.g., of adenovirus) per $cm^3$. In yet further aspects, a composition of the embodiments is defined as able to retain at least about 10%, 50%, 70%, 80%, 90% or 95% (e.g., 80-95%) of the starting concentration of infectious virus after storage at room temperature for 6 months, 12 months, 24 months or 36 months.

In still aspects, a composition of the embodiments further comprises a stabilizing agent, such as a sugar, a polymer, amino acids, such as glycine and lysine, or a lyoprotectant. In further aspects, the stabilizing agent comprises a carbohydrate stabilizing agent. For example, the stabilizing agent can comprise dextrose, mannose, galactose, fructose, lactose, sucrose, maltose, sorbitol, mannitol, pluronic F68, melezitose or mixture thereof.

In some aspects, the recombinant virus vector is a non-enveloped virus, such as a non-enveloped DNA virus. In further aspects, the recombinant virus vector is an adenovirus vector, such as a vector comprising a E1/E3 deletion. In particular aspects, the adenovirus vector is an adenovirus 5 vector. In yet further aspects the virus is an enveloped virus (e.g. influenza virus).

A heterologous antigen according to the embodiments can be any of variety of antigens, including but not limited to, a cancer cell antigen or an infectious disease antigen, such as a viral, bacterial or parasite antigen. In certain aspects, the heterologous antigen is a heterologous viral polypeptide, such as a viral envelope polypeptide. For example, the heterologous antigen may be an Ebola virus polypeptide, such as the Ebola virus glycoprotein. In some further aspects, the expression cassette encodes a heterologous antigen, which has been codon optimized for expression in mammalian (e.g., human) cells. Additional exemplary antigens for use according to the embodiments are detailed below.

In a further specific embodiment there is provided an immunogenic composition comprising a recombinant adenovirus vector comprising an expression cassette encoding a heterologous antigen, said recombinant virus vector formulated in a substantially solid carrier comprising from about 0.1% to 10% of a zwitterionic surfactant, said zwitterionic surfactant having a lipid group with a carbon chain of 13-30 carbon atoms. In a particular aspect, the antigen is an Ebola virus glycoprotein.

In yet a further embodiment, there is provided a method for providing an immune response in a mammal comprising obtaining a composition in accordance with the embodiments and aspects described above, which has been dispersed in a pharmaceutically acceptable liquid, and administering an effective amount of the dispersed composition to a mammal. In certain aspects, such a method comprises obtaining a composition in a substantially solid carrier and dispersing the composition in a pharmaceutically acceptable liquid (e.g., water). In some aspects, the administering comprises administering the dispersed composition to a mucosal tissue of the mammal. In certain aspects, the administering is by oral, sublingual, buccal or intranasal administration. In particular aspects, the pharmaceutically acceptable liquid is water or saline solution. In certain aspects, obtaining the composition comprises solubilizing the solid composition in an aqueous liquid such as by contacting the solid with the aqueous liquid and incubating the solid and aqueous liquid for certain period of time, e.g., 1 to 15 minutes.

In yet a further embodiment there is provided a method for providing an immune response in a mammal comprising obtaining a composition a recombinant virus vector (e.g., an adenovirus vector) in a pharmaceutically acceptable carrier, said carrier comprising: (i) PMAL-C16 or (ii) from about 0.1% to 10% of a zwitterionic surfactant, and administering an effective amount to the composition to a subject, wherein the subject has been previously exposed to a virus that cross reacts antigenically with the virus vector of the composition. Thus, in some cases, a subject for treatment according to the embodiments comprises antibodies (e.g., neutralizing antibodies) that bind to the recombinant virus vector. In certain specific aspects, the virus vector is an adenovirus 5 vector and the subject has been previously exposed to adenovirus 5. In further aspects, the virus (e.g., virus vector) of the composition is an influenza virus and the subject has been previously exposed to influenza virus. In a further embodiment there is provided a method for protecting a viral vector from a pre-existing immune response in a subject comprising formulating the viral vector with an effective amount of a zwitterionic surfactant (e.g., PMAL-C16) and administering the formulated viral vector to the subject.

In yet still a further embodiment there is provided a method of making a stabilized immunogenic composition comprising formulating a solution comprising a recombinant virus vector (e.g., an adenovirus vector) in a pharmaceutically acceptable carrier, said carrier comprising: (i) PMAL-C16 or (ii) from about 0.1% to 10% of a zwitterionic surfactant, and then drying the solution to provide a stabilized immunogenic composition. In certain aspects, drying the solution comprises dispersing the solution in a thin film and allowing the liquid to evaporate. In further aspects, the method additionally comprises aliquoting an amount of the stabilized immunogenic composition into a container.

In some aspects, prior to drying, the solution comprises about 0.1 to 50 mg/ml, 1 to 40 mg/ml, 1 to 30 mg/ml, 1 to 20 mg/ml, or 1 to 10 mg/ml of the zwitterionic surfactant. In other aspects, prior to drying, the solution comprises about 0.1 to 50 mg/ml, 1 to 40 mg/ml, 1 to 30 mg/ml, 1 to 20 mg/ml, or 1 to 10 mg/ml of PMAL-C16.

The present disclosure generally relates to vaccine compositions that may be administered to a subject via the buccal and/or sublingual mucosa. In some embodiments, the present disclosure also relates to methods for administration and preparation of such vaccine compositions.

In one embodiment, the present disclosure provides a composition comprising an antigen dispersed within an amorphous solid.

In another embodiment, the present disclosure provides a method comprising administering a vaccine composition comprising an antigen dispersed within an amorphous solid to the buccal and/or sublingual mucosa of a subject in an amount effective to induce an immune response to the antigen.

In yet another embodiment, the present disclosure provides a method comprising providing an antigen and a solution comprising a sugar, sugar derivative or a combination thereof; dispersing the antigen within the solution to form a mixture; and allowing the mixture to harden so as to form an amorphous solid.

The features and advantages of the present invention will be apparent to those skilled in the art. While numerous changes may be made by those skilled in the art, such changes are within the spirit of the invention.

BRIEF DESCRIPTION OF THE DRAWINGS

Some specific example embodiments of the disclosure may be understood by referring, in part, to the following description and the accompanying drawings. The patent or application file contains at least one drawing executed in color. Copies of this patent or patent application publication with color drawing(s) will be provided by the Office upon request and payment of the necessary fee.

FIGS. 1A-1C: Multi-Component Formulations Improve Adenovirus Transduction Efficiency and Stabilize Virus in PLGA Microspheres. (1A) Transduction Efficiency of Excipients and Formulations in Differentiated Calu-3 Cells. Cell monolayers were exposed to formulations containing a model recombinant adenovirus serotype 5 vector expressing beta-galactosidase (AdlacZ) for 2 hours at 37° C. Transduction efficiency was determined by comparison of the number of cells expressing the beta-galactosidase transgene after treatment with formulated virus to the number of beta-galactosidase positive cells after treatment with virus in saline. Results are reported as the mean±standard error of the mean of data generated from triplicate samples over three separate experiments (n=9 each formulation). PF68, Pluronic F68; nDMPS, N-dodecyl-β-D-maltopyranoside; F3, formulation containing sucrose (10 mg/ml), mannitol (40 mg/ml) and 1% (v/v) poly(ethylene) glycol 3,000. *indicates a significant difference with respect to unformulated virus (1B) Adenovirus Concentration Versus Time Profiles of Supernatants Collected from PLGA Microspheres Stored at 37° C. Ten milligrams of microspheres containing AdlacZ were suspended in 0.5 ml of sterile saline immediately after preparation (Immediate Release) or after storage at room temperature (25° C.) for 7 or 30 days. The number of infectious particles released at each time point was determined by serial dilution of collected supernatants and subsequent infection of Calu-3 cells. (IC) In Vitro Release Profiles of Adenovirus from PLGA Microspheres Stored at Room Temperature Over Time. Release rates for freshly prepared beads did not significantly differ from those of beads stored at 25° C. for 7 days. The release rate increased threefold after storage for one month under the same conditions. Results depicted in Panels B and C are reported as the mean±standard error of the mean of data generated from triplicate samples collected from six separate experiments.

FIGS. 2A-2H: Formulations Improve Adenovirus Transduction Efficiency in the Lungs of Naïve Mice and Those with Prior Exposure to Adenovirus. Naïve C57BL/6 mice were given $5 \times 10^{10}$ particles of the model recombinant virus used for in vitro screening of formulations (AdlacZ) suspended in potassium phosphate buffered saline (2A), in formulation F3 (2B), PEGylated virus (2C) or 4.6 mg of PLGA microspheres containing the same dose of virus (2D) by the intranasal route. A second set of mice were divided into the same treatment groups 28 days after receiving a dose of $5 \times 10^{10}$ particles of AdNull, an E1/E3 deleted recombinant adenovirus serotype 5 virus similar to the AdlacZ vector which does not contain a transgene cassette (2E-2H). Mice in each group were sacrificed 4 days after administration of the AdlacZ vector. Images display representative gene expression patterns for 6 mice per treatment group. Magnification in each panel: 200×.

FIGS. 23A-23B: Biologicals can be stabilized in small, unit dose films for evaluation of potency and bioavailability of protein based, live virus and bacteria-based vaccines in a variety of animal models and for evaluation of long-term physical stability of vaccines (23A). Several thousand doses of a given biological substance can be stabilized in large films that can be divided into reproducible single-use pieces (23B).

FIGS. 24A-24D: (24A) Porous surface of dried film (3% HPMC/2% sorbitol/0.2% tragacanth gum/PBS) in the absence of virus (Magnification: 75,000×). (24B) Electron micrograph of dried film (1.5% HPMC/2% Sorbitol/0.2% tragacanth gum/PBS) in the absence of virus (Magnification: 25,000×). (24C) Large Non-Crystalline Pockets in Film made of 1.5% HPMC/2% Sorbitol/0.2% tragacanth gum in PBS which Foster Stabilization of Virus Particles in the Amorphous State. (Magnification 20,000×). (24D) Adenovirus Particles (arrows) Suspended in Film. The presence of the virus notably changes the physical characteristics of the film as it assumes a non-porous, amorphous shape. Formulation is same as that in 24C. (Magnification 20,000×).

$$\% \text{ Recovery} = \frac{\log \text{ (Infectious Titer at } t = 1)}{\log \text{ (Infectious Titer at } t = 0)} \times 100$$

Figure 29:
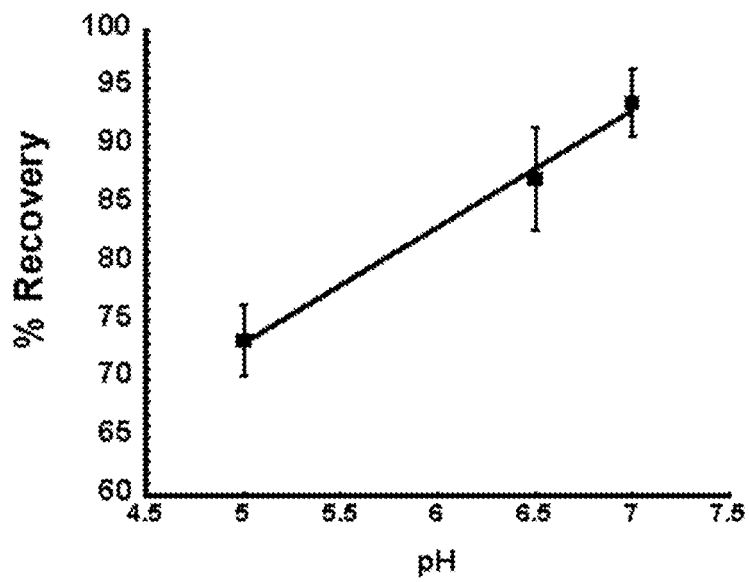

FIG. 29: The pH of the Dried Film Significantly Impacts Recovery of Infectious Virus After Reconstitution. Recombinant adenovirus was placed in a variety of formulations that were dried as thin films. Twenty-four hours later, films were reconstituted and viral titer assessed by a standard limiting dilution assay. Data was grouped according to the final pH of the dried film. (correlation coefficient $r^2$=0.996)

Figure 30:
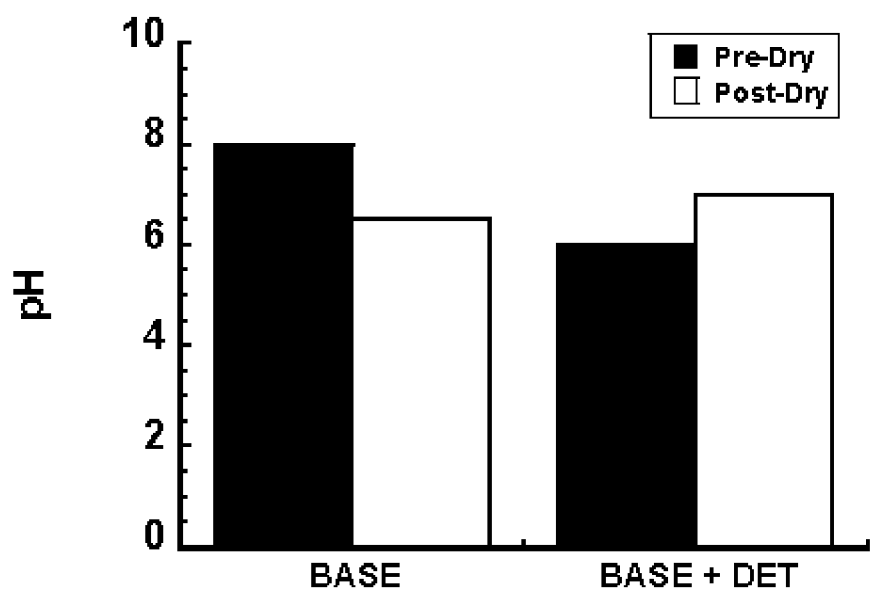

FIG. 30: Detergent Prevents Drop in Film pH After Drying. The pH of formulations consisting of 0.1-15% hydroxypropyl methylcellulose, 0.1-0.8% tragacanth gum, 1-5% sorbitol and 1-100 mg/ml melezitose. without detergent (BASE) and that containing 10 mg/ml PMCAL C16 (BASE+DET) in the liquid (pre-dry) and dry state was recorded according to the method described in Croyle et al. (2001) Gene Ther. 8: 1281-1290. Prior to drying, 10 microliters of Universal pH Indicator Solution (Fisher Scientific) was added to each formulation and the pH visually recorded. When drying was complete, films were visually inspected and the pH compared to pre-drying values.

FIGS. 31A-31B: Formulation Dictates Recovery of Virus from Dried Film in Certain Solvent Systems. Three different concentrations of hydroxypropyl methylcellulose (0.5, 1.5 and 3%) were evaluated for their ability to retain infectious titer of virus after drying in 120 mM PBS (Solvent 2) or 10 mM Tris buffer. Films were dried at ambient temperature and pressure for 6 hours. Twenty four hours later, each film was reconstituted with sterile saline and infectious titer of virus embedded in the preparation determined by serial dilution, infection of HeLa cells and visual tallying of cells staining positive for virus. Percent recovery was calculated using formula provided above.

FIG. 32: Detergent Significantly Improves Recovery of Infectious Virus from Films. Recombinant adenovirus ($1.25\times10^{12}$ particles) was formulated in: (A) 0.5% w/w hydroxypropyl methylcellulose containing 2% w/w sorbitol (Formulation 1) or 2% v/v glycerol (Formulation 2); (B) 1.5% w/w hydroxypropyl methylcellulose containing 2% w/w sorbitol (Formulation 3) or 2% v/v glycerol (Formulation 4); (C) 3% w/w hydroxypropyl methylcellulose containing 2% w/w sorbitol (Formulation 5) or 2% v/v glycerol (Formulation 6) with (+DET) or without (−DET) 10 mg/ml PMAL C16. Formulations were dried into thin films, reconstituted 24 hours after drying and infectious titer determined by limiting dilution on HeLa cells.

FIG. 33: The Amount of Virus Embedded in Film Formulation Does not Impact Recovery. Adenovirus particles were incorporated in thin films in amounts ranging from those found post-purification ($1\times10^{13}$, $1\times10^{12}$ infectious particles) to those which reflect reasonable doses for immunization and therapeutic purposes ($1\times10^{11}$-$1\times10^{7}$ infectious particles). These concentrations did not seem to impact recovery from dried films suggesting that they can be utilized for stabilizing biologicals during holding steps of manufacturing processes as well as for single use films for self therapy/immunization.

FIG. 34: Binding Agents Improve Recovery of Recombinant Virus from Film. Inclusion of a binding agent (in this case 2% w/w sorbitol, Binder) in the film formulation improved recovery of virus by 43% (1.5% HPMC, Base 2) and 21.1% (3% HPMC, Base 3) after drying. Addition of plasticizers (in this case 2% v/v glycerol, Plasticizer) did not improve recovery to the same degree (32.3%, Base 2, 14.1%, Base 3).

FIG. 35: Virus Significantly Impacts the Dissolution Rate of Films in Simulated Saliva. Films of uniform weight containing $1.25\times10^{12}$ particles of recombinant adenovirus (VIRUS) and blank controls were placed in simulated human salivary fluid at 37° C. under gentle stirring. Dissolution rate was calculated by dividing the starting weight of the film by the time at which the film could no longer be visibly detected in the solvent. Simulated human saliva fluid consisted of: KCl 0.15 g/L, NaCl 0.12 g/L, Sodium Bicarbonate 2.1 g/L, alpha-amylase 2.0 g/L and gastric mucin 1.0 g/L as described in Davis et al. (1971) *J. Pharm. Sci.* 60(3):429-432. Formulations included in this study consisted of: (A) 0.5% w/w hydroxypropyl methylcellulose containing 2% w/w sorbitol (Formulation 1) or 2% v/v glycerol (Formulation 2); (B) 1.5% w/w hydroxypropyl methylcellulose containing 2% w/w sorbitol (Formulation 3) or 2% v/v glycerol (Formulation 4); (C) 3% w/w hydroxypropyl methylcellulose containing 2% w/w sorbitol (Formulation 5) or 2% w/v glycerol (Formulation 6).

FIG. 36: PMAL C16 Significantly Improves Dissolution Time for Films. Films of uniform weight were placed in sterile saline at 37° C. under gentle stirring. Dissolution rate was calculated by dividing the starting weight of the film by the time at which the film could no longer be visibly detected in the solvent. Formulations included in this study consisted of: (A) 0.5% w/w hydroxypropyl methylcellulose containing 2% w/w sorbitol (Formulation 1) or 2% v/v glycerol (Formulation 2); (B) 1.5% w/w hydroxypropyl methylcellulose containing 2% w/w sorbitol (Formulation 3) or 2% v/v glycerol (Formulation 4); (C) 3% w/w hydroxypropyl methylcellulose containing 2% w/w sorbitol (Formulation 5) or 2% w/v glycerol (Formulation 6).

FIG. 37: Film Formulations with and without PMAL C16 Protect Adenovirus From Degradation in Saliva. Infectious titer of unformulated virus (Ad Unform.) placed in simulated human salivary fluid for 5 minutes dropped by a factor of 3 when compared to the same concentration of virus incubated in sterile saline (Ad Control). The infectious titer of virus formulated in standard film base (1.5% HPMC, FILM) significantly improved the titer of the virus in simulated human saliva six-fold. The addition of PMAL C16 enhanced protection of the virus from digestive amylase and mucin. The infectious titer of this preparation (FILM+DET) was 22 times that of the unformulated virus (Ad Unform.).

FIG. 38: Virus Significantly Impacts the Moisture Retained in Dried Film Formulations. Moisture content for films of uniform weight containing $1.25\times10^{12}$ particles of recombinant adenovirus (VIRUS) and blank controls was assessed by Karl Fischer titration according to USP standards. Formulations included in this study consisted of: (A) 0.5% w/w hydroxypropyl methylcellulose alone (Formulation 1) or containing 2% w/w sorbitol (Formulation 2) or 2% v/v glycerol (Formulation 3); (B) 1.5% w/w hydroxypropyl methylcellulose alone (Formulation 4) or containing 2% w/w sorbitol (Formulation 5) or 2% v/v glycerol (Formulation 6); (C) 3% w/w hydroxypropyl methylcellulose alone (Formulation 7) containing 2% w/w sorbitol (Formulation 8) or 2% v/v glycerol (Formulation 9).

FIG. 39: PMAL C16 Profoundly Increases Moisture Content of Films Containing Virus. Moisture content for films of uniform weight containing $1.25\times10^{12}$ particles of recombinant adenovirus in base formulation (BASE) and films including detergent (DET) was assessed by Karl Fischer titration according to USP standards. (A) 0.5% w/w hydroxypropyl methylcellulose alone (Formulation 1) or containing 2% w/w sorbitol (Formulation 2) or 2% v/v glycerol (Formulation 3); (B) 1.5% w/w hydroxypropyl methylcellulose alone (Formulation 4) or containing 2% w/w sorbitol (Formulation 5) or 2% v/v glycerol (Formulation 6); (C) 3% w/w hydroxypropyl methylcellulose alone (Formulation 7) containing 2% w/w sorbitol (Formulation 8) or 2% v/v glycerol (Formulation 9)

Figure 40:
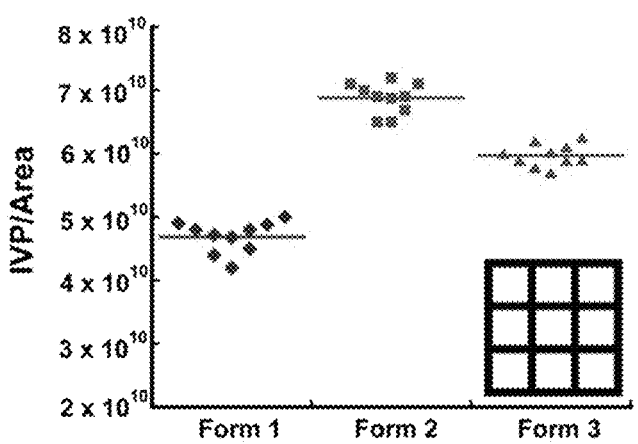

FIG. 40: Recombinant Adenovirus Can Be Evenly Distributed Across Large Film that can be Divided into Equal Unit Doses. A 3 cm×3 cm film containing recombinant adenovirus was dried and divided into nine 1 cm×1 cm parts (black grid, lower right corner of plot). Each part was reconstituted with sterile saline and titer assessed by an in vitro assay. Data shown is representative of 3 different formulations. Formulations included in this study consisted of: 0.5% w/w hydroxypropyl methylcellulose containing 2% w/w sorbitol (Formulation 1), 1.5% w/w hydroxypropyl methylcellulose containing 2% w/w sorbitol (Formulation 2) and 3% w/w hydroxypropyl methylcellulose containing 2% w/v glycerol (Formulation 3). Formulations were prepared in 120 mM PBS.

Figure 41A:
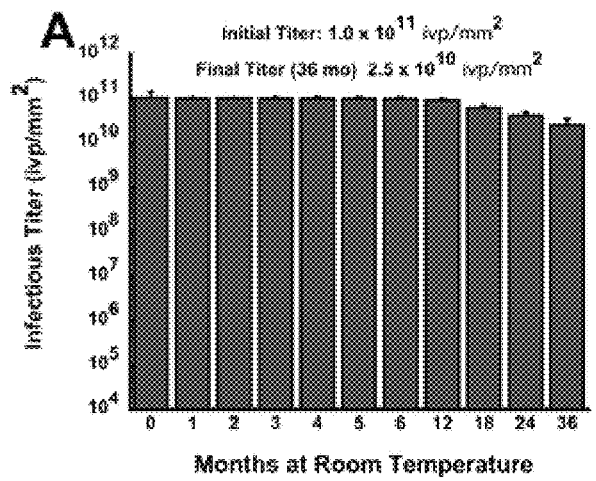
Figure 41B:
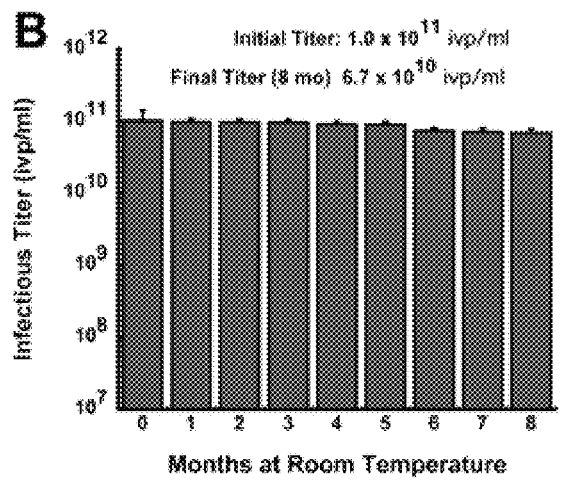
Figure 41C:
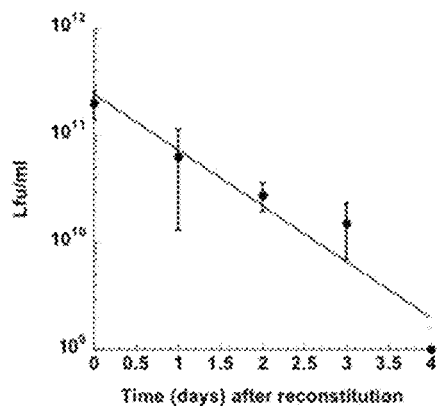

FIGS. 41A-41C: Formulations can significantly extend shelf-life of recombinant adenovirus at ambient temperature in dried and reconstituted films. 41A: 30 month Stability Profile for Ebola Vaccine in Solid Film Matrix. 41B: 8 month Stability Profile of Ebola Vaccine Reconstituted from Film Matrix and Stored in Liquid Form. Each preparation was stored at 20° C. This is markedly better than the stability seen after reconstitution of a stable lyophilized formulation of the virus and subsequent storage at 4° C. (41C).

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to vaccine compositions that may be administered to a subject via the buccal and/or sublingual mucosa. In some embodiments, the present disclosure also relates to methods for administration and preparation of such vaccine compositions.

The buccal and the sublingual mucosa are attractive for the delivery of medicinal compounds and have largely been uninvestigated in the context of protective immunization. The sublingual and the buccal epithelium are highly vascularized, allowing direct entry into the systemic circulation, avoiding pre-systemic metabolism of antigen in the gastrointestinal tract. They harbor a dense lattice of professional antigen presenting cells (APCs), contain many T lymphocytes and directly access mucosal-associated lymphoid tissues. One of the many advantages of the present disclosure, many of which are not discussed herein, is that a vaccine composition of the present disclosure may be administered by direct application to the cheek (buccal) or under the tongue (sublingual), which may then induce a strong protective systemic and mucosal immune response. Furthermore, in those embodiments where the vaccine is a recombinant adenovirus ("Ad")-based vaccine, it may be administered via the buccal and/or sublingual mucosa with significant potential for successful vaccination of those with pre-existing immunity to Ad5. Pre-existing immunity to Ad5 is a global phenomenon and is currently the most significant limitation to the use of these vectors.

The buccal and sublingual mucosa contain an immobile expanse of smooth muscle upon which of a variety of dosage forms such as lozenges, gels, patches and films can reside (Pather, 2008). This supports an epithelium of 40-50 layers of actively dividing squamous, non-keratinized cells (Wertz, 1991). Although this layer is the most significant barrier to the absorption of large molecules though the cheek, cell turnover is slow (4-14 days), allowing for continued release of antigen (Hill, 1984). Reagents that aid absorption of large molecules across the mucosa (surfactants, cyclodextrins, polyacrlyates) and polymers that facilitate interaction with the surface (polycarbophil, carboxymethyl cellulose) also protect labile molecules from degradation at ambient temperatures (Hassan, 2010; Shojaci, 1998). Accordingly, the present disclosure is also innovative in that it promotes a delivery method that could improve vaccine potency and physical stability at ambient temperatures.

In some embodiments, the present disclosure provides a vaccine composition comprising an antigen dispersed within an amorphous solid. As used herein, the term "antigen" means a substance that induces a specific immune response in a host animal. The antigen may comprise a whole organism, killed, attenuated or live (including killed, attenuated or inactivated bacteria, viruses, fungi, parasites, prions or other microbes); a subunit or portion of an organism; a recombinant vector containing an insert with immunogenic properties; a piece or fragment of DNA capable of inducing an immune response upon presentation to a host animal or which contains the genetic material that allows expression of a given antigen in cells that take up the DNA; a protein, a polypeptide, a peptide, an epitope, a hapten, or any combination thereof. Alternatively, the antigen may comprise a toxin or antitoxin.

In general, an amorphous solid suitable for use in the present disclosure should be dissolvable upon contact with an aqueous liquid, such as saliva. In some embodiments, amorphous solids suitable for use in the present disclosure may be formed from any sugar, sugar derivative or combination of sugars/derivatives so long as the sugar and/or derivative is prepared as a liquid solution at a concentration that allows it to flow freely when poured but also forms an amorphous phase at ambient temperatures on a physical surface that facilitates this process, such as aluminum or Teflon. Examples of suitable sugars may include, but are not limited to glucose, dextrose, fructose, lactose, maltose, xylose, sucrose, corn sugar syrup, sorbitol, hexitol, maltilol, xylitol, mannitol, melezitose, raffinose, and a combination thereof. While not being bound to any particular theory, it is believed that sugars minimize interaction of the antigen with water during storage and drying, in turn, preventing damage to the three dimensional shape of the antigen due to crystal formation during the drying process and subsequent loss of efficacy. An example of the surface characteristics of an amorphous solid is illustrated in FIGS. 23A and 24D. In some embodiments, an amorphous solid suitable for use in the present disclosure may have a thickness of about 0.05 micrometers to about 5 millimeters.

In addition, in some embodiments, certain sugars may also function as a binder which may provide "substance" to pharmaceutical preparations that contain small quantities of very potent medications for ease of handling/administration. They may also hold components together or promote binding to surfaces (like the film backing) to ease drug delivery and handling. Lastly, they may also contribute to the overall pharmaceutical elegance of a preparation by forming uniform glasses upon drying.

In certain embodiments, the vaccine compositions of the present disclosure also may comprise a water-soluble polymer including, but not limited to, carboxymethyl cellulose, carboxyvinyl polymers, high amylose starch, hydroxyethyl cellulose, hydroxypropyl cellulose, hydroxypropyl methylcellulose, methylmethacrylate copolymers, polyacrylic acid, polyvinyl alcohol, polyvinyl pyrrolidone, pullulan, sodium alginate, poly(lactic-co-glycolic acid), poly(ethylene) oxide, poly(hydroxyalkanoate) and a combination thereof.

Furthermore, in some embodiments, the vaccine compositions of the present disclosure may further comprise one or more oils, polyalcohols, surfactants, permeability enhancers, and/or edible organic acids. Examples of suitable oils may include, but are not limited to, eucalyptol, menthol, vacrol, thymol, methyl salicylate, verbenone, eugenol, gerianol and a combination thereof. Examples of suitable polyalcohols may include, but are not limited to, glycerol, polyethylene glycol, propylene glycol, and a combination thereof. Examples of suitable edible organic acids may include, but are not limited to, citric acid, malic acid, tartaric acid, fumaric acid, phosphoric acid, oxalic acid, ascorbic acid and a combination thereof. Examples of suitable surfactants may include, but are not limited to, difunctional block copolymer surfactants terminating in primary hydroxyl groups, such as Pluronic® F68 commercially available from BASF, poly(ethylene) glycol 3000, dodecyl-β-D-maltopyranoside, disodium PEG-4 cocamido MIPA-sulfosuccinate ("DMPS"), etc. It is believed that certain surfactants may minimize interaction of the antigen with itself and other antigens and subsequent formation of large aggregated particles that cannot effectively enter and be processed by target and antigen presenting cells. They may also be capable of weakening cell membranes without causing permanent damage and, through this mechanism, promote uptake of large particles though rugged biological membranes such as the buccal mucosa.

In certain preferred aspects, an immunogenic composition of the embodiments comprises a zwitterionic surfactant. In some embodiments, the zwitterionic surfactant is a surfactant molecule which contains a group which is capable of being positively charged and a group which is capable of being negatively charged. In some embodiments, both the positively charged and negatively charged groups are ionized at physiological pH such that the molecule has a net neutral charge. In some embodiments, the positively charged group comprises a protonated or quaternary ammonium. In some embodiments, the negatively charged group comprises a sulfate, a phosphate, or a carboxylate. The zwitterionic surfactant further comprises one or more lipid groups consisting essentially of an alkyl, cycloalkyl, or alkenyl groups. Preferably, the zwitterionic surfactant comprises one or more lipid groups consisting essentially of an alkyl, cycloalkyl, or alkenyl groups with a carbon chain of more than 12 carbon atoms. In some embodiments, the lipid group has a carbon chain of 12-30 carbon atoms. In some embodiments, the lipid group has a carbon chain of 12-24 carbon atoms. In some embodiments, the lipid group has from 12, 13, 14, 15, 16, 17, 18, 19, 20, 21, 22, 23, to 24 carbons, or any range derivable thereof. In some embodiments, the zwitterionic surfactant is a polymeric structure which contains multiple zwitterionic groups and multiple lipid groups on a central backbone. In some embodiments, the zwitterionic surfactant is a polymer which has from about 50 to about 200 repeating units wherein each repeating units comprises one positively charged group, one negatively charged group, and one lipid group. In some embodiments, the zwitterionic surfactant is a polymer which has a 75 to 150 repeating units. In some embodiments, the central backbone is an alkyl, polyethylene glycol, or polypropylene chain. In some embodiments, the central chain is an alkyl group.

Some non-limiting examples of zwitterionic surfactants include 3-(N,N-Dimethyltetradecylammonio)propanesulfonate (SB3-14), 3-(4-Heptyl)phenyl-3-hydroxypropyl) dimethylammoniopropanesulfonate (C7BzO), 3-(decyldimethylammonio) propanesulfonate inner salt (SB3-10), 3-(dodecyldimethylammonio) propanesulfonate inner salt (SB3-12), 3-(N,N-dimethyloctadecylammonio) propanesulfonate (SB3-18), 3-(N,N-dimethyl-octylammonio) propanesulfonate inner salt (SB3-8), 3-(N,N-dimethylpalmitylammonio) propanesulfonate (SB3-16), 3-[N,N-dimethyl(3-myristoylaminopropyl)ammonio]propane-sulfonate (ASB-14), CHAPS, CHAPSO, acetylated lecithin, alkyl(C12-30) dialkylamine-N-oxide apricotamidopropyl betaine, babassuamidopropyl betaine, behenyl betaine, bis 2-hydroxyethyl tallow glycinate, C12-14 alkyl dimethyl betaine, canolamidopropyl betaine, capric/caprylic amidopropyl betaine, capryloamidopropyl betaine, cetyl betaine, 3-[(Cocamidoethyl)dimethylammonio]-2-hydroxypropanesulfonate, 3-[(Cocamidoethyl)dimethyl-ammonio]propanesulfonate, cocamidopropyl betaine, cocamidopropyl dimethylaminohydroxypropyl hydrolyzed collagen, N-[3-cocamido)-propyl]-N,N-dimethyl betaine, potassium salt, cocamidopropyl hydroxysultaine, cocamidopropyl sulfobetaine, cocaminobutyric acid, cocaminopropionic acid, cocoamphodipropionic acid, coco-betaine, cocodimethylammonium-3-sulfopropylbetaine, cocoiminodiglycinate, cocoiminodipropionate, coco/oleamidopropyl betaine, cocoyl sarcosinamide DEA, DEA-cocoamphodipropionate, dihydroxyethyl tallow glycinate, dimethicone propyl PG-betaine, N,N-dimethyl-N-lauric acid-amidopropyl-N-(3-sulfopropyl)-ammonium betaine, N,N-dimethyl-N-myristyl-N-(3-sulfopropyl)-ammonium betaine, N,N-dimethyl-N-palmityl-N-(3-sulfopropyl)-ammonium betaine, N,N-dimethyl-N-stearamidopropyl-N-(3-sulfopropyl)-ammonium betaine, N,N-dimethyl-N-stearyl-N-(3-sulfopropyl)-ammonium betaine, N,N-dimethyl-N-tallow-N-(3-sulfopropyl)-ammonium betaine, disodium caproamphodiacetate, disodium caproamphodipropionate, disodium capryloamphodiacetate, disodium capryloamphodipropionate, disodium cocoamphodiacetate, disodium cocoamphodipropionate, disodium isostearoamphodipropionate, disodium laureth-5 carboxyamphodiacetate, disodium lauriminodipropionate, disodium lauroamphodiacetate, disodium lauroamphodipropionate, disodium octyl b-iminodipropionate, disodium oleoamphodiacetate, disodium oleoamphodipropionate, disodium PPG-2-isodeceth-7 carboxyamphodiacetate, disodium soyamphodiacetate, disodium stearoamphodiacetate, disodium tallamphodipropionate, disodium tallowamphodiacetate, disodium tallowiminodipropionate, disodium wheatgermamphodiacetate, N,N-distearyl-N-methyl-N-(3-sulfopropyl)-ammonium betaine, erucamidopropyl hydroxysultaine, ethylhexyl dipropionate, ethyl hydroxymethyl oleyl oxazoline, ethyl PEG-15 cocamine sulfate, hydrogenated lecithin, hydrolyzed protein, isostearamidopropyl betaine, 3-[(Lauramidoethyl)dimethylammonio]-2-hydroxypropanesulfonate, 3-[(Lauramidoethyl)dimethylammonio]propanesulfonate, lauramidopropyl betaine, lauramidopropyl dimethyl betaine, lauraminopropionic acid, lauroamphodipropionic acid, lauroyl lysine, lauryl betaine, lauryl hydroxysultaine, lauryl sultaine, linoleamidopropyl betaine, lysolecithin, milk lipid amidopropyl betaine, myristamidopropyl betaine, octyl dipropionate, octyliminodipropionate, n-octyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propane-sulfonate, n-tetradecyl-N,N-dimethyl-3-ammonio-1-propanesulfonate, n-hexadecyl-N,N-dimethyl-3-ammonio-1-propanesulfonate, n-octadecyl-N,N-dimethyl-3-ammonio-1-propane-sulfonate, oleamidopropyl betaine, oleyl betaine, 4,4(5H)-oxazoledimethanol, 2-(heptadecenyl) betaine, palmitamidopropyl betaine, palmitamine oxide, PMAL-C6, PMAL-C12, PMAL-C16, ricinoleamidopropyl betaine, ricinoleamidopropyl betaine/IPDI copolymer, sesamidopropyl betaine, sodium C12-15 alkoxypropyl iminodipropionate, sodium caproamphoacetate, sodium capryloamphoacetate, sodium capryloamphohydroxypropyl sulfonate, sodium capryloamphopropionate, sodium carboxymethyl tallow polypropylamine, sodium cocaminopropionate, sodium cocoamphoacetate, sodium cocoamphohydroxypropyl sulfonate, sodium cocoamphopropionate, sodium dicarboxyethyl cocophosphoethyl imidazoline, sodium hydrogenated tallow dimethyl glycinate, sodium isostearoamphopropionate, sodium lauriminodipropionate, sodium lauroamphoacetate, sodium oleoamphohydroxypropylsulfonate, sodium oleoamphopropionate, sodium stearoamphoacetate, sodium tallamphopropionate, soyamidopropyl betaine, stearyl betaine, 3-[(Stearamidoethyl)dimethylammonio]-2-hydroxypropanesulfonate, 3-[(Stearamidoethyl)-dimethylammonio] propanesulfonate, tallowamidopropyl hydroxysultaine, tallowamphopoly-carboxypropionic acid, trisodium lauroampho PG-acetate phosphate chloride, undecylenamidopropyl betaine, and wheat germamidopropyl betaine.

A vaccine composition of the present disclosure further comprises an antigen. Antigens suitable for use in the present disclosure may include any antigen for which cellular and/or humoral immune responses are desired, including antigens derived from viral, bacterial, fungal and parasitic pathogens and prions that may induce antibodies, T-cell helper epitopes and T-cell cytotoxic epitopes. Such antigens include, but are not limited to, those encoded by human and animal viruses and can correspond to either structural or non-structural proteins. Furthermore, the present disclosure contemplates vaccines made using antigens derived from any of the antigen sources discussed below and those that use these sources as potential delivery devices or vectors. For example, in one specific embodiment, recombinant adenovirus may be used to deliver Ebola antigens for immunization against Ebola infection.

Antigens useful in the present disclosure may include those derived from viruses including, but not limited to, those from the family Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus), Flaviviridae (e.g., Yellow fever virus group. Hepatitis C virus), Hepadnaviridae (e.g., Hepatitis B virus). Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus). Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus. Cardiovirus such as Encephalomyocarditis virus, Aphthovirus such as Foot-and-mouth disease virus O, Coxsackie virus), Poxyiridae (e.g., Orthopoxvirus such as Variola virus or monkey poxvirus), Reoviridae (e.g., Rotavirus such as Groups A-F rotaviruses), Retroviridae (Primate lentivirus group such as human immunodeficiency virus 1 and 2). Rhabdoviridae (e.g., rabies virus), Togaviridae (e.g., Rubivirus such as Rubella virus), Human T-cell leukemia virus, Murine leukemia virus, Vesicular stomatitis virus, Wart virus, Blue tongue virus, Sendai virus, Feline leukemia virus, Simian virus 40, Mouse mammary tumor virus. Dengue virus, HIV-1 and HIV-2. West Nile, H1N1, SARS, 1918 Influenza, Tick-borne encephalitis virus complex (Absettarov, Hanzalova, Hypr), Russian Spring-Summer encephalitis virus, Congo-Crimean Hemorrhagic Fever virus. Junin Virus, Kumlinge Virus, Marburg Virus, Machupo Virus, Kyasanur Forest Disease Virus, Lassa Virus, Omsk Hemorrhagic Fever Virus, FIV, SIV, Herpes simplex 1 and 2, Herpes Zoster, Human parvovirus (B19), Respiratory syncytial virus, Pox viruses (all types and serotypes), Coltivirus, Reoviruses-all types, and/or Rubivirus (rubella).

Antigens useful in the present disclosure may include those derived from bacteria including, but not limited to, *Streplococcus agalactiae, Legionella pneumophilia, Streptococcus pyogenes, Escherichia coli, Neisseria gonorrhosae, Neisseria meningitidis*, Pneumococcus, Hemophilis *influenzae* B, *Treponema pallidum*. Lyme disease spirochetes, *Pseudomonas aeruginosa, Mycobacterium leprae, Brucella abortus, Mycobacterium tuberculosis, Plasmodium falciparum, Plasmodium vivax, Toxoplasma gondii*, Trypanosoma *rangeli*, Trypanosoma *cruzi*, Trypanosoma rhodesiensei, Trypanosoma *brucei, Schistosoma mansoni, Schistosoma japanicun, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium, M. pneumoniae, Candida albicans, Cryptococcus neoformans, Histoplasma capsulatum, Coccidioides immitis, Blastomyces dernatitidis, Aspergillus fumigatus, Penicillium marneffei, Bacillus anthracis, Bartonella, Bordetella pertussis, Brucella*—all serotypes, *Chlamydia trachomatis, Chlarnydia pneunoniae, Clostridium botulinum*—anything from *clostridium* serotypes, *Haemophilus influenzae, Helicobacter pylori, Klebsiella*—all serotypes, *Legionella*—all serotypes, *Listeria, Mycobacterium*—all serotypes, *Mycoplasma*—human and animal serotypes, *Rickettsia*—all serotypes, *Shigella*—all serotypes, *Staphylococcus aureus, Streptococcus—S. pneumoniae, S. pyogenes, Vibrio cholera, Yersinia enterocolitica*, and/or *Yersinia pestis*.

Antigens useful in the present disclosure may include those derived from parasites including, but not limited to, *Ancylostoma* human hookworms, *Leishmania*—all strains, *Microsporidium*, Necator human hookworms, *Onchocerca* filarial worms, *Plasmodium*—all human strains and simian species, *Toxoplasma*—all strains, Trypanosoma—all serotypes, and/or *Wuchereria bancrofti* filarial worms.

In another embodiment, an antigen is an aberrant protein derived from a sequence which has been mutated. Such antigens may include those expressed by tumor cells or aberrant proteins whose structure or solubility leads to the formation of an aggregation-prone product and cause disease. Examples of aberrant proteins may include, but are not limited to, Alzheimer's amyloid peptide, SOD1, presenillin 1 and 2, α-synuclein, amyloid A, amyloid P, CFTR, transthyretin, amylin, lysozyme, gelsolin, p53, rhodopsin, insulin, insulin receptor, fibrillin, α-ketoacid dehydrogenase, collagen, keratin, PRNP, immunoglobulin light chain, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, dentaorubral pallidoluysian atrophy-associated protein, maltose-binding protein, ABC transporter, glutathione-S-transferase, and thioredoxin.

In one embodiment, a vaccine composition comprising an amorphous solid may be made by preparing a solution comprising a sugar, sugar derivative or combination of sugars/derivatives in a buffer and optionally other additives previously mentioned. In some embodiments, a sugar, sugar derivative or combination of sugars/derivatives may be present in the solution in an amount up to about 60% by weight of the solution. In some embodiments, an additive may be present in an amount of about 5% or less by weight of the solution. In general, the solution comprising the sugar, sugar derivative or combination of sugars/derivatives is made at a concentration higher than the desired final concentration to compensate for any dilution that may occur when the antigen is added. The desired antigen may be added to the solution at a concentration known to induce the desired immune response. The mixture may then be stirred at ambient temperature until a substantially homogeneous mixture is obtained. In some embodiments, the mixture may then be briefly sonicated under cooled conditions, e.g. 4° C., to remove any air bubbles that may have developed. In other embodiments, the mixture may be slightly heated, e.g., heated to 40° C. or below, slightly cooled, and in some instances may be frozen. In some embodiments, a vaccine composition of the present disclosure may be made without freeze drying or spray draying. The final formulation may then be cast onto a flat backing surface in a laminar flow hood and allowed to form an amorphous solid at ambient temperatures (15-20° C.). Examples of suitable backing surfaces may include, but are not limited to, thin layers of aluminum, Teflon, silicate, polyetheretherketone, low density polyethylene, ethyl cellulose, etc. Once the process is complete the vaccine composition can be peeled from the backing and placed in the mouth for immunization purposes and/or stored at ambient temperature for up to three years from manufacture.

In another embodiment, a vaccine composition of the present disclosure may be made by contacting an amorphous solid with an antigen, or optionally, mixing an antigen with one or more excipients (surfactants, sugars, starches, etc.) and contacting the amorphous solid with the mixture so as to dispose the antigen within the amorphous solid. In some embodiments, the mixture is then allowed to dry, which is then ready for administration.

In some embodiments, vaccine compositions of the present disclosure may further comprise a protective layer disposed on a surface of an amorphous solid comprising an antigen. Exemplary protective layers may include, but are not limited to, an additional layer(s) of film, such as polyethylene, polyurethane, polyether etherketone, etc., and/or an additional layer(s) of an amorphous solid that does not contain any antigen.

The amount of antigen that may be used in a vaccine composition of the present disclosure may vary greatly depending upon the type of antigen used, the formulation used to prepare the vaccine composition, the size of the amorphous solid, the solubility of the antigen, etc. One of ordinary skill in the art with the benefit of this disclosure will be able to determine a suitable amount of antigen to include in a vaccine composition of the present disclosure. In one embodiment, a vaccine composition may comprise about $1 \times 10^6$ to about $1 \times 10^{13}$ virus particles for a virus-based vaccine or about $1 \times 10^3$ to about $1 \times 10^{13}$ colony forming units for a bacteria-based vaccine or about 0.1 mg-1 g of protein for subunit vaccines.

It is also important to note that when formulating a vaccine composition of the present disclosure one must also consider any toxicity and/or adverse effects. Furthermore, in an effort to create a stable vaccine composition, it may also be important to identify a ratio of ingredients that interacts with water and the antigen in a manner that prevents crystallization during drying. Formation of water crystals will puncture the virus coat or bacterial wall and compromise the overall potency of the vaccine. Formulations that do this to the highest degree are said to form glasses.

Any substantially solid surface can be used for casting and/or drying compositions of the embodiments. For example, the surface can be a polymer (e.g., plastic) or a metal surface. In some aspects, the surface has a low coefficient of friction (e.g., a siliconized, non-stick surface) to provide easy removal of films. In some embodiments, a glass plate can be used for casting of the vaccine compositions. Composition that have been cast on a surface can then be dried, for instance, under a controlled, laminar flow of air at room temperature, or under refrigerated conditions. Similarly, vaccine compositions suitable for use in the present disclosure can be prepared in a single-layer or multi-layers.

In general, the vaccine compositions of the present disclosure may be formulated so as to dissolve in a relatively short period of time, for example, from about 5 to 60 seconds or 1 to 30 minutes. When administered, a vaccine composition of the present disclosure may be handled by a portion of the composition that does not contain an antigen and may be placed in the upper pouch of the cheek for buccal delivery, or far under the tongue for sublingual delivery or reconstituted and utilized as a solution for inhalation or as a nasal spray.

In some embodiments, the compositions and methods of the present disclosure may also be used as a means for treating a variety of malignant cancers. For example, the vaccine compositions of the present disclosure can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc.; any of the various tyrosinases; MART 1 (melanoma antigen recognized by T cells), mutant ras; mutant p53; p97 melanoma antigen; CEA (carcinoembryonic antigen), among others.

In certain aspects, methods are provided for producing immunogenic compositions in substantially solid carriers. Such a method may comprise obtaining or formulating a solution comprising sufficient stabilizers (e.g., sugars and sugar derivatives, polymers) and permeability enhancers (e.g., surfactants, such as a zwitterionic surfactant of the embodiments) in a solvent system (e.g., distilled deionized water, ethanol, methanol). In some cases, formulation is such that the total amount of solid components added to the solvent are within the concentration of 10%-90% w/w. This suspension can be prepared by stirring, homogenization, mixing and/or blending these compounds with the solvent. In some cases, small portions of each component (~1/10 the total amount) are added to the solvent and the solution mixed before adding additional portions of the same agent or a new agent.

In certain aspects, once each stabilizer and permeability enhancer is added, the bulk solution is placed at 4° C. for a period of time between 2-24 hours. In some aspects, the bulk solution is subjected additional homogenization, such as sonication (e.g., for a period of 5-60 minutes) to remove trapped air bubbles in the preparation. After sonication is complete, the antigen, such as a viral vector, is added to the preparation. In some cases, the amount of antigen will range from of 0.1-30% of the total solid concentration. Adjuvants, optionally, can also be added at this time. In some aspects, the amount of adjuvant compounds will range from 0.005-10% of the total solid concentration. Again, in some aspects, these agents will be added by gentle stirring (e.g., 10-50 rpm) so as to not induce airpockets/bubble formation in the final preparation.

In some cases, the preparation is then slowly piped into molds of a shape suitable for the application. The molds can be constructed of a variety of materials including, but not limited to, stainless steel, glass, silicone, polystyrene, polypropylene and other pharmaceutical grade plastics. In some cases, the preparation can be placed in the molds by slowly pouring by hand or by pushing the preparation through a narrow opening on a collective container at a slow controlled rate (e.g., 0.25 ml/min) to prevent early hardening and/or bubble formation in the final film product. In certain preferred aspects, films will be poured to a thickness of 12.5-1000 µm. In some aspects, molds for casting of films will be sterilized by autoclaving and placed in laminar air flow hoods prior to casting.

In further aspects, molds may also be lined with a peelable backing material suitable for protection of the film product. Suitable backings include, without limitation, aluminum, gelatin, polyesters, polyethylene, polyvinyl and poly lactic co-glycolide polymers, wax paper and/or any other pharmaceutically acceptable plastic polymer.

In some cases, cast films will remain at ambient temperature (e.g., 20-25° C.), such as in a laminar flow hood for 2-24 hours after which time a thin, peelable film will be formed. In some cases, this film may be opaque or translucent. In some cases, films are stored at room temperature under controlled humidity conditions. However, in certain aspects, films can be stored at lower temperatures, such as at 4° C., under controlled humidity as well.

In certain aspects, multilayer films can also be created at this time by applying a second coating of as solution containing the same antigen as the first layer or another different adjuvant/antigen system to the thin film. Again, in some cases, this will remain at ambient temperature (e.g., 20-25° C.), such as in a laminar flow hood, for an additional 2-24 hours after which time a thin, peelable film will be formed. Again the film may be opaque or translucent.

In certain cases, films will be dissolved in a solution prior to use. For example, water or warmed saline (e.g., ~37° C., body temperature) may be used. In some cases, the resulting solution can be screened for antigen confirmation and activity to determine the effectiveness of the formulation to retain the potency of the preparation over time.

To facilitate a better understanding of the present invention, the following examples of certain aspects of some embodiments are given. In no way should the following examples be read to limit, or define, the entire scope of the invention.

EXAMPLE 1

Materials and Methods (Examples 2-8)

Materials—Acepromazine was purchased from Fort Dodge Laboratories (Atlanta, Ga.). Ketamine was purchased from Wyeth, Fort Dodge, Animal Health, (Overland Park, Kans.). Dulbecco's phosphate-buffered saline (DPBS), xylazine, tresyl chloride activated monomethoxypoly(ethylene) glycol, L-lysine, Poly(ethylene) glycol 3000, ethyl acetate, poly(lactide-co-glycolide) copolymers (PLGA, 50:50 lactide:glycolide), polyvinyl alcohol (PVA), glutaraldehyde (Grade I, 25% in water), o-phenylenediamine, sucrose (USP grade), D-mannitol (USP grade), D-sorbitol (USP grade), bovine serum albumin (RIA grade), Brefeldin A, potassium ferricyanide and potassium ferrocyanide were purchased from Sigma-Aldrich (St. Louis, Mo.). Eosin Y and Tween 20 were purchased from Fisher Scientific (Kalamazoo, Mich. and Pittsburgh, Pa. respectively). Melezitose monohydride was purchased from MP Biomedicals (Solon, Ohio) and raffinose pentahydrate from Alfa Aesar (Ward Hill, Mass.). Sodium hydroxide, potassium phosphate monobasic, potassium phosphate dibasic and sodium dodecyl sulfate were purchased from Mallinckrodt Baker (Phillipsburg, N.J.). Pluronic F68 was purchased from BASF (Mount Olive, N.J.). Dulbecco's Modified Eagle's medium (DMEM), RPMI-1640, Minimal Essential Medium (MEM) and L-glutamine were purchased from Mediatech (Manassas, Va.). Fetal bovine serum (qualified, US origin), penicillin and streptomycin were purchased from Gibco Life Technologies (Grand Island, N.Y.). Sodium pyruvate and non-essential amino acids were purchased from Lonza (Walkersville, Md.). 5-bromo-4-chloro-3-indolyl-β-D-galactoside (X-gal) was purchased from Gold Biotechnology (St. Louis, Mo.). N-dodecyl-β-D-maltopyranoside (nDMPS), poly (Maleic Anhydride-alt-1-Decene) substituted with 3-(Dimethylamino) Propylamine (PMAL C8, formula weight (F.W.) 8,500), poly (Maleic Anhydride-alt-1-Tetradecene) substituted with 3-(Dimethylamino) Propylamine (PMAL C12, F.W. 12,000) and poly (Maleic Anhydride-Alt-1-Octadecene) substituted with 3-(Dimethylamino) Propylamine (PMAL C16, F.W. 39,000) were purchased from Anatrace (Maumee, Ohio). The TELRTFSI (SEQ ID NO: 1) peptide was purchased from New England Peptide (Gardner, Mass.). The negative control peptide (YPYDVPDYA (SEQ ID NO: 2)) was purchased from GenScript (Piscataway, N.J.). Antibodies used for ELISPOT and flow cytometry, Cytofix/Cytoperm and Perm/Wash reagents were purchased from BD Pharmingen (San Diego, Calif.).

Adenovirus Production—Four different recombinant adenoviruses were used in these examples. All were first generation E1/E3 deleted recombinant adenovirus serotype 5 vectors that differed only by transgene expression cassettes. Two vectors, AdlacZ, expressing *E. coli* beta-galactosidase and AdGFP, expressing green fluorescent protein were used for rapid screening of the transduction efficiency of formulations in vitro and in vivo due to the ease by which their transgene products could be visualized and quantitated. AdNull, an E1/E3 deleted adenovirus 5 vector with a similar genetic backbone as the other viruses used in these examples except that it does not contain a marker transgene expression cassette, was used to induce pre-existing immunity to adenovirus 5 in mice prior to immunization. These viruses were each amplified in HEK 293 cells (ATCC CRL-1573 Manassas, Va.). They were purified from cell lysates by banding twice on cesium chloride gradients and desalted over Econo-Pac 10 DG disposable chromatography columns (BioRad, Hercules, Calif.) equilibrated with potassium phosphate buffer (KPBS, pH 7.4). The concentration of each preparation was determined by UV spectrophotometric analysis at 260 nm and by an infectious titer assay as described[18]. Preparations with a ratio of infectious to physical particles of 1:100 were used for these examples. For immunization and challenge studies, an E1/E3 deleted recombinant adenovirus serotype 5 vector expressing a codon optimized full-length Ebola glycoprotein sequence under the control of the chicken β-actin promoter (Ad-CAGoptZGP) was amplified in HEK 293 cells and purified as describe d (Choi et al., 2013). Concentration of this and AdNull was determined by UV spectrophotometric analysis at 260 nm and with the Adeno-X Rapid Titer Kit (Clontech, Mountain View, Calif.) according to the manufacturer's instructions. Preparations with infectious to physical particle ratios of 1:200 of each of these viruses were used in these examples.

PEGylation of Adenovirus—PEGylation was performed according to established protocols (Croyle et al., 2000; Wonganan et al., 2010). Characterization of these preparations revealed significant changes in the biophysical properties of the virus such as the PEG-dextran partition coefficient and peak elution times during capillary electrophoresis (Wonganan et al., 2010). Approximately 18,245±546 PEG molecules were associated with each virus particle in the examples outlined here as determined by a PEG-biotin assay (Croyle et al., 2005).

PLGA Microspheres—PLGA microspheres were prepared using a standard water-in-oil-in-water (W/O/W) double emulsion and solvent evaporation method (Danhier et al., 2012). One milliliter of virus ($5\times10^{12}$ virus particles) was added to ethyl acetate containing 100 mg PLGA. The primary water-in-oil emulsion was prepared by homogenization for 30 seconds and was then added to 10 milliliters of an aqueous solution containing 5% (w/v) PVA. The secondary W/O/W emulsion was prepared by homogenization for 60 seconds and further agitated with a magnetic stirring rod for 2 hours at 4° C. to evaporate the co-solvent. Microspheres were collected by centrifugation at 2,000 rpm for 3 minutes and washed five times with sterile KPBS. The diameter of the microspheres fell between 0.3 to 5 μm with an average particle size of 2.06±1.4 μm as determined by dynamic light scattering using a DynaPro LSR laser light scattering device and detection system (Wyatt Technology, Santa Barbara, Calif.). Regularization histograms and assignment of hydrodynamic radii values to various subpopulations within the sample were calculated using DynaLS software (Wyatt). The amount of virus embedded in the microspheres was determined by digesting a portion of each preparation with 1 N NaOH for 24 hours. The average encapsulation efficiency of this process was 21.6±4.4% (n=6). Aliquots of each preparation were dried, placed in sterile, light resistant containers and stored at room temperature for evaluation of stability over time. Release profiles of each preparation were determined by placing 10 mg of microspheres in 0.5 ml sterile KPBS on a magnetic stir plate (Corning, Tewksbury Mass.) in a 37° C. incubator. Each day, microspheres were collected by centrifugation, the supernatant collected and replaced with KPBS pre-warmed to 37° C. The number of infectious virus particles released from microspheres was determined by serial dilution of collected samples and subsequent infection of Calu-3 cells (ATCC, HTB-55), an established model of the airway epithelia (Ong et al., 2013).

EXAMPLE 2

In Vitro Screening of Formulations

Two vectors, AdlacZ, expressing *E. coli* beta-galactosidase and AdGFP, expressing green fluorescent protein were used for rapid screening of the transduction efficiency of formulations due to the ease by which their transgene products could be visualized and quantitated. Formulations were prepared at five times the working concentration, sterilized by filtration and diluted with freshly purified virus in KPBS (pH 7.4) prior to use. Two hundred microliters of formulation containing virus (MOI 100) in the absence or presence of anti-adenovirus antibodies were added to differentiated Calu-3 cells seeded at a density of $1.25\times10^5$ cells/well in 12 well plates. Formulations remained in contact with cell monolayers for 2 hours at 37° C. in 5% $CO_2$. Cytotoxicity was assessed by measuring lactate dehydrogenase (LDH) release into the formulation with a standard cytotoxicity kit (Roche Applied Science, Indianapolis, Ind.) according to the manufacturer's instructions. Complete lysis was achieved by adding 1% sodium dodecyl sulfate to cells not exposed to formulations (positive control). Transduction efficiency was measured 48 hours later by either histochemical staining, visual inspection and quantitation of cells expressing beta-galactosidase or by flow cytometry to quantitate cells expressing GFP.

EXAMPLE 3

Mouse Studies

All procedures were approved by the Institutional Animal Care and Use Committees at The University of Texas at Austin and the University of Texas Medical Branch in Galveston and are in accordance with the guidelines established by the National Institutes of Health for the humane treatment of animals. Two different strains of mice were used in these examples. Male B10.Br mice (MHC H-$2^k$) were used to characterize the immune response to Ebola glycoprotein after immunization with the Ad-CAGoptZGP vector as described previously (Croyle et al., 2008; Choi et al., 2012; Choi et al., 2013). Because this strain is difficult to breed (Lerner et al., 1992), and is often not readily available in quantities sufficient from the supplier to perform the studies outlined in this manuscript, male C56/BL6 (MHC H-$2^d$) mice were used for initial screening of formulations that improved transgene expression in vitro with minimal cytotoxic effects. Both strains were obtained from the Jackson Laboratory (age 4-6 weeks, Bar Harbor, Me.).

Nasal Administration of Virus/Immunization—Animals were housed in a temperature-controlled, 12 hour light-cycled facility at the Animal Research Center of The University of Texas at Austin with free access to standard rodent chow (Harlan Teklad, Indianapolis, Ind.) and tap water. Animals were anesthetized by a single intra-peritoneal injection of a 3.9:1 mixture of ketamine (100 mg/ml) and xylazine (100 mg/ml). Once deep plane anesthesia was achieved, animals were placed on their stomach. The sedate animal's head was rested upon an empty tuberculin syringe to keep the head in an upright position and to minimize choking or accidental swallowing of vaccine (FIG. 9). Each mouse received a dose of $1\times10^8$ infectious particles of unformulated or formulated vaccine by direct application in the nasal cavity. The inhalation pressure from the animal's natural breathing was sufficient to allow small droplets from the standard micropipette (Gilson, Middleton, Wis.) to gently enter the nasal cavity without the need to forcefully inject the solution. The right nostril received 10 μL and was allowed to dry for up to 5 minutes before adding an additional 10 μL to the left nostril, for a total volume of 20 μL per animal. The animal was observed in the relaxed position for an additional 10 minutes to guarantee comfortable breathing and ensure that the vaccine was not lost via sneezing (a rare occurrence that can result from touching the animal's nose with the micropipette tip instead of allowing the tiny droplet to be gently pulled into the nose through natural inhalation pressure).

Establishment of Pre-Existing Immunity to Adenovirus—A first generation adenovirus that that does not contain a transgene cassette (AdNull) was used to establish pre-existing immunity to adenovirus serotype 5 (Callahan el al., 2006). Twenty-eight days prior to vaccination, mucosal PEI was induced by placing $5 \times 10^{10}$ particles of AdNull in the nasal cavity as described above under the immunization protocol. Twenty-four days later, blood was collected via the saphenous vein and serum screened for anti-Ad neutralizing antibodies (NABs) as described below. At the time of vaccination, animals had an average anti-Ad circulating NAB titer of 315±112 reciprocal dilution, which falls within the range of average values reported in humans after natural infection (Barouch et al., 2011).

Challenge with Mouse-Adapted Ebola Virus—Challenge experiments were performed under biosafety level 4 (BSL-4) conditions in an AAALAC accredited animal facility at the Robert E. Shope BSL-4 Laboratory at the University of Texas Medical Branch in Galveston, Tex. Twenty-one days post-immunization, vaccinated mice were transported to the BSL-4 lab where they were challenged on day 28 by intraperitoneal injection with 1,000 pfu of mouse-adapted ($30{,}000\times LD_{50}$) Ebola (Bray et al., 1999). After challenge, animals were monitored for clinical signs of disease and weighed daily for 14 days. Serum alanine aminotransferase (ALT) and aspartate aminotransferase (AST) levels were determined using AST/SGOT and ALT/SGPT DT slides on a Vitros DTSC autoanalyzer (Ortho Clinical Diagnostics, Rochester, N.Y.).

EXAMPLE 4

In Vitro Studies with Immunized Samples

ELISPOT—ELISpot assays were performed using the ELISpot Mouse Set (BD Pharmingen) according to the manufacturer's instructions. Mononuclear cells were isolated from the spleen and bronchoalveolar lavage fluid as described previously (Choi et al., 2013), washed twice with complete DMEM and added to wells of a 96-well ELISpot plate ($5\times10^5$ cells/well) with the TELRTFSI peptide ((SEQ ID NO: 1), 0.5 μg/well) that carries the Ebola virus glycoprotein immunodominant MHC class I epitope for mice with the H-$2^k$ haplotype (B10.Br) (Rao et al., 1999). Negative control cells were stimulated with an irrelevant peptide, which carries a binding sequence for influenza hemagglutinin (YPYDVPDYA (SEQ ID NO: 2), 0.5 μg/well). Spots were counted using an automated ELISpot reader (CTL-ImmunoSpot® S5 Micro Analyzer, Cellular Technology Ltd., Shaker Heights, Ohio).

Multi-Parameter Flow Cytometry—Splenocytes ($2\times10^6$) isolated from immunized mice were cultured with TELRTFSI peptide ((SEQ ID NO: 1), 0.5 μg/well) and 1 μg/ml Brefeldin A for 5 hours at 37° C. in 5% $CO_2$. Negative control cells were incubated with the YPYDVPDYA peptide ((SEQ ID NO: 2), 0.5 μg/well). Following stimulation, cells were surface stained with anti-mouse CD8α antibodies (1:150 in DPBS) and followed by intracellular staining with anti-mouse IFN-γ, TNF-α and IL-2 antibodies as described (Choi et al., 2013). Positive cells were counted using four-color flow cytometry (FACS Fortessa, BD Biosciences, Palo Alto, Calif.). Over 500,000 events were captured per sample. Data were analyzed using FlowJo software (Tree Star, Inc., Ashland, Oreg.).

CFSE Assay—Splenocytes were isolated 42 days post-vaccination, stained using the Vybrant CFDA SE Cell Tracer kit (Invitrogen, Carlsbad, Calif.), seeded at a concentration of $5\times10^5$ cells/well in 96 well plates and cultured for 5 days at 37° C. with 5% $CO_2$ in the presence of the TELRTFSI (SEQ ID NO: 1) or YPYDVPDYA (SEQ ID NO: 2) peptides (0.5 μg/well) as described previously (Choi et al., 2012). Cells were incubated with a cocktail of antibodies (perCPCy5.5 labeled-anti-mouse-CD8, PE labeled-anti-mouse-CD44, and allophycocyanin (APC) labeled-anti-mouse-CD62L, 1:150) and analyzed by flow cytometry with over 1,000,000 events captured per sample.

Characterization of Ebola Glycoprotein-Specific Antibodies—Flat bottom, Immulon 2HB plates (Fisher Scientific, Pittsburgh, Pa.) were coated with purified Ebola virus $GP_{33-637}$ ΔTM-HA (3 μg/well) in PBS (pH 7.4) overnight at 4° C. (Lee et al., 2009). Heat-inactivated serum samples were diluted (1:20) in PBS. One hundred microliters of each dilution were added to antigen-coated plates for 2 hours at room temperature. Plates were washed 4 times and incubated with HRP-conjugated goat anti-mouse IgG, IgG1, IgG2a, IgG2b and IgM (1:2,000, Southern Biotechnology Associates, Birmingham, Ala.) antibodies in separate wells for 1 hour at room temperature. Plates were washed and substrate solution added to each well. Optical densities were read at 450 nm on a microplate reader (Tecan USA, Research Triangle Park, NC).

Adenovirus Neutralizing Assay—Heat-inactivated serum was diluted in twofold increments starting from a 1:20 dilution. Each dilution was incubated with AdlacZ ($1\times10^6$ pfu) for 1 hour at 37° C. and applied to HeLa cells (ATCC #CCL-2) seeded in 96-well plates ($1\times10^4$ cells/well). After this time, 100 μl of DMEM supplemented with 20% FBS were added to each well. Twenty-four hours later, beta-galactosidase expression was measured by histochemical staining. Dilutions that reduced transgene expression by 50% were calculated using the method of Reed and Muench (reed et al., 1938). The absence of neutralization in samples containing medium only (negative control) and FBS (serum control) and an average titer of 1:1,280±210 read from an internal positive control stock serum were the criteria for qualification of each assay.

Statistical Analysis—Data were analyzed for statistical significance using SigmaStat (Systat Software Inc., San Jose, Calif.) by performing a one-way analysis of variance (ANOVA) between control and experimental groups, followed by a Bonferoni/Dunn post-hoc test when appropriate. Differences in the raw values among treatment groups were considered statistically significant when $p<0.05$.

EXAMPLE 5

Characterization of Formulations

A variety of novel formulations were identified, prepared and evaluated for their ability to maintain or improve transduction efficiency of the adenovirus with minimal cytotoxicity in Calu-3 cells, an in vitro model of the human respiratory epithelium (Ong et al., 2013). Over 400 formulations were assessed using a recombinant adenovirus expressing E. coli beta-galactosidase that differed from the inventors' vaccine construct only by the transgene cassette. This virus was chosen for these studies because it was available in sufficient quantity to support the high-throughput screening approach used by the inventors and for the ease by which the beta-galactosidase transgene product could be visualized and quantitated in vitro and in vivo. Data summarized here illustrate the inventors' heuristic approach where the number of formulation candidates tested in vitro is significantly reduced prior to the first in vivo screen for transduction efficiency and safety and further reduced to a select few for characterization of the immune response and subsequent evaluation of protection from lethal exposure to rodent-adapted Ebola.

In Vitro Characterization of Formulated Adenovirus Preparations—While many of the formulations included in the initial screen could maintain the stability of the adenovirus at ambient temperatures (data not shown), very few improved the in vitro transduction efficiency of the virus above that seen from virus formulated in saline. However, a preparation of 5% w/v sucrose increased transduction efficiency by a factor of 1.96 with respect to virus formulated in saline (pH 7.4, FIG. 21A). Pluronic F68 (0.005% w/v), mannitol (1.25% w/v) and melezitose (1.25% w/v) alone each increased transduction by a factor of 1.78, 1.61 and 1.51, respectively. Formulations consisting of either raffinose or sorbitol alone at a 1.25% (w/v) concentration did not significantly enhance transduction (p=0.06). A multi-component formulation, F3, consisting of sucrose (10 mg/ml), mannitol (40 mg/ml) and 1% v/v poly(ethylene) glycol 3,000, previously found to stabilize the virus at ambient temperatures for extended periods of time (Renteria et al., 2010), increased transduction fivefold (p=0.03). A formulation of 100 μM nDMPS was the second most efficacious formulation, however, significant cytotoxicity (>80% cell lysis) was observed in cultures treated with this formulation. Less than 1% lysis was observed in cells treated with F3, making it suitable for further evaluation in vivo (data not shown).

In an effort to improve transduction efficiency in the presence of anti-adenovirus neutralizing antibodies, a method for encapsulation of adenovirus with the bio-compatible polymer poly(lactic-co-glycolic acid) was also developed (Choi et al., 2012). Only preparations that were capable of releasing active virus at concentrations relevant for immunization after storage at ambient temperatures would be considered for further in vivo testing. Approximately 10±0.43% of the virus particles embedded in the polymer matrix were rendered uninfectious during processing, leaving the average virus concentration to be 1.08±0.5× $10^9$ infectious virus particles (ivp) per milligram of microspheres. Infectious virus particles were released for 14 days after which virus could no longer be detected (FIG. 1B). Approximately 50% of the total amount of infectious virus embedded in freshly made polymer beads and in beads stored at 25° C. for 7 days was released within 24 hours (FIG. 1C). Storage of the beads at room temperature for 7 days did not significantly impact release rate as $1.34 \times 10^8$ ivp were released per day from freshly prepared beads and $1.76 \times 10^8$ ivp released per day after this time. Storage at room temperature for one month increased the rate of release to $3.5 \times 10^8$ ivp/day and promoted release of the entire dose (97.95%) within 48 hours (FIG. 1C).

In Vivo Transduction Efficiency of Formulated Adenovirus Preparations in Naïve Mice and Those with Pre-Existing Immunity—Based upon their ability to improve transduction efficiency and maintain virus stability, the F3 formulation and PLGA microspheres were selected for further evaluation of their effect on the transduction efficiency of adenovirus in naive mice and those with pre-existing immunity (PEI) to adenovirus. PEGylated virus was also selected for evaluation as a vaccine platform since the inventors have previously shown that covalent attachment of poly(ethylene) glycol to the virus capsid improves the transduction efficiency in animals that have been exposed to adenovirus (Croyle et al., 2001). Intranasal administration of AdlacZ, the model virus used for in vitro screening studies summarized in FIGS. 1A-IC, in each respective formulation resulted in high levels of transgene expression in epithelial cells of the conducting airways of naïve mice 4 days after treatment (FIGS. 2A-2D). More importantly, each formulation significantly improved transgene expression in mice with pre-existing immunity to adenovirus (FIGS. 2F-2H) with respect to unformulated virus (FIG. 2E).

EXAMPLE 6

Characterization of Immune Response

The T Cell Response: Magnitude—Since the transduction efficiency data in mice with pre-existing immunity to adenovirus looked promising for each formulation, the immune response elicited by each formulation was evaluated in B10.Br mice with the Ad-CAGoptZGP vector as described previously (Croyle et al., 2008; Choi et al., 2012; Choi et al., 2013). The systemic antigen-specific T cell response generated by each formulation candidate was evaluated by quantitation of IFN-γ secreting mononuclear cells (MNCs) in the spleen by ELISpot. There was no significant difference in the amount of antigen-specific cells present in samples obtained from naïve animals immunized with PEGylated, PLGA encapsulated or unformulated virus (p>0.05, FIG. 3A). Samples from mice immunized with the F3 formulation contained slightly more antigen-specific cells than those from mice given unformulated vaccine (486.7±4.8 spot-forming cells (SFCs)/million MNCs, F3 vs. 414.7±27.6 SFCs/million MNCs, Unform.). In contrast to what was observed in naïve animals, PEI significantly decreased the number of activated IFN-γ secreting MNCs in the spleens of animals given each preparation except in those given the PEGylated vaccine (317.3±58.2 spot-forming cells (SFCs)/million mononuclear cells (MNCs), naïve vs. 234.7±54.3 SFCs/million MNCs, PEI, FIG. 3A). The most significant reduction in IFN-γ secreting MNCs was observed in animals given the microsphere preparation (426.7±33.8 SFCs/million MNCs, Naive vs. 57.3±7.1 SFCs/million MNCs, PEI). Pre-existing immunity also significantly reduced the number of IFN-γ secreting cells recovered from bronchioalveolar lavage (BAL) fluid in mice given unformulated vaccine (1,513.3±63.6 SFCs/million MNCs, naïve vs. 526.7±98.2 SFCs/million MNCs, PEI, p<0.01, FIG. 3B). This response was not compromised in animals given the PEGylated and PLGA encapsulated vaccines (PEG: 266.7±54.6 SFCs/million MNCs, naïve vs. 580±61.1 SFCs/million MNCs, PEI; PLGA: 1280±90.2 SFCs/million MNCs, naïve vs. 1360±231.8 SFCs/million MNCs, PEI).

The T Cell Response: Quality—Both the quantity and quality of antigen-specific CD8$^+$ T cells induced by a vaccine platform significantly contribute to protection from a variety of infectious diseases such as AIDS, malaria, and hepatitis C (Fraser et al., 2013). In animal models of infection, the quality of the antigen-specific T cell response can be assessed by stimulation of splenocytes, intracellular staining and multi-parameter flow cytometry to characterize the diversity of CD8$^+$ T cell populations induced after immunization (Zielinski et al., 2011). The presence of poly-functional CD8$^+$ T cells, capable of producing several cytokines (IFN-γ, IL-2, and TNF-α) in response to the antigen, has been found to correlate with a reduction in circulating antigen and viral load since they are known to be the most responsive cells early in the infection process (Seder et al., 2008). Thus, strategies to increase the presence of cells capable of producing variety of cytokines and chemokines in response to a pathogen are part of many immunization strategies (Sallusto et al., 2010; Coffman et al., 2010). In this context, functional analysis of cytokine producing CD8$^+$ T cells at the single-cell level was performed to determine the ability of the formulations described herein to improve the quality of the antigen-specific CD8$^+$ T cell response. As part of this analysis, the inventors were able to delineate seven distinct cytokine-producing cell populations based upon IFN-γ, IL-2, and TNF-α secretion patterns.

As stated above, the relative frequency of cells that produce all three cytokines defines the quality of the vaccine-induced CD8$^+$ T cell response. In naïve mice, each formulation increased the number of poly-functional CD8$^+$ T cells, with the PLGA encapsulated vaccine producing the highest amount of these cells (IFN-γ$^+$IL-2$^+$TNF-α$^+$, 37.1±5.04%, FIG. 3C). Prior exposure to adenovirus in the nasal mucosa reduced the quality of the response generated by the unformulated vaccine (23.9±3.24%, Naive vs. 19.1±6.76%, PEI) and F3 (27.2±4.60%, Naive vs. 14.8±2.85%, PEI) while the response induced by the PEGylated vaccine was not compromised (24.8±3.69%, Naive vs. 26.9±4.74%, PEI, FIG. 3D). The poly-functional response was somewhat strengthened in mice with prior exposure to adenovirus given the PLGA microspheres (37.1±5.04%, Naive vs. 41.7±7.88%, PEI). This effect was also seen 42 days after immunization.

Figures 3A, 3B, 3C, 3D, 3E:
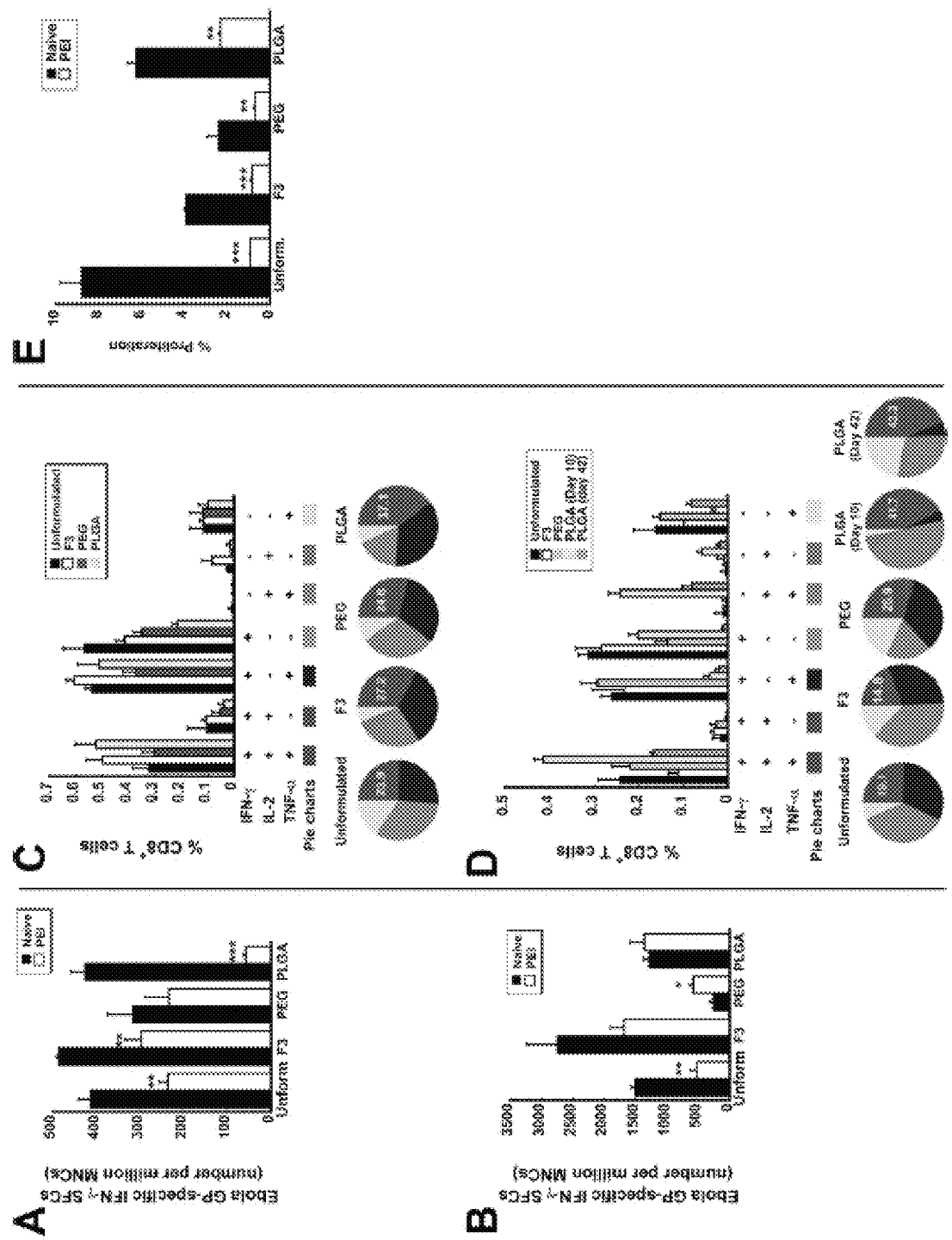
FIGS. 3A-3E: Formulated Preparations Maintain Antigen Specific Poly-Functional T Cell Responses in Naïve Mice and Those with Prior Exposure to Adenovirus. Characterization of the immune response to Ebola glycoprotein was performed in B10.Br mice as described previously (Patel et al., 2007; Croyle et al., 2008; Choi et al., 2012; Choi et al., 2013). (3A) Magnitude of the Systemic CD8+ T Cell Response Against Ebola Glycoprotein. The number of IFN-γ secreting mononuclear cells was quantitated in isolates taken 10 days after immunization from the spleen of naïve B10.Br mice and those with prior-exposure to adenovirus by ELISpot. (3B) Magnitude of the Mucosal CD8+ T Cell Response Against Ebola Glycoprotein. The number of IFN-γ secreting mononuclear cells was quantitated 10 days after immunization in bronchioalveolar lavage (BAL) fluid of naïve mice and those with prior-exposure to adenovirus by ELISpot. (3C) Polyfunctionality of the Ebola Glycoprotein-specific T Cell Response in Naïve mice. Ten days after immunization, splenocytes from 5 mice per treatment group were pooled and stimulated with an Ebola glycoprotein-specific peptide. Bar graphs illustrate the percentage of CD8+ tumor necrosis factor α (TNF-α)-, interleukin 2 (IL-2)- and interferon γ (IFN-γ)-producing cells detected after 5 hours of antigen stimulation. Distribution of single-, double- and triple-cytokine-producing CD8+ T cells is shown as various colors in pie chart diagrams. The relative frequency of cells that produce all three cytokines defines the quality of the vaccine-induced CD8+ T cell response. The proportion of these cells (IFN-γ$^+$IL-2$^+$TNF-α$^+$) generated in response to each treatment is written in the red section of each pie chart while the proportion of cells producing a single cytokine are represented by the light blue, purple and yellow sections of each pie chart. (3D) Polyfunctionality of the Ebola Glycoprotein-Specific T Cell Response in Mice with Prior Exposure to Adenovirus. Pre-existing immunity to adenovirus 5 was induced by instilling $5 \times 10^{10}$ virus particles of AdNull, an E1/E3 deleted virus that does not contain a transgene cassette, in the nasal cavity of mice 28 days prior to immunization. Ten days after immunization, splenocytes were harvested and pooled as described in 3C. An increase in the number of polyfunctional cells, as indicated by an increase in the size of the red section of each pie graph, was fostered by several of the test formulations with respect to that produced by unformulated vaccine. (3E) Quantitative Analysis of the Effector Memory T Cell Response. Splenocytes were harvested 42 days after immunization, stained with CFSE and stimulated with the TELRTFSI peptide for 5 days. Cells positive for CD8+, CD44$^{HI}$ and CD62L$^{LOW}$ markers were then evaluated for CFSE by four-color flow cytometry. Data represent the average values obtained from three separate experiments each containing 5 mice per treatment. Error bars reflect the standard error of the data. *$p<0.05$, $p<0.01$, *$p<0.001$, one-way ANOVA, Bonferroni/Dunn post-hoc analysis.

The T Cell Response: Memory—Antigen-specific CD8$^+$ memory T cells are crucial components of long-term protection against viral infections. In order to predict the long-term efficacy of the formulated vaccines of the invention, the inventors evaluated the effector memory CD8$^+$ T cell response with a CFSE proliferation assay. Forty-two days after immunization, splenocytes isolated from naïve mice given the unformulated vaccine contained 8.8±1.02% effector memory CD8$^+$ T cells capable of proliferating in response to an Ebola virus glycoprotein-specific MHC I-restricted peptide (FIG. 3E). The number of effector memory CD8$^+$ T cells was lower in samples harvested from animals immunized with the other formulations. Prior exposure to adenovirus significantly reduced the memory response in mice given the F3 formulation, PEGylated and unformulated vaccine. The response elicited by PLGA encapsulated vaccine was suppressed by pre-existing immunity to a lesser degree than that observed in the other treatment groups (2.32±0.09% vs. 0.85±0.08, F3 vs. 0.72±0.04, PEG).

Figure 4B:
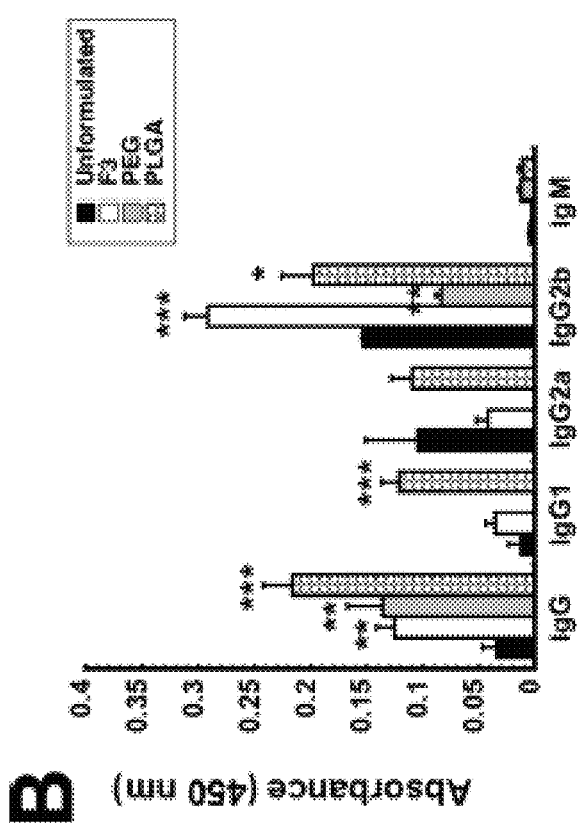
FIGS. 4A-4B: Formulated Vaccines Improve the Anti-Ebola Glycoprotein Antibody Response. Serum collected from individual mice 42 days after immunization was screened for total IgG and IgG isotypes by ELISA. (4A) Antibody Profile for Naïve Mice. Naïve B10.Br mice were given $1 \times 10^8$ particles of Ad-CAGoptZGP suspended in formulation or 4.6 mg of PLGA microspheres containing the virus in KPBS by the intranasal route. (4B) Antibody Profile for Mice with Pre-Existing Immunity to Adenovirus. Pre-existing immunity was established by instillation of a dose of $5 \times 10^{10}$ particles of AdNull in the nasal passages of B10.Br mice 28 days prior to immunization with formulated vaccines. In both panels, the average optical density read from samples obtained from each treatment group are presented to serve as a measure of relative antibody concentration and data reported as average values±the standard error of the mean obtained from three separate experiments each containing 5 mice per treatment. In each panel, the asterisk indicates a significant difference with respect to naïve, immunized animals. *$p<0.05$, $p<0.01$, *$p<0.001$, one-way ANOVA, Bonferroni/Dunn post-hoc analysis.
Figure 4A:
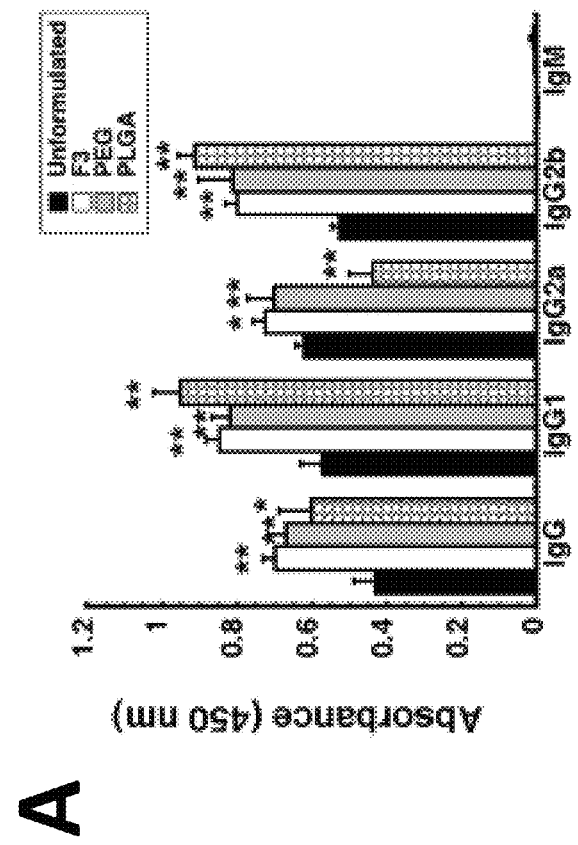

The Anti-Ebola Virus Antibody Response—The inventors have previously found that prior exposure to adenovirus significantly reduced antibody-mediated immune response to Ebola glycoprotein in mice and guinea pigs (Choi et al., 2013). More specifically, the inventors also found that a reduction in glycoprotein-specific IgG1 antibodies correlated with poor survival after challenge with rodent-adapted Ebola. Thus, the inventors evaluated total anti-Ebola glycoprotein-specific immunoglobulin (IgG) and IgG isotypes in serum to determine if each formulation could counterbalance the effect of prior mucosal exposure to adenovirus on B cell-mediated immune responses (FIGS. 4A-4B). Each formulation significantly increased the amount of each antibody isotype specific for Ebola glycoprotein (GP) in naïve mice (FIG. 4A). IgG2a levels in mice given PLGA microspheres was the only deviation from this trend as it was reduced by 29.9% with respect to unformulated virus (FIG. 4A). Prior exposure to adenovirus significantly reduced each anti-Ebola GP-specific IgG isotype evaluated (FIG. 4B). Although IgG2b levels in samples collected from mice immunized with the F3 formulation doubled, IgG1 and IgG2a levels were not significantly different from that seen in animals given unformulated virus. IgG1 and IgG2b levels in mice immunized with PLGA microspheres were 9.5 and 1.3 times that found in samples from mice given unformulated vaccine (FIG. 4B). PEI to adenovirus reduced IgG2b levels by 45.9% in mice given PEGylated vaccine. IgG1 and IgG2a could not be detected in serum of mice immunized with this preparation. Trace levels of Ebola GP-specific IgM antibodies were found in serum from mice given the PLGA and PEGylated preparations.

Figures 5A, 5B, 5C:
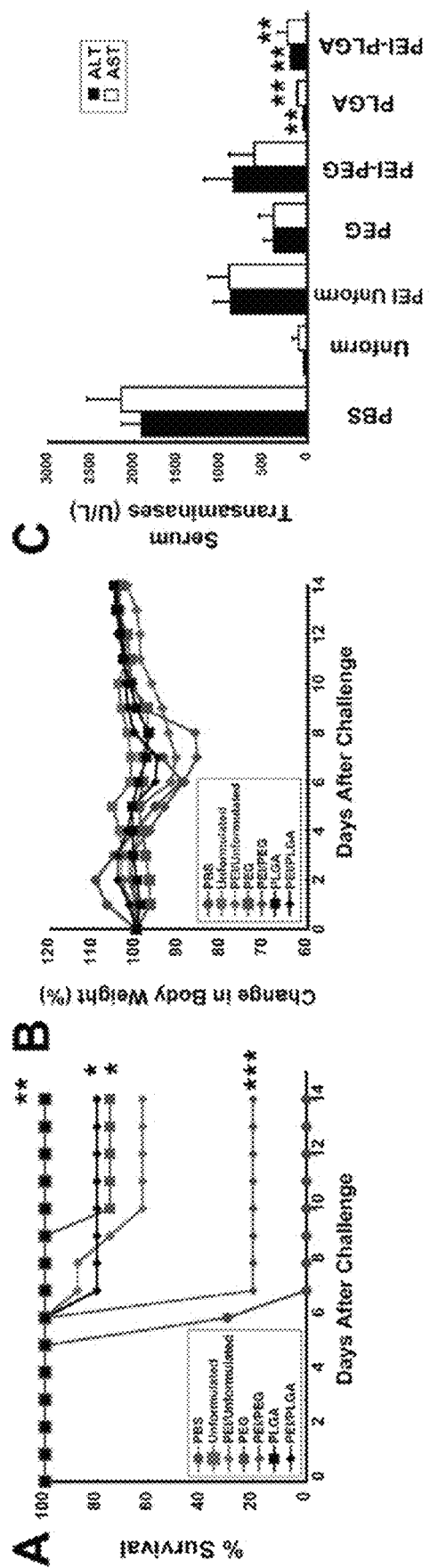
FIGS. 5A-5C: Formulations that Augment Both the Polyfunctional T cell Response and Antigen-Specific IgG1 Antibody Levels in Mice with Prior Exposure to Adenovirus Improve Survival from Lethal Challenge. Naïve B10.Br mice were given $1 \times 10^8$ particles of Ad-CAGoptZGP suspended in formulation or 4.6 mg of PLGA microspheres containing the virus in KPBS by the intranasal route. Pre-existing immunity (PEI) was established by instillation of a dose of $5 \times 10^{10}$ particles of AdNull in the nasal passages of B10.Br mice 28 days prior to immunization. Twenty eight days after immunization, mice (n=10/group) were challenged with a lethal dose of 1,000 pfu mouse-adapted Ebola ($30,000 \times LD_{50}$) by intraperitoneal injection. (5A) Kaplan-Meier survival curve. * indicates a significant difference with respect to the PEI/Unformulated treatment group. (5B) Body weight profile after challenge. No significant changes in body weight were noted in animals that survived challenge. The most significant drop in weight (~15% reduction) was observed in animals with prior exposure to adenovirus immunized with the PEGylated preparation. (5C) Serum alanine (ALT) and aspartate (AST) aminotransferase levels post-challenge. Samples from non-survivors were taken at time of death. Samples from survivors were taken 14 days post-challenge. In all panels, *p<0.05, p<0.01, *p<0.001, one-way ANOVA, Bonferroni/Dunn post-hoc analysis.

Survival From Lethal Challenge—A marked reduction in the quality of the T cell response and in Th2 type antibody responses were found to be indicative of poor protection against lethal infection with Ebola virus in animals with PEI to adenovirus (Choi et al., 2013). Using this criteria, the inventors decided that mice immunized with vaccine in formulation F3 would not be subject to challenge with a lethal dose of a mouse-adapted variant of Ebola (MA-EBOV) since neither facet of the immune response was notably improved by the formulation in mice with PEI to adenovirus. All of the naïve mice given unformulated vaccine and the PLGA microsphere preparation survived lethal challenge with MA-EBOV (1,000 pfu≅30,000× LD$_{50}$, FIG. 5A). Twenty five percent of naïve mice given the PEGylated vaccine succumbed to infection. Sixty percent of the animals with PEI to adenovirus that were immunized with unformulated vaccine survived challenge. Eighty percent of mice with prior exposure to adenovirus that were immunized with the PEGylated preparation did not survive challenge. This group also demonstrated the most notable drop in body weight during the course of infection (FIG. 5B). Samples taken from this group also revealed sharp elevations in ALT (842±342 U/L) and AST (602±298 U/L), indicative of severe liver damage from infection (FIG. 5C). The PLGA microsphere preparation protected 80% of the mice with PEI to adenovirus from challenge. Serum ALT (195±7.25 U/L) and AST (232±10.1 U/L) levels were significantly lower in this treatment group with respect to those from animals given only saline (ALT 1,913.6±228.6 U/L; AST 2,152±394.77 U/L) for which the challenge was uniformly lethal and from mice with PEI given unformulated vaccine (ALT: 879±197 U/L; AST: 898±241 U/L, p<0.01).

EXAMPLE 7

Figures 6A, 6B, 6C, 6D:
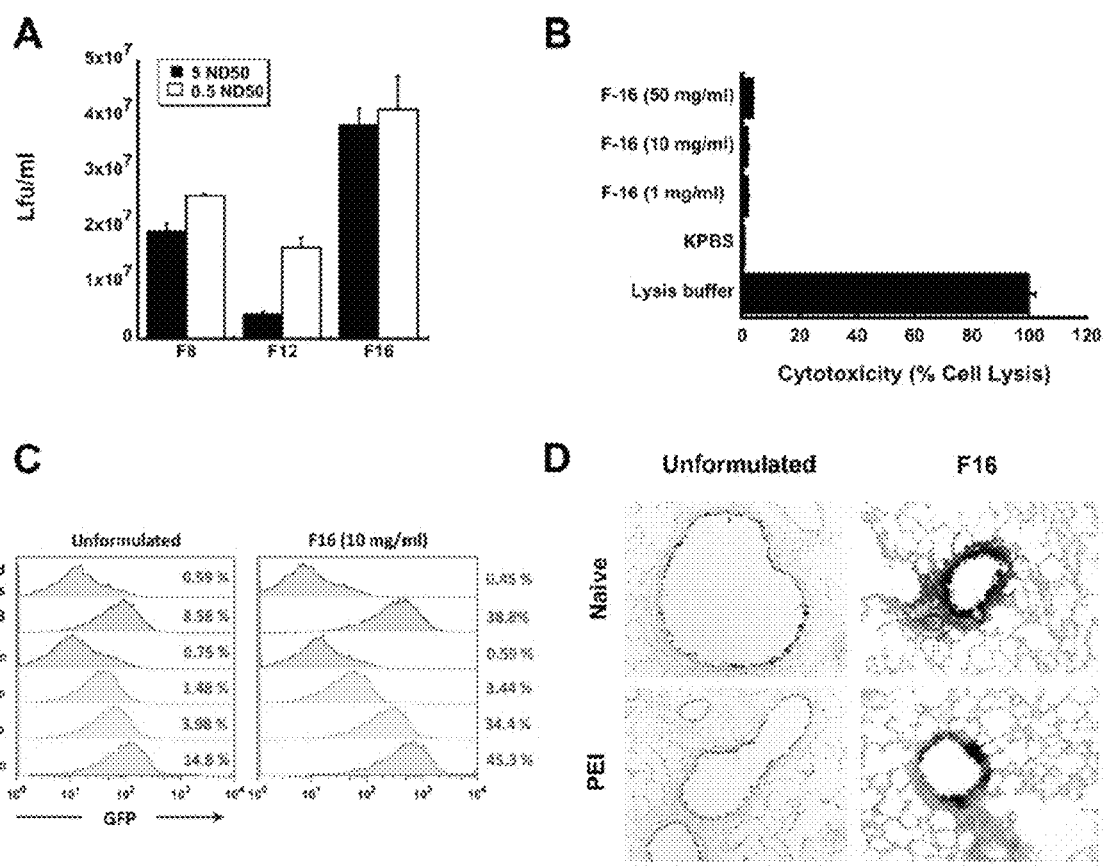
FIG. 6A-6D: Poly Maleic Anhydrides: Amphiphilic Compounds That Improve Adenovirus Transduction Efficiency with Minimal Toxicity. A series of zwitterionic polymers of varying size were screened for their ability to improve the transduction efficiency of recombinant adenoviruses in lung epithelial cells. Initial screening of formulations in vitro and in vivo was performed with AdlacZ containing the beta-galactosidase transgene (6A and 6D). Use of an E1/E3 deleted recombinant adenovirus expressing green fluorescent protein (AdGFP) and quantitation of infected cells by flow cytometry enhanced sensitivity of the screening assay so that subtle differences in transduction efficiency in the presence of anti-adenovirus neutralizing antibodies could be detected (6C). (6A) Transduction Efficiency of Formulated AdlacZ In the Presence of Neutralizing Antibody. Formulations containing $1\times10^8$ infectious particles of AdlacZ were incubated with aliquots of a highly characterized neutralizing antibody stock for 1 hour prior to infection of Calu-3 cells. Forty-eight hours later, beta-galactosidase positive cells were identified by histochemical staining. The number of infectious virus particles was tallied and calculated as described previously (Callahan et al., 2008). (6B) Toxicity Profile of F16. Formulations were placed on differentiated Calu-3 cell monolayers for a period of 2 hours. Culture media was then assessed for LDH activity. Lysis buffer served as a positive control (100% lysis) and KPBS as a negative control. (6C) Quantitative Assessment of Transduction Efficiency of Formulated AdGFP Over a Range of Neutralizing Antibody Concentrations. In this experiment, $1\times10^8$ infectious particles of AdGFP were incubated in solution containing concentrations of anti-adenovirus antibody reflective of that found in the global population (Barouch et al., 2011; Choi et al., 2012) as described in Panel A. Twenty-four hours after infection, infected cells, positive for GFP, were counted by flow cytometery. (6D) Histological Evaluation of Transgene Expression in the Lung 4 Days After Intranasal Administration of Formulated Virus. A single dose of $5\times10^{10}$ infectious particles of AdlacZ was given to naïve mice or mice with PEI to adenovirus induced by the intranasal route. Four days later, mice were sacrificed, tissue harvested and stained for transgene expression. Sections illustrate representative transgene expression patterns found in tissue collected from 6 animals per treatment. Magnification for Unformulated panels: 200×. Magnification for F16 panels: 400×. Results in FIGS. 6A-6C are reported as the mean±standard error of the mean of data generated from triplicate samples collected from four separate experiments.

An In Vitro Assay for Quantitative Evaluation of Transduction Efficiency of Formulated Virus in the Presence of Neutralizing Antibodies Because the PLGA and PEGylated preparations did not fully protect mice with PEI to adenovirus from lethal challenge, a secondary effort to identify formulations to improve survival was initiated. Based upon the initial results with the maltoside, nDMPS, the inventors sought to identify compounds with similar properties but reduced toxicity profiles for further testing. Evaluation of transduction efficiency in the presence of neutralizing antibody was also included as a more stringent test to predict in vivo performance of formulation candidates. Three different amphiphols, differing only in the length of carbon chain in the hydrophobic region of the molecule were first evaluated for their ability to preserve the transduction efficiency of the model AdlacZ vector in Calu-3 cells in the presence of neutralizing antibodies. Transduction efficiency of the virus in a formulation of 10 mg/ml of poly (Maleic Anhydride-alt-1-Decene) substituted with 3-(Dimethylamino) Propylamine (referred to as F8) was reduced from 2.58±0.03× $10^7$ to 1.94±0.14×$10^7$ ivp/ml when the anti-adenovirus 5 antibody concentration in the infection media increased from 0.5 N.D.$_{50}$ to 5 N.D.$_{50}$ (FIG. 6A). Virus formulated with 10 mg/ml poly (Maleic Anhydride-alt-1-Tetradecene) substituted with 3-(Dimethylamino) Propylamine (F12) experienced the most significant drop in transduction efficiency when antibody concentration was increased from 0.5 N.D.$_{50}$ to 5 N.D.$_{50}$ (74% reduction, 1.64±0.18×$10^7$ (0.5 N.D.$_{50}$), to 4.28±0.48×$10^6$ (5 N.D.$_{50}$) lfu/ml). Transduction efficiency of the virus formulated with 10 mg/ml poly (Maleic Anhydride-Alt-1-Octadecene) substituted with 3-(Dimethylamino) Propylamine (F16) in the presence of 5 N.D.$_{50}$ neutralizing antibody was not significantly different from that in the presence of the 0.5 N.D.$_{50}$ concentration (p=0.08, FIG. 6A). This compound also had a very favorable toxicity profile as formulations of 1 and 10 mg/ml were cytotoxic to only 1.9±0.47 and 1.8±0.61% of the Calu-3 cell population respectively (FIG. 6B). Increasing the concentration to five times that of the effective concentration (50 mg/ml) was still well tolerated by the Calu-3 cell monolayer with 3.63±0.35% lysis noted.

Before the vaccine formulated with the F16 preparation was tested in vivo, it underwent an additional round of screening to confirm that transduction efficiency was adequately improved in the presence of neutralizing antibody. In order to increase the sensitivity of this assay and make it a better predictor of in vivo performance, the inventors decided to incorporate a model a recombinant adenovirus 5 vector expressing green fluorescent protein (AdGFP) into the test formulations and evaluate transduction efficiency by fluorescence-activated cell sorting (FACS). In order to generate data that was clinically relevant, the assay was the virus was incubated with five different solutions containing a series of neutralizing antibody concentrations spanning those found in the general population[28, 41]. Cells infected with the virus were quantitated by flow cytometry 48 hours after infection. While 8.58% of the monolayer infected with unformulated virus expressed the transgene, the F16 formulation increased transduction efficiency to 38.8% (FIG. 6C). This assay allowed the inventors to see significant differences in transduction efficiency of the formulated virus in the presence of the 0.5 N.D.$_{50}$ and 5 N.D.$_{50}$ antibody concentrations that was not detected by the infectious titer assay (3.44%, 0.5 N.D.$_{50}$, vs. 34.4%, 5 N.D.$_{50}$). Although the formulation improved transduction efficiency of the virus over a wide range of antibody concentrations, the limit of this improvement was reached at the 50 N.D.$_{50}$ concentration where the formulation could no longer protect the virus from neutralization.

Adenovirus formulated with the F16 compound was well tolerated in naïve animals and those with PEI to adenovirus. Almost every epithelial cell in both large and small airways was transduced by virus formulated with F16 (FIG. 6D). Highly concentrated areas of transgene expression were also found in small airways of mice with circulating neutralizing antibody levels of 262±43 reciprocal dilution given virus in this formulation. In contrast, PEI to adenovirus prevented transgene expression in both large and small airways of mice given unformulated virus. Serum transaminases, standard indicators of adenovirus toxicity[42], in both naïve animals and those with PEI to adenovirus immunized with the F16 formulation were reduced by 40% with respect to similar treatment groups given unformulated vaccine (data not shown).

EXAMPLE 8

Figures 7A, 7B, 7C:
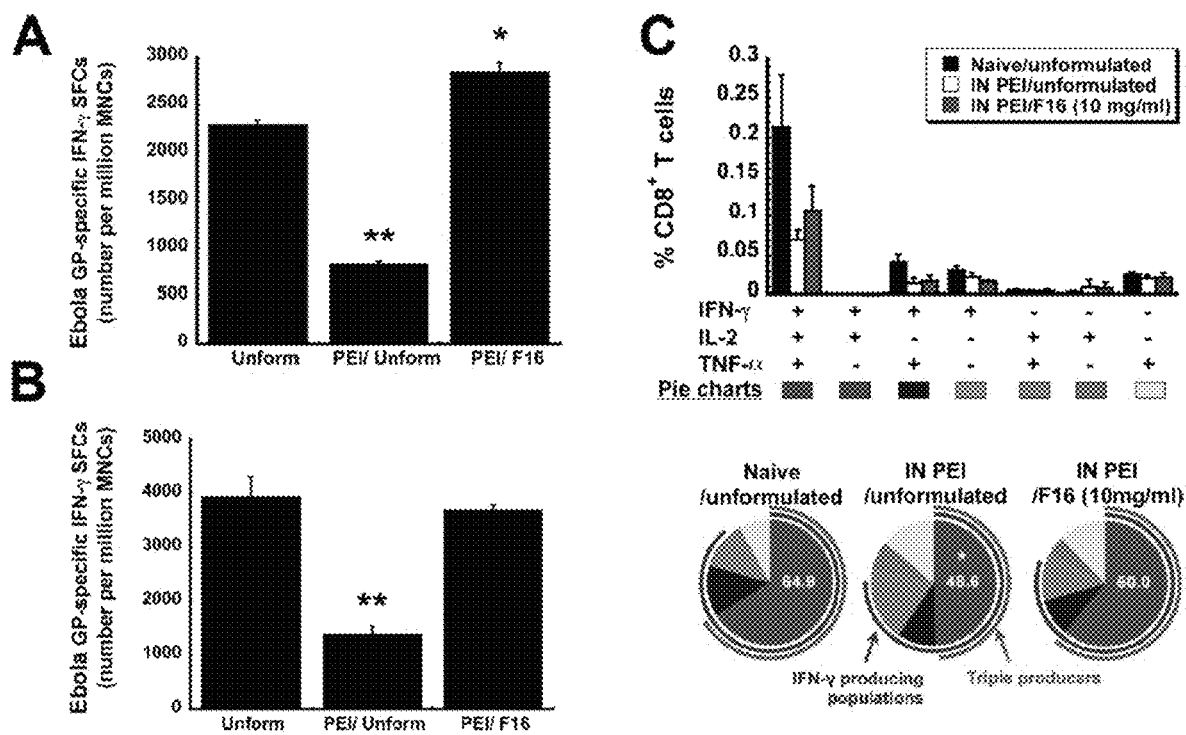
FIGS. 7A-7C: Formulation F16 Improves Quantitative and Qualitative Ebola Glycoprotein-Specific CD8+ T Cell Responses in Mice with Prior Exposure to Adenovirus. PEI to adenovirus 5 was induced by instilling $5\times10^{10}$ virus particles of AdNull, an E1/E3 deleted virus that does not contain a transgene cassette, in the nasal cavity of mice 28 days prior to immunization. (7A) The Systemic Effector CD8+ T Cell Response. Ten days after vaccination, mononuclear cells from the spleen were harvested, stimulated with an Ebola GP-specific peptide and responsive cells quantitated by ELISpot. (7B) The Mucosal Effector CD8+ T Cell Response. Ten days after vaccination, mononuclear cells collected from BAL fluid were harvested, pooled according to treatment, stimulated with an Ebola GP-specific peptide and responsive cells quantitated by ELISpot. (7C) The Polyfunctional CD8+ T Cell Response. Ten days after immunization, splenocytes from 5 mice per treatment group were pooled and stimulated with an Ebola glycoprotein-specific peptide. Each positively responding cell was assigned to one of 7 possible combinations of IFN-γ, IL-2 and TNF-α production and quantitated as shown in the bar graph. The most potent responders, those producing all 3 cytokines in response to stimulation, are depicted by the red arcs in the pie charts. The proportion of cells in samples from each treatment group that produce IFN-γ is depicted by the blue arc. The number in each pie chart denotes the percentage of triple producers found in samples from a given treatment group. Data reflect average values±the standard error of the mean for six mice per group. *indicates a significant difference with respect to the Naive/unformulated group, *p<0.05, **p<0.01, one-way ANOVA, Bonferroni/Dunn post-hoc analysis.

The Immune Response Generated by Formulation F16 in Mice with Pre-Existing Immunity Because prior formulation candidates did not fully confer protection in mice in which PEI was established through the nasal mucosa, evaluation of the F16 formulation in vivo focused solely on the ability of this formulation to improve the immune response to the encoded Ebola glycoprotein under these specific conditions. As seen in prior studies, PEI significantly compromised the production of GP-specific IFN-γ-secreting mononuclear cells isolated from spleen (FIG. 7A) and BAL fluid (FIG. 7B) in animals given unformulated vaccine (p<0.01). PEI induced by the mucosal route also significantly reduced the frequency of GP-specific multifunctional CD8$^+$ T cells elicited by the unformulated vaccine (Naïve: 64.9±4.88% vs. IN PEI/Unformulated: 48.6±3.66%, p<0.05; FIG. 7C).

Figure 8:
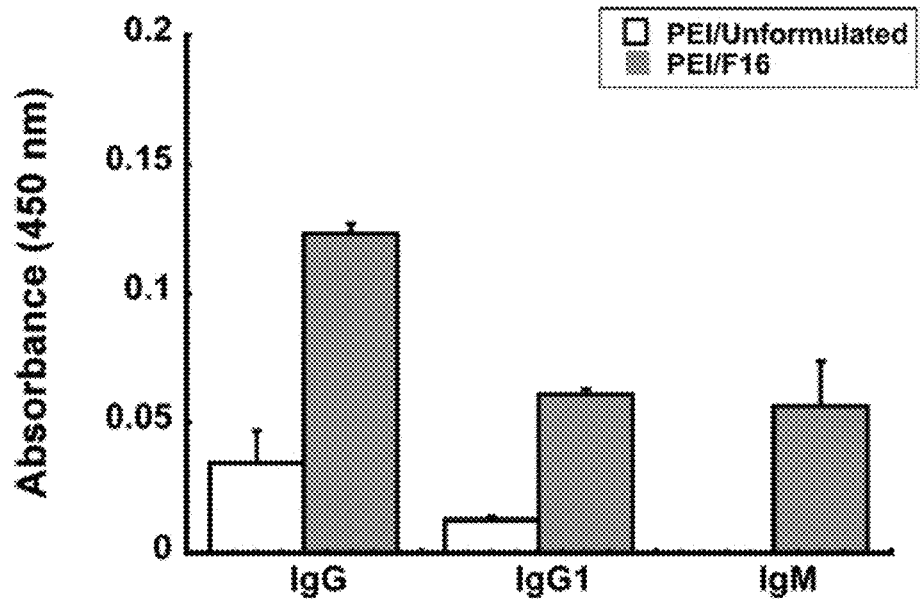
FIG. 8: Formulation F16 Improves the Antigen Specific Antibody Response in Mice with Prior Exposure to Adenovirus. The average optical density read from individual samples obtained from each treatment group are presented to serve as a measure of relative antibody concentration and data reported as average values±the standard error of the mean obtained from two separate experiments each containing 6 mice per treatment. The limit of detection for the assay is 0.01 absorbance unit. **p<0.01, one-way ANOVA, Bonferroni/Dunn post-hoc analysis.
Figure 9:
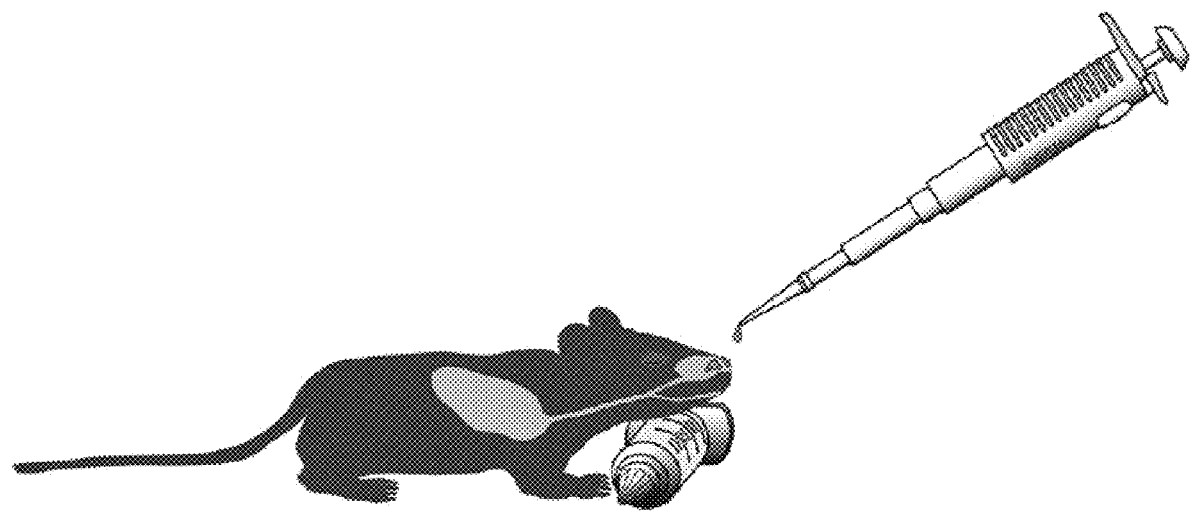
FIG. 9: Schematic illustration of vaccination process for liquid formulations and/or those reconstituted from a solid matrix. The sedate animal's head was rested upon an empty tuberculin syringe to keep the head in an upright position and to minimize choking or accidental swallowing of vaccine.

The F16 formulation improved the immune response in animals with PEI to adenovirus as the number of GP-specific, IFN-γ-secreting mononuclear cells isolated from the spleen of these animals was notably higher than that from naïve animals given unformulated vaccine (2,290±51 SFCs/million MNCs, naïve vs. 2,840±110 SFCs/million MNCs, PEI/F16,p<0.05, FIG. 7A). The number of antigen-specific IFN-γ-secreting mononuclear cells isolated from the BAL fluid of animals given the F16 formulation was not statistically different from that found in naïve animals given unformulated vaccine (p=0.07, FIG. 7B). This trend was also observed with respect to the multifunctional CD8$^+$ T cell response as it also did not change with respect to that found in naïve animals given unformulated vaccine (Naïve/unformulated: 64.9±4.88% vs. IN PEI/F16 (10 mg/ml): 60.0±9.1%, p=0.055; FIG. 7C). Forty-two days after immunization, the effector memory CD8$^+$ T cell response was also evaluated in mice immunized with unformulated vaccine or the F16 preparation. The F16 formulation increased the memory response by a factor of 3.3 from 0.28±0.15% (unformulated) to 0.93±0.25% (F16, data not shown). Serum from animals with pre-existing immunity to adenovirus that were immunized with the F16 preparation contained 4 times more anti-Ebola glycoprotein antibodies than that from animals given unformulated vaccine (FIG. 8). Samples from these animals also contained 5 times more of the IgG1 isotype and notable levels of antigen-specific IgM antibodies.

EXAMPLE 9

Materials and Methods for Primate Studies (Examples 10-11) Adenovirus Production The E1/E3 deleted recombinant adenovirus serotype 5 vector expressing a codon optimized full-length Ebola glycoprotein sequence under the control of the chicken β-actin promoter (Ad-CAGoptZGP) and a host range mutant adenovirus serotype 5 (Ad5MUT) that can replicate in non-human primates were amplified in HEK 293 cells and purified as described (Richardson et al., 2009; Buge et al., 1997).

Concentration of each virus preparation was determined by UV spectrophotometric analysis at 260 nm and with the Adeno-X Rapid Titer Kit (Clontech, Mountain View, Calif.) according to the manufacturer's instructions. Preparations with infectious to physical particle ratios of 1:37 were used in these studies. Buffers and reagents used in the production and purification of each virus preparation were of the highest quality available and were tested for the presence of endotoxin using a QCL-1000 Chromogenic LAL end point assay (Cambrex Bioscience, Walkersville, Md.). All reagents contained less than 0.1 E.U./mL, and each virus preparation contained less than 0.2 E.U./mL. Sterility of each preparation was confirmed employing the methods outlined in the United States Pharmacopeia for parenteral products.(Sterility Tests. In the United States Pharm., 2014)

Assay for Detection of Replication Competent Adenovirus (RCA)

A two cell line bioassay was performed on each preparation to determine the presence of RCA as described (Gilbert el al., 2014). Less than one RCA was detected for every $3 \times 10^{12}$ virus particles tested.

Animal Model

Non-human primate studies were conducted under a contract at Bioqual Inc., Gaithersburg, Md. The animal management program of this institution is accredited by the American Association for the Accreditation of Laboratory Animal Care and meets NIH standards as outlined in the Guide for the Care and Use of Laboratory Animals. This institution also accepts as mandatory PHS policy on Humane Care of Vertebrate Animals used in testing, research, and training. Twenty male cynomolgus macaques (*Macaca fascicularis*) of Chinese origin were allowed to acclimate for 30 days in quarantine prior to immunization. Animals received standard monkey chow, treats, vegetables, and fruits throughout the study. Husbandry enrichment consisted of commercial toys and visual stimulation. Two separate experiments were conducted as summarized in FIGS. 10 and 16A-16B. Specific details about the primates used in each of these studies are summarized in Tables 1 and 2.

TABLE 1

Primate Study 1: Primate Characteristics and Treatment

| animal no. | treatment | wt (kg) | dose (ivp/kg) | route of admin | age (years) |
|---|---|---|---|---|---|
| 22457 | KPBS | 8.05 | | IM | 10 |
| 22473 | Ad-CAGoptZGP | 6.36 | $1.6 \times 10^8$ | IM | 10 |
| 40347 | Ad-CAGoptZGP | 6.16 | $1.6 \times 10^8$ | IM | 8 |
| 50459 | Ad-CAGoptZGP | 7.31 | $1.4 \times 1.0^9$ | IN/IT | 7 |
| 52483 | Ad-CAGoptZGP | 6.98 | $1.4 \times 10^9$ | IN/IT | 7 |
| 52945 | Ad-CAGoptZGP | 6.84 | $1.5 \times 10^9$ | IN/IT | 7 |
| 52165 | Ad-CAGoptZGP | 6.30 | $1.6 \times 10^9$ | SL | 7 |
| 62125 | Ad-CAGoptZGP | 5.59 | $1.8 \times 10^9$ | SL | 6 |
| 62361 | Ad-CAGoptZGP | 6.38 | $1.6 \times 10^9$ | SL | 6 |

TABLE 2

Primate Study 2: Primate Characteristics and Treatment

| animal no. | treatment | wt (kg) | dose (ivp/kg) | route of admin | age (years) |
|---|---|---|---|---|---|
| 0810091 | KPBS | 8.7 | | IM | 6 |
| 0805201 | KPBS | 6.8 | | IM | 6 |
| 0802197 | Ad-CAGoptZGP | 6.2 | $1.6 \times 10^9$ | IN/IT | 6 |
| 0809077 | Ad-CAGoptZGP | 6.5 | $1.5 \times 10^9$ | IN/IT | |
| 0810003 | Ad-CAGoptZGP | 5.8 | $1.7 \times 10^9$ | IN/IT | |
| 0805257 | Ad-CAGoptZGP | 4.9 | $2.0 \times 10^{10}$ | SL | |
| 0804317 | Ad-CAGoptZGP | 4.8 | $2.0 \times 10^{10}$ | SL | 6 |
| 0808233 | Ad-CAGoptZGP | 4.8 | $2.0 \times 10^{10}$ | SL | 6 |
| 0809227 | Ad5MUT Ad-CAGoptZGP | 5.5 | $1.8 \times 10^{10}$ $1.8 \times 10^{10}$ | IM SL | 6 |
| 0804819 | Ad-5MUT Ad-CAGoptZGP | 5.2 | $1.9 \times 10^{10}$ $1.9 \times 10^{10}$ | IM SL | |
| 0807243 | Ad5MUT Ad-CAGoptZGP | 4.9 | $2 \times 10^{10}$ $2 \times 10^{10}$ | IM SL | 6 |

Primate Study 1 (Results Shown in Example 10)

The first study was conducted with 9 primates. Two animals were given the vaccine by intramuscular injection in a total volume of 1 mL of potassium phosphate buffered saline (KPBS) divided equally between the left and right deltoid muscles. Three animals were given the vaccine by the sublingual route by placing 50 μL of the preparation under each side of the tongue and waiting for 15 min between doses to allow for absorption. Three animals were given the vaccine in the respiratory tract. This was achieved by slowly dispensing two 250 μL volumes of the preparation into each nostril and waiting for 15 min between doses to allow for absorption. The remaining dose of the vaccine (5 mL volume) was instilled into the lungs via an endotracheal tube. This route of administration will be referred to as respiratory immunization or as intranasal/intratracheal (IN/IT) throughout the manuscript to illustrate that the vaccine was administered to the respiratory mucosa by two different routes. One primate was given 1 mL of KPBS divided equally between the left and right deltoid muscles. This animal was the negative control. Blood was collected 6 h after immunization and on days 1, 2, and 7. Full blood chemistry panels and complete blood counts were performed by IDEXX BioResearch (West Sacramento, Calif.).

Primate Study 2 (Results Shown in Example 11)

A second study was conducted with 11 primates. Two animals (negative controls) were given 1 mL each of KPBS divided between the left and right deltoid muscles. The respiratory formulation contained sucrose (10 mg/ml), mannitol (40 mg/ml) and 10 mg/mL poly(maleic anhydride-alt-1-octadecene) substituted with 3-(dimethylamino)propylamine and administered as a solution to the respiratory mucosa of three animals as described for study 1. Three animals were given an adenovirus serotype 5 host range mutant virus to establish pre-existing immunity (PEI) by IM injection 28 days prior to immunization with the vaccine by the sublingual route as described above. Three animals with no prior exposure to adenovirus were given the vaccine by the sublingual route for comparison.

Challenge

Animals were transported to the National Microbiology Laboratory in Winnipeg and, after an acclimation period, transferred to the biosafety level 4 (BSL-4) laboratory there for challenge. Challenge studies were approved by the Canadian Science Centre for Human and Animal Health (CSCHAH) Animal Care Committee following the Guidelines of the Canadian Council on Animal Care. For challenge, animals were infected by intramuscular injection at two sites with a total volume of 1 mL of freshly prepared Ebola virus (strain Kikwit 95, passage 3 on VeroE6 cells) of an inoculum containing 1,000 times the 50% tissue culture infectious dose (TCID50) in diluent (minimal essential medium containing 0.3% bovine serum albumin). Ebola virus titers were confirmed ($1.21 \times 10^3$ TCID50/mL) by back-titration of the challenge preparation following administration of the virus. Animals were monitored daily and scored for disease progression using an internal filovirus scoring protocol approved by the CSCHAH Animal Care Committee. The scoring system graded changes from normal in the subject's posture, attitude, activity level, feces/urine output, food/water intake, weight, temperature, and respiration and ranked disease manifestations such as a visible rash, hemorrhage, cyanosis, or flushed skin. Samples were taken for assessment of anti-Ebola GP antibodies and full blood panels on days 3, 7, 14, 21, and 28 postchallenge and upon death. Hematological analysis of samples was performed in the BSL-4 lab with a Horiba ABX Scil ABC Vet Animal Blood Counter, and blood chemistries were analyzed with a VetScan vs1 (Abraxis). Surviving animals were kept until day 28.

ELISpot Assay

TFN-γ ELISpot assays were performed in triplicate according to the manufacturer's protocol (BD Biosciences, San Diego, Calif.) with $5 \times 10^5$ peripheral blood mononuclear cells (PBMCs) per well in cRPMI media (RPMI 1640, 1 mM 1-glutamine, 50 μM β-mercaptoethanol, 10% FBS and 1% penicillin/streptomycin). Cells were stimulated with three peptide pools for the Ebola glycoprotein (2.5 μg/mL) for 18 h. Spots were visualized with the AEC substrate (BD Biosciences) and quantified with the ELISpot Plate Reader (AID Cell Technology, Strassberg, Germany).

Intracellular Cytokine Staining

PBMCs were isolated from whole blood collected prior to challenge as described (Qiu et al., 2013). The frequency of CD8+ and CD4+ T cells producing IFN-7, IL-2, IL-4, and CD107a were assessed by flow cytometry with the following antibodies: CD3 Alexa Fluor 700 (clone SP34-2) and CD4 Peridinin Chlorophyll Protein (PerCP)-Cy5.5 (clone L200) from BD Biosciences (San Jose, Calif.); CD8 phycoerythrin (PE)-Cy7 (clone RPA-T8), CD107a Brilliant Violet 421 (clone H4A3), IL-2 Alexa Fluor 488 (clone MQ1-17h12), IL-4 PE (clone 8D4-8), and IFN-γ Allophycocyanin (APC, clone B27) from BioLegend (San Diego, Calif.). One million PBMCs were stimulated overnight with peptides (5 μg/mL) using GolgiPlug (0.5 μL/mL) and GolgiStop (0.6 μL/mL) in the presence of the anti-CD107a antibody. After surface staining for CD3, CD4, and CD8, samples were incubated two times (30 min each) in Cytofix/Cytoperm (BD Biosciences) for permeabilization. Intracellular staining was performed, and the samples were kept overnight in PBS/1% paraformaldehyde. Approximately 250,000-500,000 events were captured on a BD LSR II flow cytometer and data analyzed with FlowJo vX0.6 software (Tree Star, Ashland, Oreg.).

Measurement of Proliferative Responses by Ki-67 Staining

Blood was collected from each primate in EDTA tubes, shipped same day and PBMCs isolated as described previously (Hokey et al., 2008). Cells were resuspended in R10 medium (RPMI 1640, 2 mM 1-glutamine, 50 μM β-mercaptoethanol, 10% FBS, and 100 IU/mL penicillin and streptomycin) and stimulated using either an Ebola glycoprotein-specific peptide library (2.5 μg/mL), a first generation adenovirus that is genetically identical to the vaccine but does not contain a transgene cassette (AdNull, 1,000 MOI), (22) or 5 μg/mL ConA (Sigma, St. Louis, Mo.) for 5 days in 5% CO2 at 37° C. After 3 days, cells were fed by removing 50 μL of spent medium and replacing it with 100 μL of fresh R10 medium. On day 5, cells were washed with phosphate buffered saline (PBS) for subsequent immunostaining for cell surface markers and for Ki-67, an intracellular marker for proliferation as described (Shedlock et al., 2010). Proliferation was calculated by subtraction of values obtained from cells cultured in medium alone.

Anti-Ebola Glycoprotein Antibody ELISA

Flat bottom, Immulon 2HB plates (Fisher Scientific, Pittsburgh, Pa.) were coated with purified Ebola virus GP33-637 ΔTM-HA (3 μg/well) in PBS (pH 7.4) overnight at 4° C. (Lee et al., 2009). Heat-inactivated serum samples were diluted (1:20) in saline. One hundred microliters of each dilution were added to antigen-coated plates for 2 h at room temperature. Plates were washed 4 times and incubated with a HRP-conjugated goat anti-monkey IgG antibody (1:2,000, KPL, Inc., Gaithersburg, Md.) for 1 h at room temperature. Plates were washed and substrate solution added to each well. Optical densities were read at 450 nm on a microplate reader (Tecan USA, Research Triangle Park, NC).

Neutralizing Antibody Assays

Ebola Virus

Primate sera were heat inactivated at 56° C. for 45 min and then serially diluted in 2-fold increments in Dulbecco's modified Eagle's medium (DMEM) in triplicate prior to incubation at 37° C. for 1 h with an equal volume of medium containing EBOV-eGFP (100 PFU per well) as described (Qiu et al., 2012). Virus-serum mixtures were then added to Vero E6 cells and placed at 37° C. for 2 days and then fixed in 10% phosphate buffered formalin. GFP levels were quantified by a fluorescent plate reader (AID Cell Technology). These assays were performed under BSL-4 conditions at the National Microbiology Laboratory in Winnipeg.

Adenovirus

Primate sera were heat inactivated and serially diluted as described for the Ebola virus assay. Samples were incubated with a first generation adenovirus serotype 5 expressing beta-galactosidase for 1 h before they were added to HeLa cell monolayers. An equal volume of medium containing 20% FBS was then added to each well, and infections continued for 24 h. Cells were then histochemically stained for beta-galactosidase expression as described (Choi et al., 2012). Positive cells were quantified by visual inspection with a Lecia DM LB microscope (Leica Microsystems Inc., Bannockburn, Ill.). For both assays, the serum dilution that corresponded to a 50% reduction in transgene expression was calculated by the method of Reed and Muench and reported as the reciprocal of this dilution (Reed et al., 1938).

Quantification of Virus Genomes by Real Time PCR

Ebola Virus

Total RNA was extracted from whole blood using a QIAmp Viral RNA Mini Kit (Qiagen). Ebola virus RNA was detected by a qRT-PCR assay targeting the RNA polymerase (nucleotides 16472 to 16538, AF086833) and LightCycler 480 RNA Master Hydrolysis Probes (Roche Diagnostics GmbH, Mannheim, Germany). The reaction conditions were as follows: 63° C. for 3 min, 95° C. for 30 s, and cycling of 95° C. for 15 s, 60° C. for 30 s for 45 cycles with a LightCycler 480 II (Roche). Primer sequences for this assay were as follows: EBOVLF2 CAGCCAGCAATTTCTTC-CAT (SEQ ID NO: 3), EBOVLR2 TTTCGGTTGCTGTTTCTGTG (SEQ ID NO: 4), and EBOVLP2FAM FAM-ATCATTGGCGTACTGGAG-GAGCAG-BHQ1 (SEQ ID NO: 5).

Adenovirus

Urine and BAL fluid were concentrated using Amicon Ultra 100K Centrifugal Filter Devices (Millipore, Billerica, Mass.). DNA was isolated from blood, concentrated BAL, and oral and nasal swabs using a QIAmp DNA Mini kit according to the manufacturer's instructions (Qiagen, Valencia, Calif.). DNA was isolated from rectal swabs using a modified protocol and the QIAmp DNA Mini kit. DNA was extracted from the urine concentrate using a QIAamp Viral RNA mini kit (Qiagen) according to the manufacturer's instructions. DNA was isolated from stool samples using a QIAamp Fast DNA Stool Mini kit (Qiagen). Quantification of viral DNA was determined by real time PCR according to a published protocol (Callahan et al., 2006). DNA amplifications were carried out using a ViiA 7 Real-Time PCR System (Life Technologies, Carlsbad, Calif.) with the following cycling conditions: 50° C. for 2 min, 95° C. for 10 min, 95° C. for 15 s, and 62° C. for 1 min for a total of 41 cycles. Primer sequences, used to amplify a region of the adenovirus serotype 5 hexon protein, were 5'-ACT ATA TGG ACA ACG TCA ACC CAT T-3' (forward; SEQ ID NO: 6) and 5'-ACC TTC TGA GGC ACC TGG ATG T-3' (reverse; SEQ ID NO: 7). The internal probe sequence, tagged with 6FAM fluorescence dye at the 5' end and TAMRA quencher at the 3' end, was 5'-ACC ACC GCA ATG CTG GCC TGC-3' (SEQ ID NO: 8). Each sample was run in triplicate in a given PCR assay.

EXAMPLE 10

Results of Primate Study 1

Figure 10:
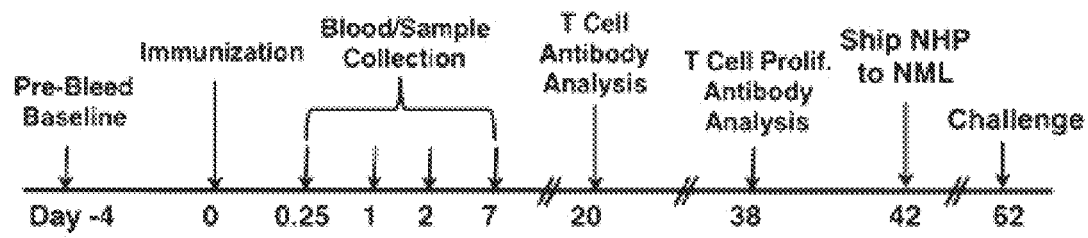
FIG. 10: Timeline and sampling schedule for primate Study 1. Animals were screened for signs of prior exposure to adenovirus (anti-Ad5 NAB, Ad5 DNA, T cell responses) 4 days prior to immunization. Baseline blood chemistry panels were also evaluated at this time. Samples were taken for evaluation of blood chemistry and adenovirus shedding (nasal and oral swabs, urine, feces) 6 h after immunization and on days 1, 2, and 7. On day 20, serum and BAL were collected for assessment of shedding and anti-Ad5 NAB and anti-Ebola GP antibody levels. BAL, PBMCs, and ILNs were also screened for Ebola GP-specific CD8+ and CD4+ T cells at this time point. On day 38, additional samples were taken for assessment of anti-Ebola GP and anti-Ad5 antibodies and antigen-specific T cell proliferation (Ebola GP and Ad5). 42 days after immunization, NHPs were shipped to the National Microbiology Laboratory in Winnipeg, Canada, for challenge. After an acclimation period, primates were challenged with 1,000 pfu of Ebola (1995, Kikwit) by intramuscular (IM) injection.
Figure 16A:
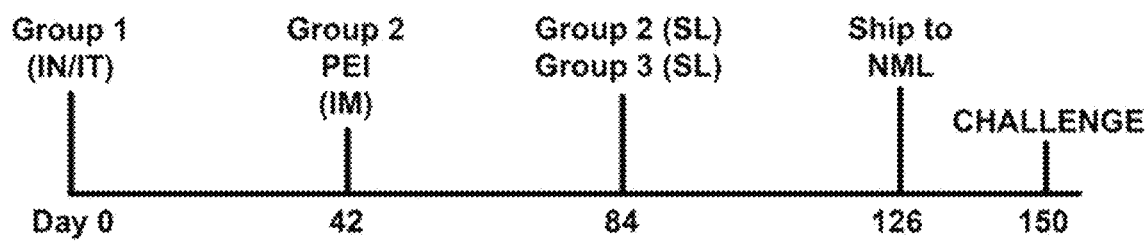
Figure 16B:
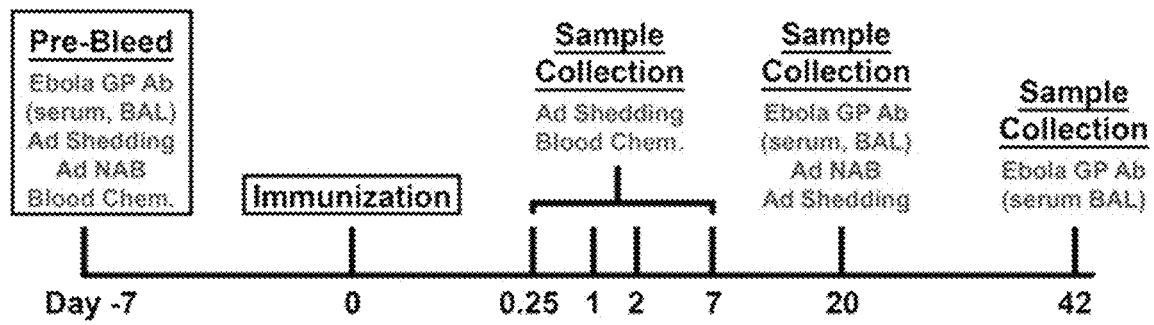
Figures 17A, 17B, 17C, 17D:
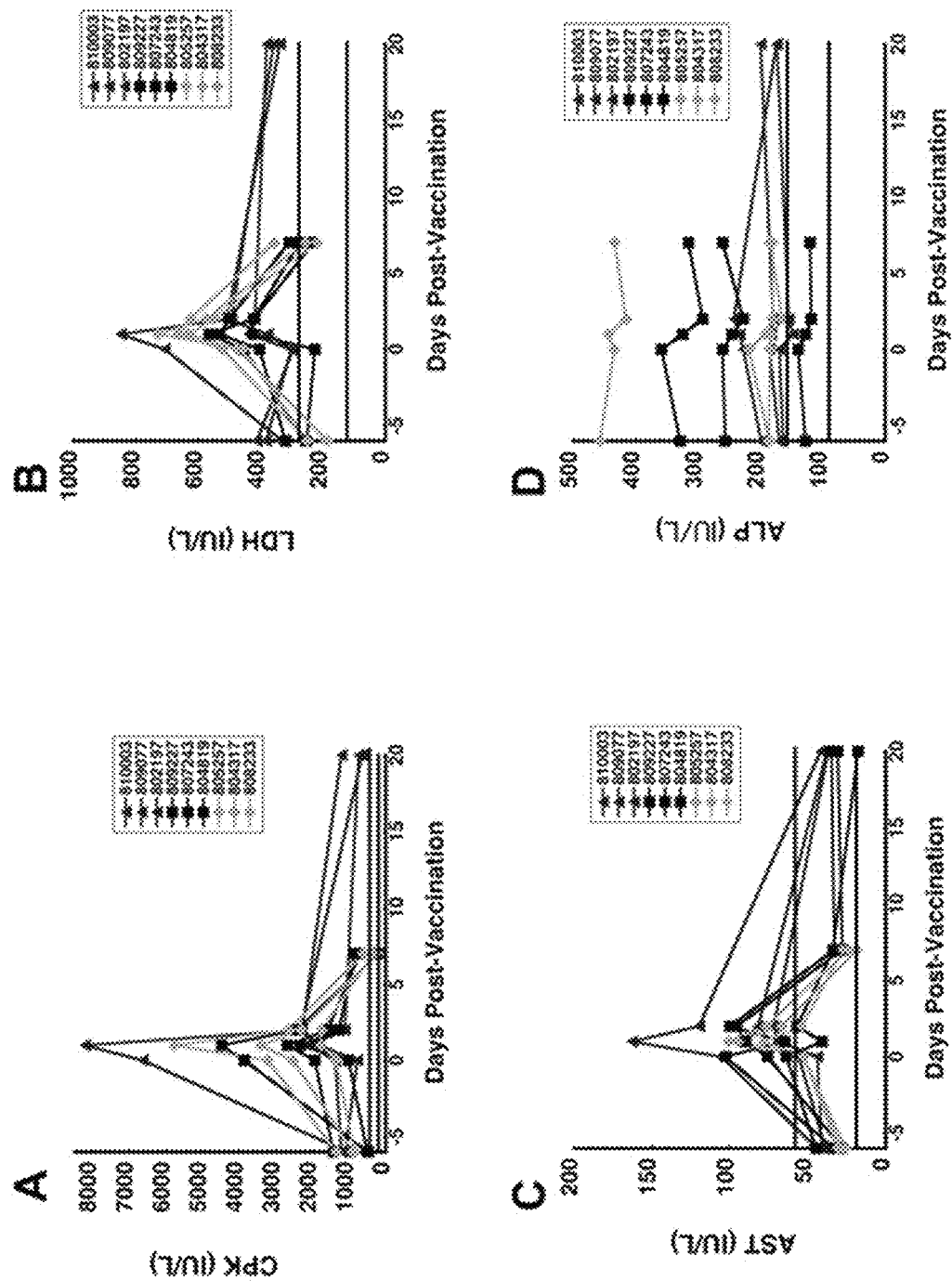
Figures 18A, 18B, 18C, 18D, 18E, 18F:
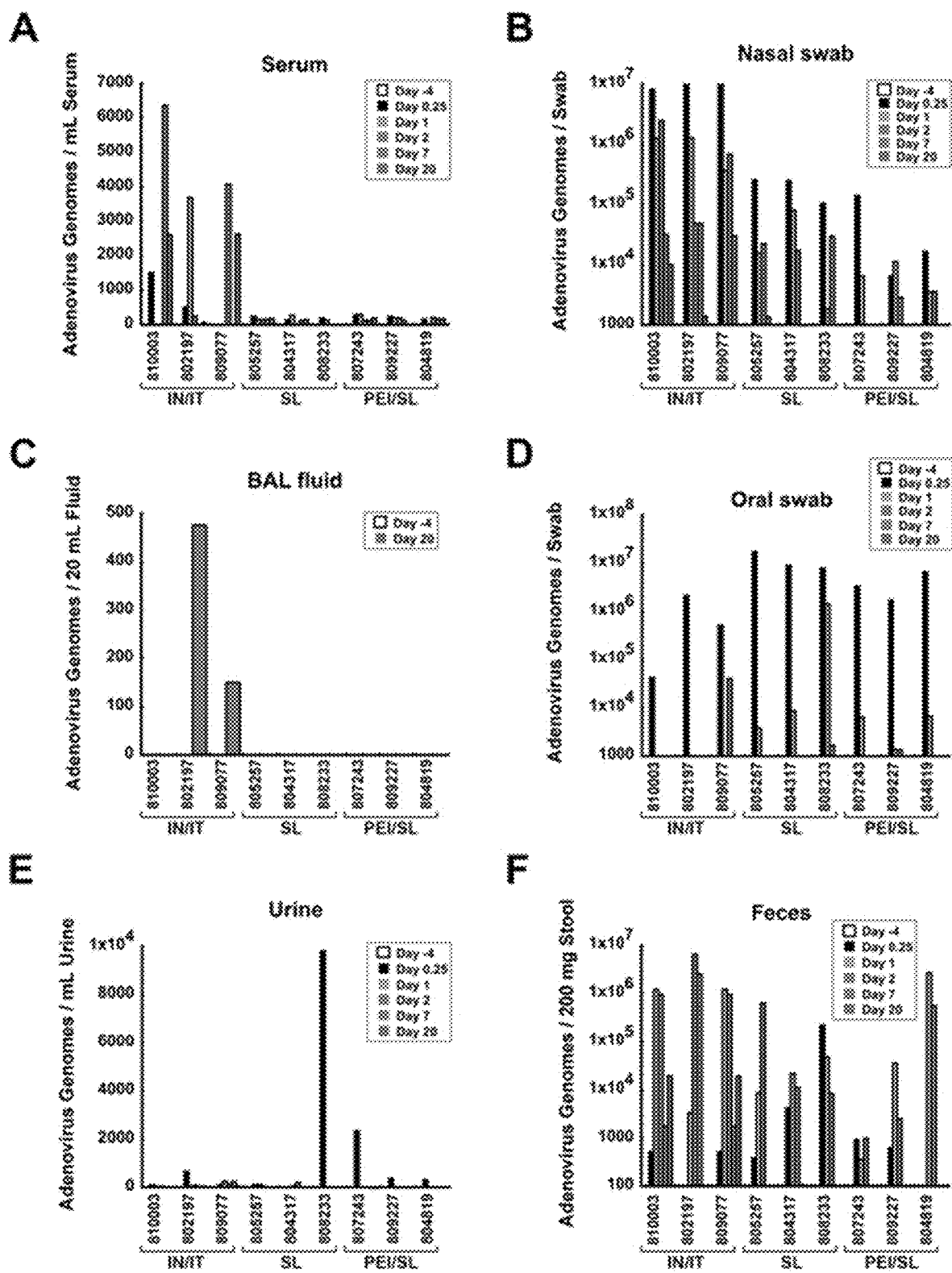

The first primate study, referred to as Primate Study 1, involved 9 male cynomolgus macaques and served to identify suitable doses of vaccine that were semiprotective for further evaluation of test formulations to improve survival in the NHP model. The workflow and treatment schedules for the study are depicted in FIGS. 10 and 16A-16B.

Figures 11A, 11B, 11C, 11D:
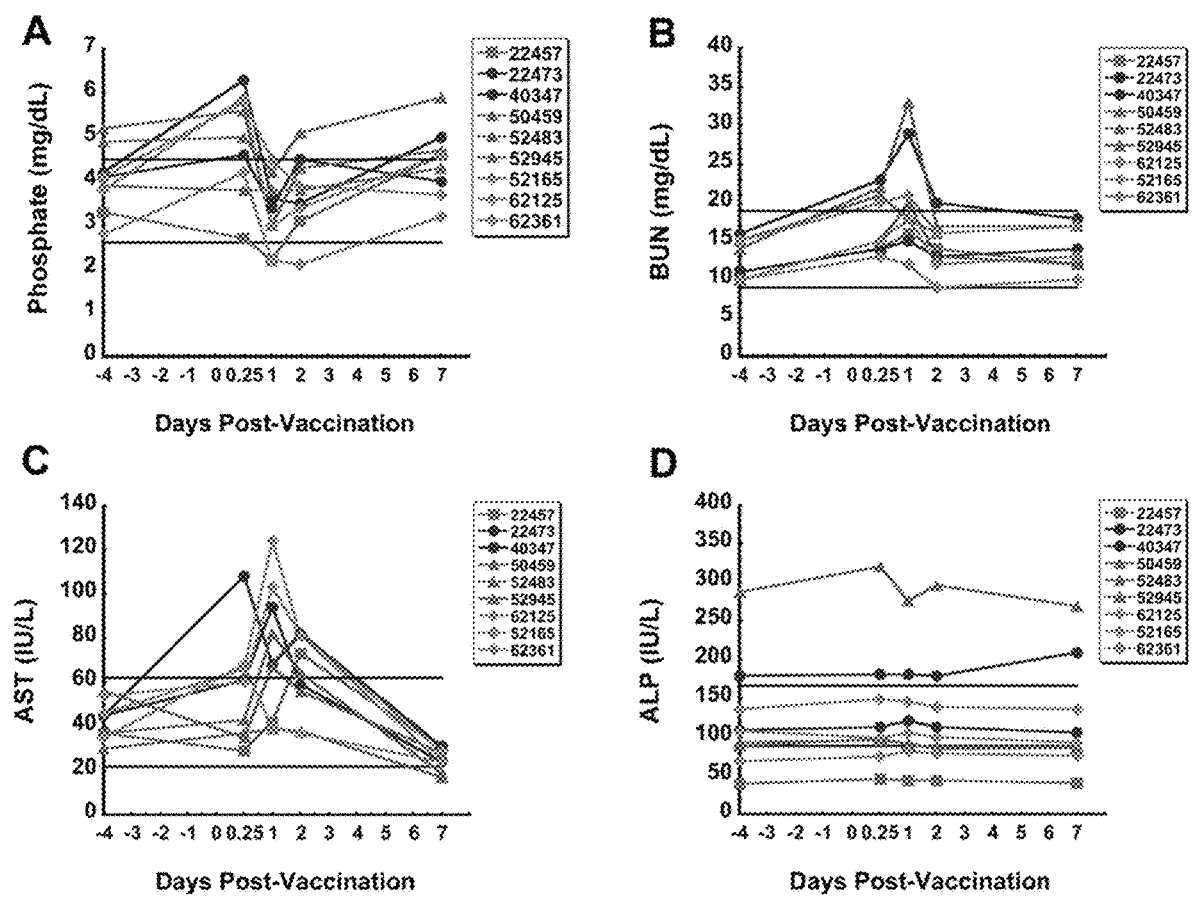
FIGS. 11A-11D: Primate Study 1: Clinical parameters evaluated over time in non-human primates immunized by various routes. Cynomolgus macaques were given a single dose of vaccine by IM injection or by the respiratory or the SL route. Each line represents alterations for each parameter during the course of therapy for one primate. In each panel: Red lines/squares: saline control. Green lines/circles: IM injection. Blue lines/triangles: IN/IT immunization. Orange lines/diamonds: SL immunization.

Administration of the vaccine at a dose of $1.4 \times 10^9$ infectious virus particles (ivp)/kg to the respiratory and the sublingual mucosa was well tolerated with no adverse reactions noted. Of particular note is that all animals experienced a transient increase in serum phosphate levels 6 h after immunization with a primate from each treatment group falling outside normal values (22473, IM, 1.4 times normal, 50459, IN/IT, 1.2 times normal, 62125, SL, 1.3 times normal, FIG. 11A). Phosphate levels for all animals reached their nadir at the 24 h time point and were within the normal range for the remainder of the study. Blood urea nitrogen (BUN) levels peaked for all animals 24 h after immunization. Two of these animals, one given the vaccine by IM injection (40347, 29 mg/dL) and another given the vaccine by the IN/IT route (52945, 33 mg/dL), had levels that were notably outside of the normal range (FIG. 11B). These values returned to normal by 48 h and remained so throughout the course of the study. Serum aspartate aminotransferase (AST), a standard indicator of adenovirus toxicity, (29) was significantly elevated above normal values in all animals 24 h after immunization except for one animal given the vaccine by the SL route (62125) and another given the vaccine by the IM route (40347). AST levels fell 48 h after immunization with only a few animals remaining above normal limits (FIG. 11C). AST values for all animals were within normal limits by the 7 day time point. Serum alkaline phosphatase (ALP) of two animals fell outside the normal range during the study. Samples from one animal given the vaccine by IM injection were only mildly over the normal acceptable limit (22473, FIG. 11D) while those of an animal immunized by the IN/IT route (52945) were 2 times the normal acceptable limit. In both cases, this parameter was high throughout the study and this elevation was not in response to the vaccine. Other serological parameters evaluated during the first week after immunization (calcium, creatinine, albumin, globulin, total protein, total bilirubin, alanine aminotransferase (ALT), glucose, sodium, potassium, chloride, and cholesterol) all fell within normal limits during the course of the study.

Figures 12A, 12B, 12C, 12D, 12E, 12F:
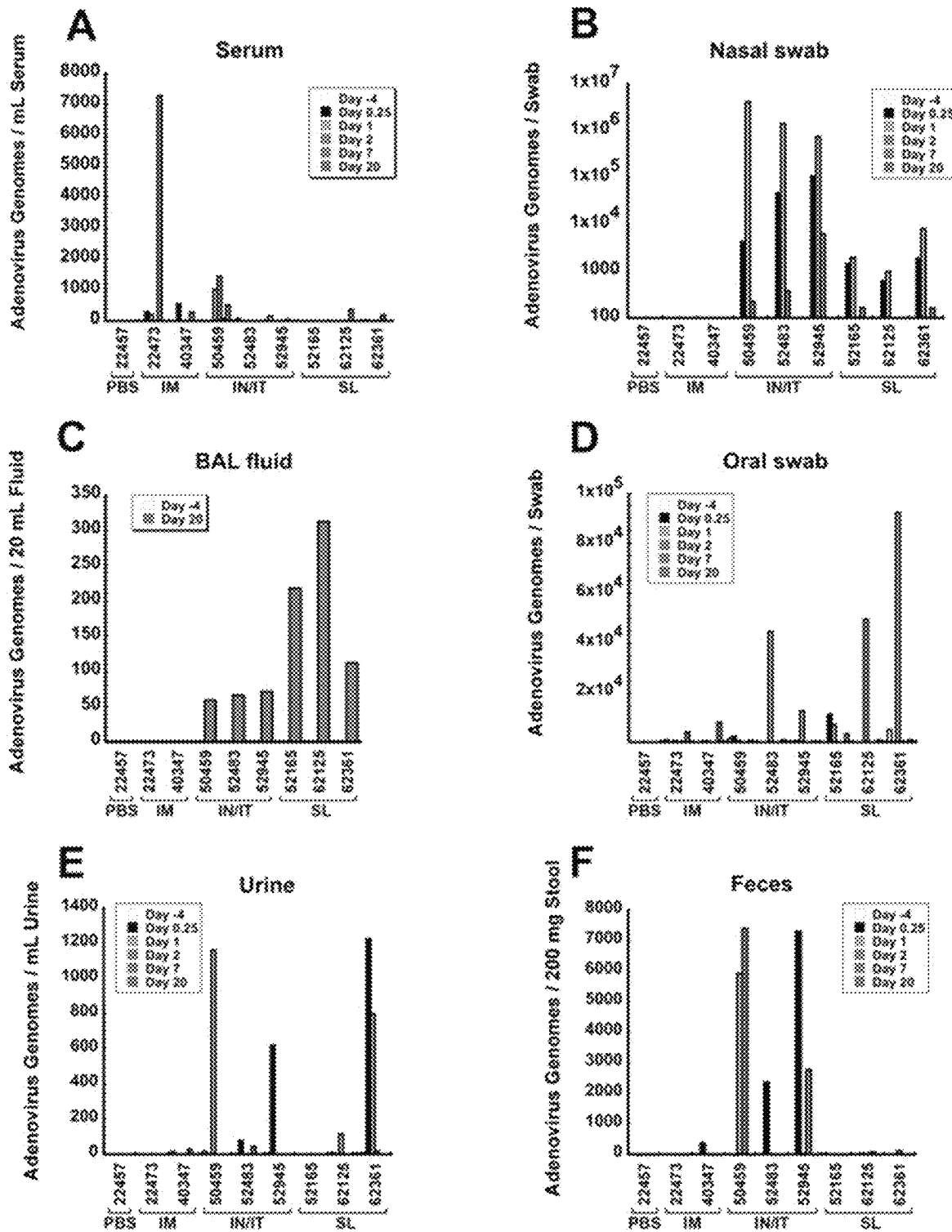
FIGS. 12A-12F: Primate Study 1: Adenovirus genomes are released predominantly in the nasal mucosa and feces after respiratory immunization and in the oral and nasal mucosa after sublingual immunization. Male cynomolgus macaques were given either $1\times10^9$ ivp by IM injection or $1\times10^{10}$ ivp by the respiratory or the SL route. DNA was isolated from each sample, and viral genomes were determined by real time PCR. Animal numbers and corresponding treatments are outlined in Table 1.

Adenovirus shedding was also evaluated using a standard real time PCR assay to detect adenovirus genomes (28) in serum, nasal swabs, BAL fluid, oral swabs, urine, and feces (FIGS. 12A-12F). A significant number of adenovirus genomes were found in the serum of one animal immunized by the respiratory route 2 days after immunization (50459, 1,452 genomes/mL serum, FIG. 12A) and another immunized by IM injection 7 days after treatment (22473, 7,296 genomes/mL serum). As expected, substantial amounts of adenovirus serotype 5 genomes were found in nasal swabs obtained from primates immunized by the IN/IT route (50459, $4.2 \times 10^6$, 52483, $1.4 \times 10^6$, 59245, $7.5 \times 10^5$) 24 h after immunization (FIG. 12B). Swabs from one primate immunized by the SL route also contained a notable amount of Ad5 genomes (62361, 8,090) at the 24 h time point. Swabs from one animal immunized by the IN/IT route contained a significant amount of adenovirus genomes 2 days after immunization (52945, 6,333). Samples taken at days 7 and 20 fell below detection limits of the assay. Very low amounts of Ad5 genomes were found in the BAL fluid of animals immunized by the IN/IT route 20 days after immunization (FIG. 12C). Oral swabs taken 24 h after treatment from one NHP immunized by the IN/IT route (52483, $4.5 \times 10^4$, FIG. 12D) and two animals immunized by the SL route (62125, $4.9 \times 10^4$, and 62361, $9.3 \times 10^4$) contained significant numbers of adenovirus genomes. Swabs collected from animals at the 2 day time point did not contain any adenovirus genomes. A significant number of virus genomes were detected in the urine of 2 animals within 6 h after treatment (52945, 621 copies/mL, and 62361, 1,228 copies/mL). Adenovirus DNA was also found 24 h after treatment in the urine of 3 animals (50459, 1,163, 62361, 801, and 62125, 116 copies/mL, FIG. 12E). Samples from all other animals throughout the time course of this study fell below detection limits of the assay. Interestingly, adenovirus genomes were only detected in the feces of animals immunized by the IN/IT route (FIG. 12F). As early as 6 h after immunization, 2,362 and 7,302 adenovirus genomes were found in fecal samples from animals 52483 and 52945 respectively. Feces collected from animal 50459 24 h after vaccination contained 5,919 adenovirus genomes. This increased to 7,405 in samples taken from the same animal at the 48 h time point. Samples from animal 52945 also taken 48 h after treatment contained 2,772 virus genomes.

The T Cell Response

Figures 13A, 13B, 13C, 13D, 13E, 13F:
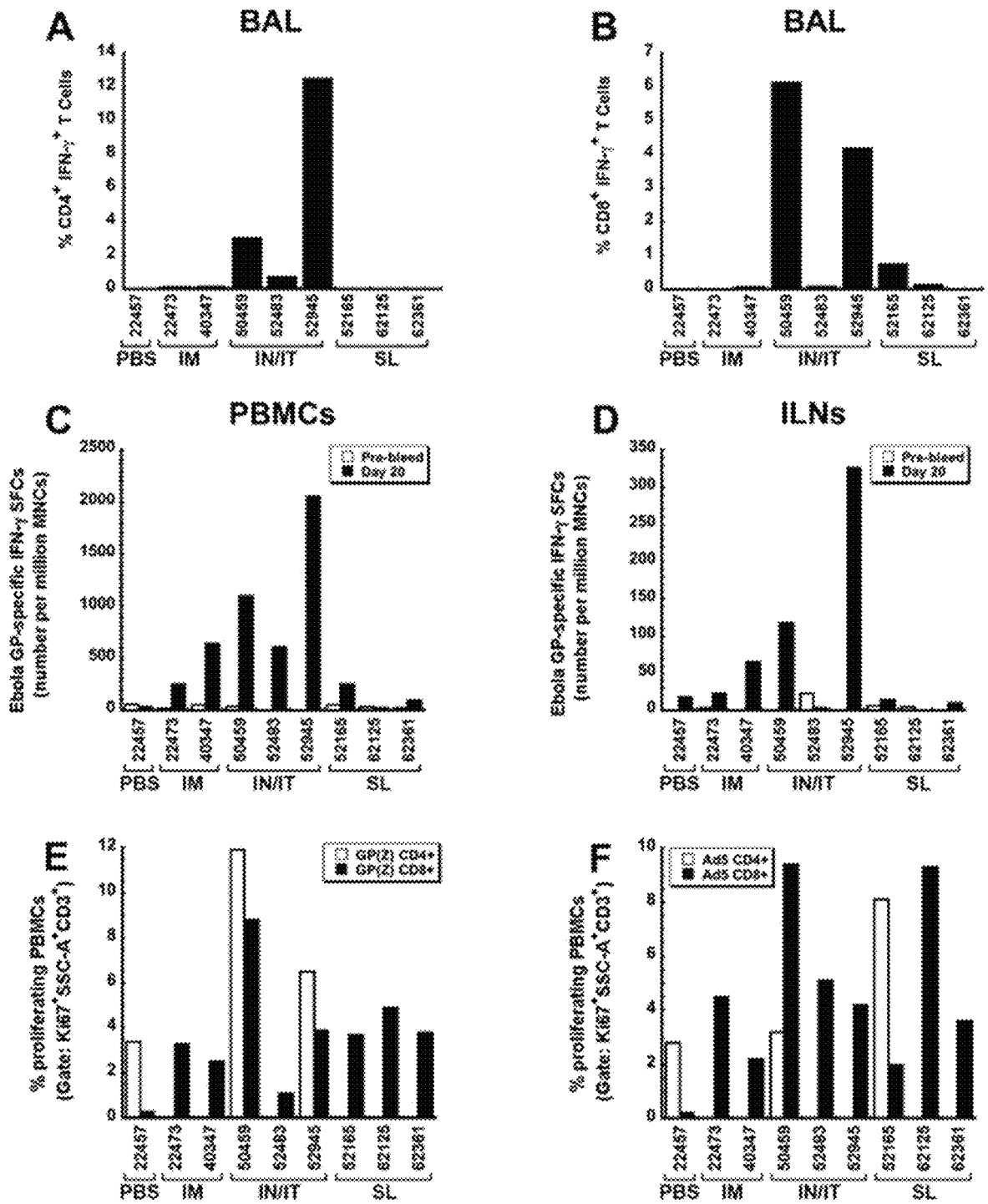
FIGS. 13A-13F: Primate Study 1: Respiratory immunization induces strong antigen-specific T cell responses after administration of a single dose of a formulated adenovirus-based Ebola vaccine. (13A) Quantitative analysis of Ebola glycoprotein-specific CD4$^+$ T cells in BAL fluid. Cells were isolated from whole blood 20 days after immunization and stimulated with a peptide library for Ebola glycoprotein or peptides specific for the MHC class II associated invariant chain peptide that binds the MHC class II groove of cells (h-Clip, negative control). Positive control cells were stimulated with PMA and ionomycin. Each cell population was stimulated for 5 h, stained for phenotypic markers, and analyzed by flow cytometry. (13B) Quantitative analysis of Ebola glycoprotein-specific CD8$^+$ T cells in BAL fluid. Cells were treated as described for 13A. (13C) Magnitude of the antigen-specific response of mononuclear cells isolated from whole blood of macaques. PBMCs were isolated 20 days after immunization from whole blood and evaluated for IFN- A single CD8+ IL-2+ population was detected in samples from primate 804819 (PEI-SL) and is not illustrated as a pie chart.

Twenty days after immunization, PBMCs were isolated from whole blood and incubated with peptides specific for Ebola glycoprotein (GP). Cells were then subjected to intracellular cytokine staining for CD8+ and CD4+ surface antigens and IFN-γ and sorted by flow cytometry. At this time point, few cells responsive to Ebola glycoprotein could be detected in PBMCs obtained from any of the animals (data not shown). A similar trend was observed in samples taken from iliac lymph nodes (ILNs) of animals. Profound responses were seen in samples obtained from the BAL fluid of animals given the vaccine by the IN/IT route. The strongest response was seen in CD4+ cells with 12.5% of the population obtained from primate 52945 and 3.03% of the population from primate 50459 responding (FIG. 13A). Although the response from the third primate in this treatment group (52483) was small in comparison (0.71%), it was significantly higher than that observed in animals given the vaccine by IM injection. The CD8+ T cell response followed a similar trend (FIG. 13B).

PBMC and ILN populations were further analyzed for IFN-γ production in response to Ebola GP by ELISpot. Samples from animals immunized by the IM route (22473 and 40347) both had significant numbers of IFN-γ producing cells (255 and 642 spot forming cells (SFCs)/million mononuclear cells (MNCs) respectively, FIG. 13C). PBMC samples from two NHPs immunized by the SL route (52165, 62361) also had measurable numbers of IFN-γ producing cells (257 and 98 SFCs/million MNCs). Samples from NHPs immunized by the IN/IT route contained the highest numbers of IFN-γ producing cells (1,100, 607, and 2,055 SFCs/million MNCs). Samples from the ILNs of 2 NHPs given the vaccine by the IN/IT route (50459 and 52945) contained approximately 7 and 18 times the number of IFN-γ producing cells found in the saline control (animal 22457) respectively (FIG. 13D).

38 days after immunization, the proliferative capacity of CD4+ and CD8+ cells in response to Ebola GP and adenovirus serotype 5 was assessed by a Ki-67 staining assay (Shedlock et al., 2010). Two samples, each obtained from animals immunized by the respiratory route, contained significant numbers of proliferative Ebola GP-specific CD4+ T cells (50459, 11.9%, and 52945, 6.5%, white bars, FIG. 13E). The sample obtained from NHP 50459 also contained the most Ebola GP-specific CD8+ T cells (8.8%, black bars, FIG. 13E). The sample from NHP 62125 immunized by the SL route contained the second highest amount of CD8+ T cells (4.9%). All remaining samples contained approximately 3-4% CD8+ T cells that could proliferate in response to Ebola GP except for that from animal 52483 (1.1%). Only one sample obtained from a primate immunized by the IN/IT route, 52165, contained a significant population of proliferative adenovirus 5-specific CD4+ T cells (8.1%, white bars, FIG. 13F). One sample from a primate in the IN/IT group (50459) and another from the SL group (62125) contained notable populations of CD8+ cells that proliferated in response to Ad5 (9.4 and 9.3% respectively, black bars, FIG. 13F). All remaining samples contained approximately 4% CD8+ T cells that could proliferate in response to adenovirus except for animal 40347 (2.2%).

The Antibody-Mediated Response

Figure 14A:
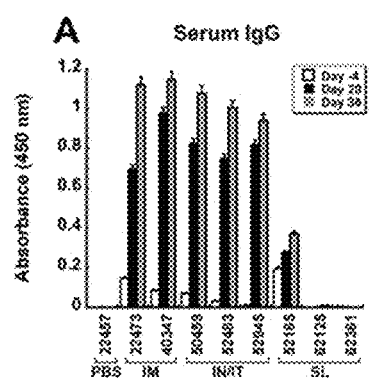
Figure 14B:
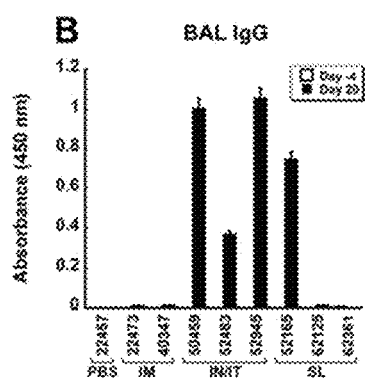
Figure 14C:
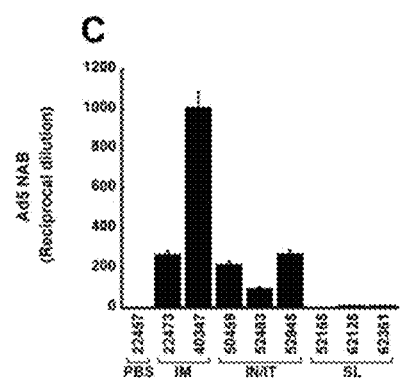

Anti-Ebola GP and anti-adenovirus antibody levels were assessed in serum and BAL fluid 20 and 38 days after immunization (FIGS. 14A-14C). Marked levels of anti-Ebola GP IgG antibodies were found in serum from animals immunized by the IM and the IN/IT routes 20 days after treatment (FIG. 14A). These levels increased further 38 days after vaccination. Anti-Ebola GP antibodies were found in the serum of only one of the animals immunized by the SL route (52165). This animal also had Ebola GP-specific IgG antibodies in BAL fluid 20 days after treatment (FIG. 14B) that were similar to those found in samples from animals immunized by the respiratory route. BAL from animals immunized by the IM route did not contain any detectable levels of anti-Ebola GP antibodies. One sample from a primate immunized by the IM route (40347) contained a significant amount of circulating anti-adenovirus neutralizing antibodies (NABs, 1,007 reciprocal dilution, FIG. 14C). The sample from the remaining animal in the IM group and 2 others from the IN/IT group contained anti-adenovirus NAB titers of ~200 reciprocal dilution. Serum from animals immunized by the SL route did not contain measurable levels of anti-adenovirus 5 NABs.

Figures 15A, 15B, 15C, 15D, 15E, 15F, 15G, 15H:
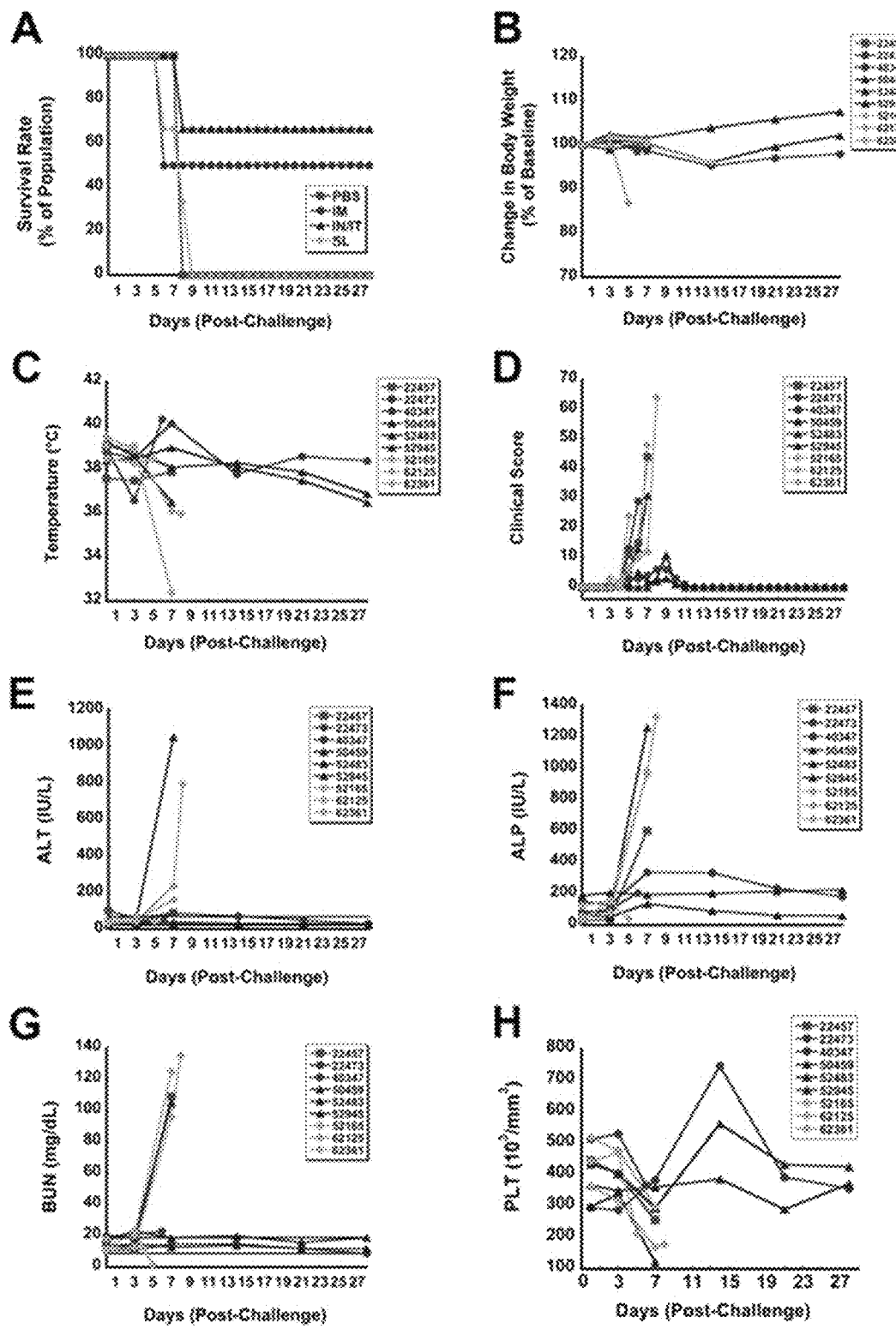

Lethal Challenge with Ebola Virus 62 days after immunization, NHPs were challenged with 1,000 pfu of Ebola virus (1995, Kikwit). One primate immunized by IM injection (40347) and one animal immunized by the SL route (62125) succumbed to infection 6 days after challenge (FIG. 15A). At this time animal 62125 had a clinical score of 23, and substantial petechiae were noted upon necropsy. Primate 40347 had a temperature of 40.3° C. and a clinical score of 25 and experienced notable bleeding. One primate immunized by the IN/IT route (52483) and one primate immunized by the SL route (62361) died the following day. Each of these animals had clinical scores above 25 and significantly decreased food intake the previous day. The remaining primate immunized by the SL route (52165) expired 8 days after challenge. One of the primates vaccinated by IM injection (22473) and two of the animals immunized by the IN/IT route (50459, 52945) survived challenge (50 and 67% survival IM and IN/IT respectively, FIG. 15A). Moderate drops in body weight were noted during infection (FIG. 15B). A slight increase in weight of one animal immunized by the IN/IT route (50459) was noted during the study period. Changes in body temperature (FIG. 15C) and clinical scores (FIG. 15D) for each primate were in line with survival results. The most striking changes in hematology and blood chemistry values were observed around day 5 postchallenge in the animals that did not survive. These include significantly elevated liver enzymes with ALT (FIG. 15E) and ALP (FIG. 15F) values rising to levels 27 and 16 times baseline respectively and blood urea nitrogen levels rising to 7.5 times normal values before the animals expired (FIG. 15G). Platelet counts, however, dropped to half the baseline values in these animals (FIG. 15H). In contrast, a sharp increase in platelets was noted in samples obtained from animals that survived challenge. Other hematology and blood chemistry values in these animals remained largely unchanged (data not shown).

TABLE 3

Primate Study 2: Shedding Patterns of Adenovirus DNA from the Rectal Mucosa of Non-Human Primates after a Single Dose of AdCAGoptZGP[a]

| route of immunization | animal # | pre | 0.25 d | 1 d | 2d | 7 d | 20 d |
|---|---|---|---|---|---|---|---|
| IN/IT | 0810003 | —[b] | 1,500[c] | $1.0 \times 10^5$ | $3.7 \times 10^4$ | 2,000 | 2,100 |
| | 0802197 | — | 380 | $7.5 \times 10^5$ | $2.6 \times 10^5$ | 420 | 540 |
| | 0809077 | — | — | $3.1 \times 10^4$ | $9.0 \times 10^4$ | 620 | 2,600 |
| SL | 0805257 | — | 83 | $6.0 \times 10^6$ | $3.6 \times 10^5$ | 780 | 79 |
| | 0804317 | — | 1,400 | $3.5 \times 10^4$ | $1.5 \times 10^4$ | 640 | 58 |
| | 0808233 | — | 200 | 5,600 | 1,600 | 5,600 | 24 |
| PEI-SL | 0807243 | — | 1,100 | $1.2 \times 10^5$ | 1,100 | 190 | 58 |
| | 0809227 | — | 920 | 440 | $1.1 \times 10^4$ | 130 | — |
| | 0804819 | — | 2,000 | $1.4 \times 10^6$ | 1,900 | 30 | — |

[a]Data were obtained by real-time TaqMan PCR on DNA isolated from samples as described.
[b]None detected. Sample fell below the detection limit of the assay (10 viral genomes/100 ng of DNA).
[c]Units are genome copies per swab.

EXAMPLE 11

Results of Primate Study 2

The second study, referred to as Primate Study 2, evaluated a novel formulation for the respiratory platform and involved refinement of the sublingual platform in naive animals and those with prior exposure to adenovirus. The workflow and treatment schedules for the study are depicted in FIGS. 10 and 16A-16B.

Figures 19A, 19B, 19C, 19D:
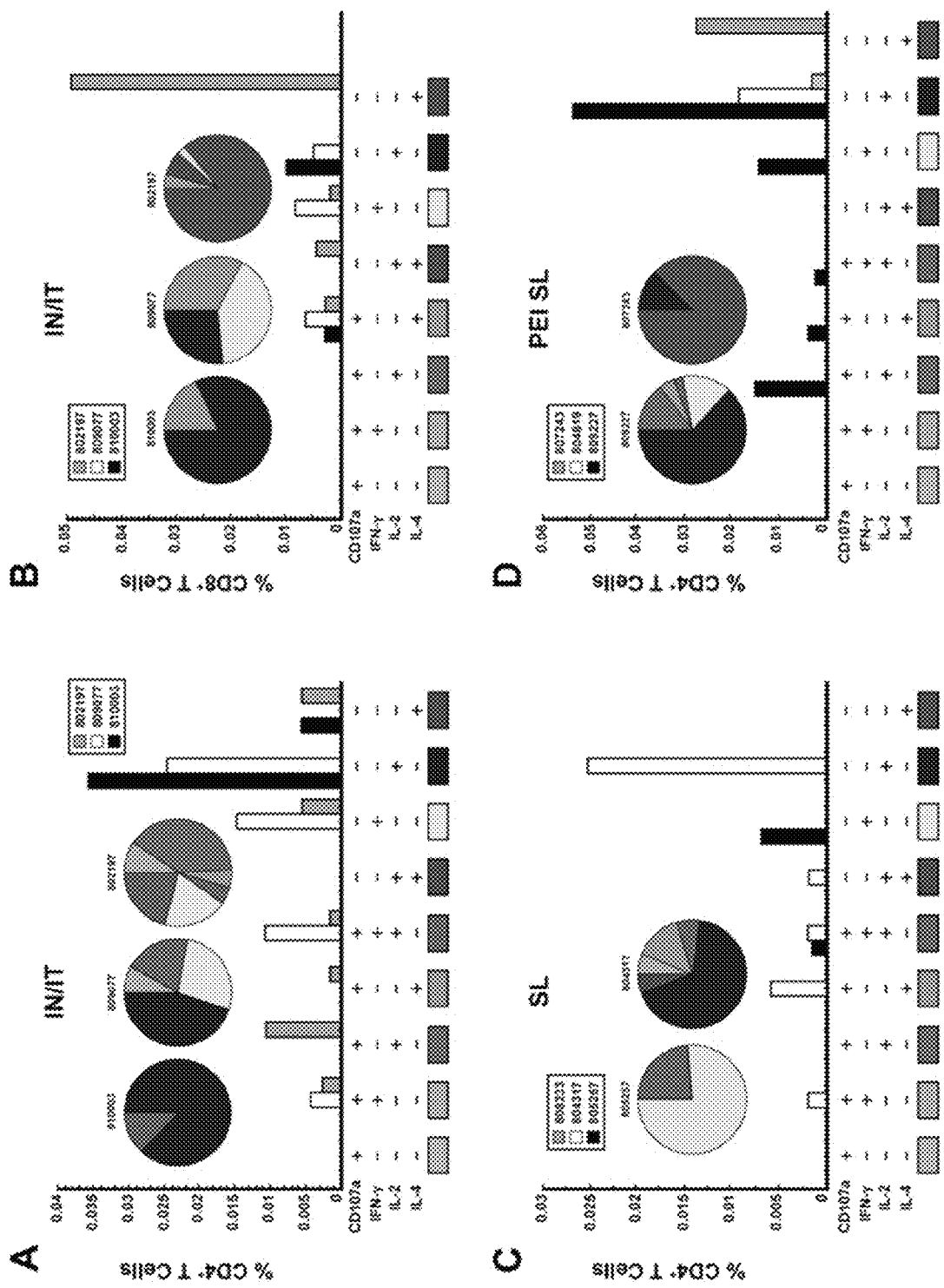

Effect of Formulation on Establishing Long-Lasting Immunity to Ebola and Refinement of Dose for Sublingual Immunization The most exciting finding extracted from Study 1 was that the combined IN/IT administration of the vaccine was able to confer long-term immunity to Ebola. Since it was not known if immunity induced by adenovirus-based vaccines for Ebola is persistent over time (Vasconcelos et al., 2012; Majhen et al., 2014), it was decided to extend the length of time between respiratory administration of a formulated version of the vaccine and challenge. A secondary goal was to increase the dose of vaccine given by the sublingual route and to evaluate the ability of the sublingual vaccine to confer protection in animals with prior exposure to adenovirus since improved responses in this population were observed in studies with rodents (Choi et al., 2013). The long-term immune response of surviving animals postchallenge was also a major point of interest in this study especially in animals receiving vaccine containing a novel formulation (Choi et al., 2014) and in those given the sublingual vaccine to identify parameters to target during additional refinement of each immunization platform.

Three male cynomolgus macaques were given the vaccine in a potassium phosphate buffer (pH 7.4) containing an amphiphilic polymer (formula weight (FW) ~39,000) formulation that improved the antigen-specific immune response in rodent models of infection (Choi et al., 2014). The goal was to immunize this group as early in the study as possible so that there would be a significant amount of time between immunization and challenge (FIGS. 16A-16B). 42 days after these animals were immunized, 3 macaques were given 1×1011 particles of a host range mutant adenovirus serotype 5 that can replicate in non-human primates (Buge et al., 1997; Klessing et al., 1979) by intramuscular injection to establish pre-existing immunity. 42 days later, animals were then given the vaccine by the sublingual route. At this time the animals had an average circulating anti-adenovirus antibody titer of 320±160 reciprocal dilution. Three naive animals were also given the same dose of vaccine by the sublingual route at the same time for comparison.

Toxicology and Vaccine Shedding

In contrast to the first study, a notable spike in creatine phosphokinase (CPK) was detected in the serum of all animals 24 h after immunization (FIG. 17A). This enzyme increased to 8 times baseline in one animal immunized by the IN/IT route (810003, 8,209 IU/L) and to 10 times baseline in a primate with pre-existing immunity to adenovirus immunized by the sublingual route (804819, 4,483). A notable spike in serum lactate dehydrogenase (LDH) was also noted at the 24 h time point. This was not as sharp as that seen with CPK with the highest elevations found to be approximately 3 times baseline (804317, 849 IU/L, FIG. 17B). Both parameters returned to normal within 3 days after treatment. As seen in the first study, serum AST increased in all primates after immunization. This occurred at the 24 h time point for animals immunized by the respiratory and sublingual routes but was not observed in primates with pre-existing immunity to adenovirus until 48 h (FIG. 17C). As in the first study, serum alkaline phosphatase (ALP) levels varied between primates, however, in this trial a distinct drop in this parameter was noted in samples collected from most animals between the 6 and 24 h time points, after which values remained constant (FIG. 17D). Other serological parameters evaluated during the first week after immunization (calcium, creatinine, albumin, globulin, total protein, gamma glutamyl transferase (GGT), total bilirubin, alanine aminotransferase (ALT), BUN, glucose, sodium, potassium, phosphate, chloride, and cholesterol) all fell within normal limits throughout the course of the study (data not shown).

Adenovirus genomes were only found in serum samples collected from animals immunized by the respiratory route (FIG. 18A). The most significant numbers of virus genomes detected in any of the biological samples collected throughout the second study were found in nasal swabs collected from primates 6 h after IN/IT immunization [810003 (8.18×106 genome copies (GC)), 809077 (1.44×107 GC), and 802197 (1.36×107 GC, FIG. 18B)] and in oral swabs collected from primates 6 h after sublingual immunization: [804317 (9.06×106 GC), 805257 (1.74×105 GC), and 808233 ($7.92\times10^{6}$ GC, FIG. 18D)]. As seen in the first study, adenovirus genomes were only found in the BAL fluid of animals immunized by the IN/IT route (FIG. 18C). Urine collected from one naive animal immunized by the SL route and another with pre-existing immunity also immunized by the SL route 6 h after treatment contained notable amounts of adenovirus (808233, 9,821 GC; 807243, 2,363 GC, FIG. 18E). Adenovirus genomes were found in feces collected from one primate with pre-existing immunity to adenovirus 24 h after immunization by the SL route (804819, 2.71×106 GC) and in another primate 2 days after it was immunized by the IN/IT route (802197, 6.51×106 GC, FIG. 18F). Virus continued to be shed in feces of this animal 1 week after immunization (802197, 2.52×106 GC). Adenovirus DNA was found on rectal swabs collected from each animal throughout the course of the study (Table 3).

The Long-Term T Cell Response

The Ebola virus glycoprotein-specific T cell response was examined in PBMCs isolated from whole blood immediately prior to challenge, 150 days post immunization. Multiparameter flow cytometry provided a comprehensive analysis of the types of antigen-specific T cells elicited by each treatment (FIGS. 19A-19D). The $CD4^+$ T cell population present in animals immunized by the IN/IT route was much more diverse than the $CD8^+$ T cell population (FIGS. 19A and 19B). Six specific $CD4^+$ T cell subpopulations were found in animal 802197 with the most predominate phenotype being $CD4^+$ $CD107a^+$ IL-$2^+$ (39% of the $CD4^+$ population, FIG. 19A). This animal also had the most diverse antigen-specific CD8+ T cell population with 4 different subpopulations detected by intracellular staining (FIG. 19B). Samples from NHP 809077 contained four different $CD4^+$ subpopulations. Cells that were $CD4^+$ IL-$2^+$ were most prevalent (45%) in this primate. The $CD8^+$ population in this animal was composed of 3 specific subtypes with relatively equal distribution ($CD8^+$ $CD107a^+$ IL-$2^+$, $CD8^+$ IFN-$\gamma^+$, and $CD8^+$ IL-$2^+$). The $CD4^+$ T cell population was less diverse in primate 810003 with the majority of antigen-specific cells also having the $CD4^+$ IL-$2^+$ phenotype (85%). The $CD8^+$ IL-$2^+$ subpopulation was the most prominent of two types of antigen-specific $CD8^+$ T cells found in this primate.

CD4+ and CD8+ T cell populations were noticeably less diverse in animals immunized by the SL route (FIG. 19C). Antigen-specific CD4+ T cells were not detected in samples collected from primate 808233. CD4+ IFN-$\gamma^+$ IL-2+ cells were present to a lesser degree than CD4+ IFN-$\gamma^+$ cells in samples collected from animal 805257 (25% and 75% of the population respectively). The most diverse CD4+ population elicited by SL immunization was found in primate 804317 with CD4+ IL-2+ cells being the most prominent of 5 different subtypes identified in this population. Antigen-specific CD8+ T cells were only found in samples collected from this animal with the majority being of the CD8+ CD107a+ phenotype (92.6%) and the remaining cells of the CD8+ IL-2+ phenotype (7.4%, data not shown).

Pre-existing immunity to adenovirus did not noticeably alter the diversity of T cells elicited by sublingual immunization (FIG. 19D). Five distinct subpopulations of CD4+ T cells were found in primate 809227 with those of the CD4+ IL-2+ being the most prominent (63.1%). A single population of CD8+ CD107a+ cells was also found in samples collected from this animal (data not shown). CD4+ IL-4+ cells were the most prominent of the two antigen-specific CD4+ T cell populations found in samples collected from primate 807243. Antigen-specific CD8+ T cells were not detected in samples collected from this animal. SL immunization induced a single population of CD4+ IL-2+ cells and a single population of CD8+ CD107a+ cells in primate 804819.

The Antibody-Mediated Response

Figures 20A, 20B, 20C, 20D, 20E, 20F:
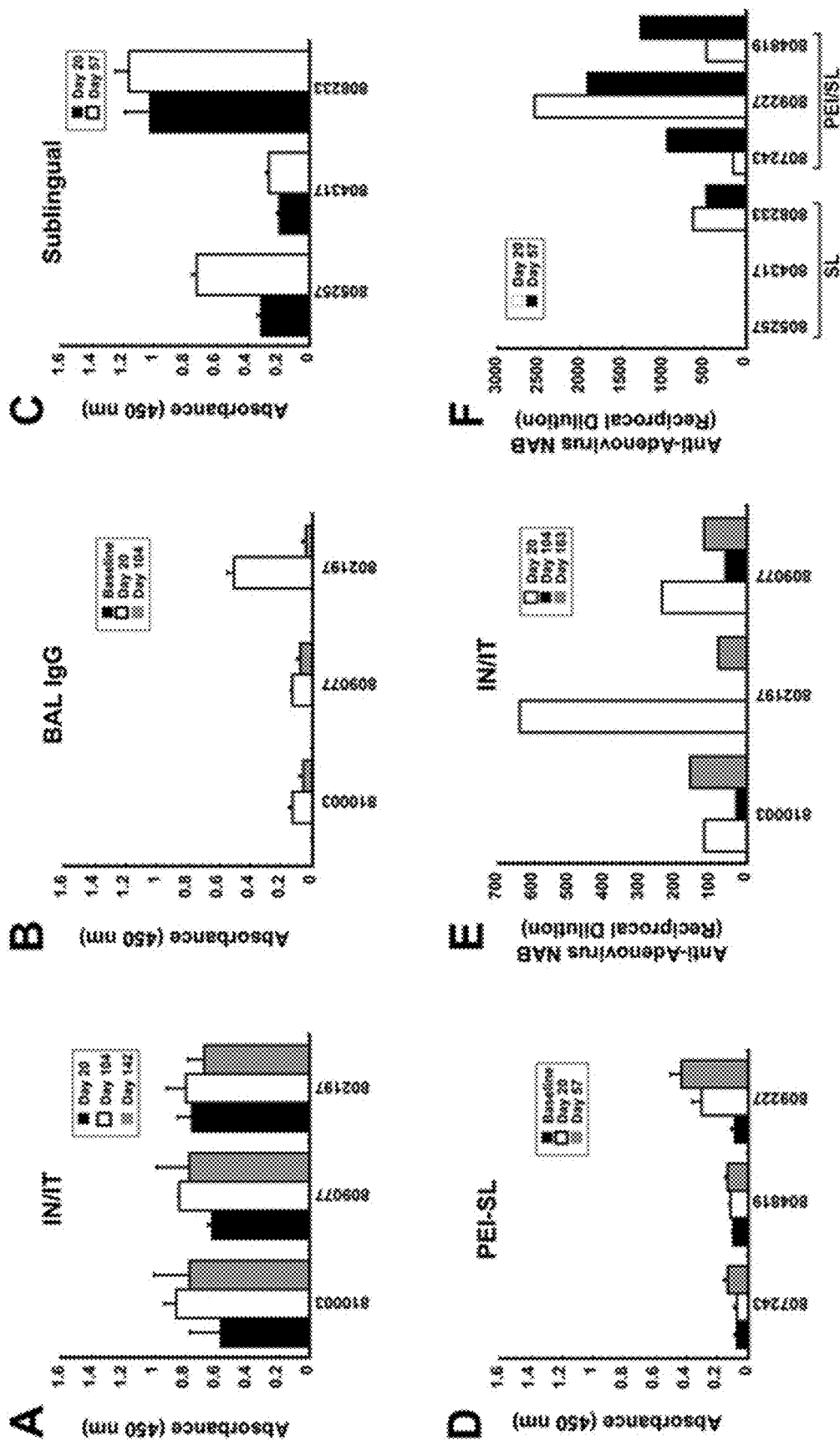
FIGS. 20A-20F: Primate Study 2: Respiratory immunization induces production of antigen-specific antibodies that are sustained over time. Serum was collected from cynomolgus macaques immunized by the IN route (20A) on days 20, 104, and 142 after immunization and analyzed for anti-Ebola GP IgG by ELISA as described (Choi et al., 2013). Serum was also collected from naive primates (20C) and those with pre-existing immunity to adenovirus (20D) on days 20 and 57 after immunization. These samples along with BAL fluid (20B) collected from all primates were screened for anti-Ebola GP antibodies in the same manner. Serum from animals immunized by the IN/IT route (20E) and from animals immunized by the SL route (20F) was also screened for anti-adenovirus neutralizing antibodies. In each panel, error bars represent the standard error of samples assayed in triplicate from each primate for each time point.

Anti-Ebola GP and anti-adenovirus antibody levels were assessed in serum and BAL fluid at various time points after immunization (FIGS. 20A-20F). Antigen-specific antibody levels mildly increased between day 20 and day 104 in serum collected from two animals immunized by the IN/IT route (0810003, 1.5-fold increase, 0809077, 1.3-fold increase, 0802197, no change, FIG. 20A). Antibody levels remained high at the 142 day time point and were comparable to those found in animals immunized by the respiratory route in the first primate study. Significant anti-Ebola GP antibody levels were detected in the BAL fluid of only one primate immunized by the IN/IT route (0802197, FIG. 20B). Samples obtained from one of the animals immunized by the sublingual route (0808233) contained the highest level of anti-Ebola GP antibodies than any of the other animals given a single dose of vaccine (FIG. 20C). It is also important to note that a significant change in anti-Ebola GP antibody levels between day 20 and day 57 post immunization was detected in samples obtained from only one animal in this treatment group (0805257, 2.4-fold increase). Samples from only one of the animals with prior exposure to adenovirus immunized by the sublingual route contained anti-Ebola GP antibodies above the detection limit of the assay (809227, FIG. 20D). While a notable amount of anti-adenovirus neutralizing antibody (NAB) was detected in the serum of one primate 20 days after immunization by the IN/IT route (802197, 1:640 reciprocal dilution), circulating anti-adenovirus NABs were low in samples obtained from other primates immunized in the same manner (FIG. 20E). Anti-adenovirus NABs were not found in the BAL of any of the primates immunized by the IN/IT route during the course of the study (data not shown). While anti-adenovirus NABs were quite high in the serum of one animal with pre-existing immunity 20 days after immunization by the SL route (809227, 1:2,560 reciprocal dilution), they were not detected in samples collected from two naive primates immunized in the same manner (805257, 804317, FIG. 20F).

Figures 21A, 21B, 21C, 21D, 21E, 21F, 21G, 21H, 21I:
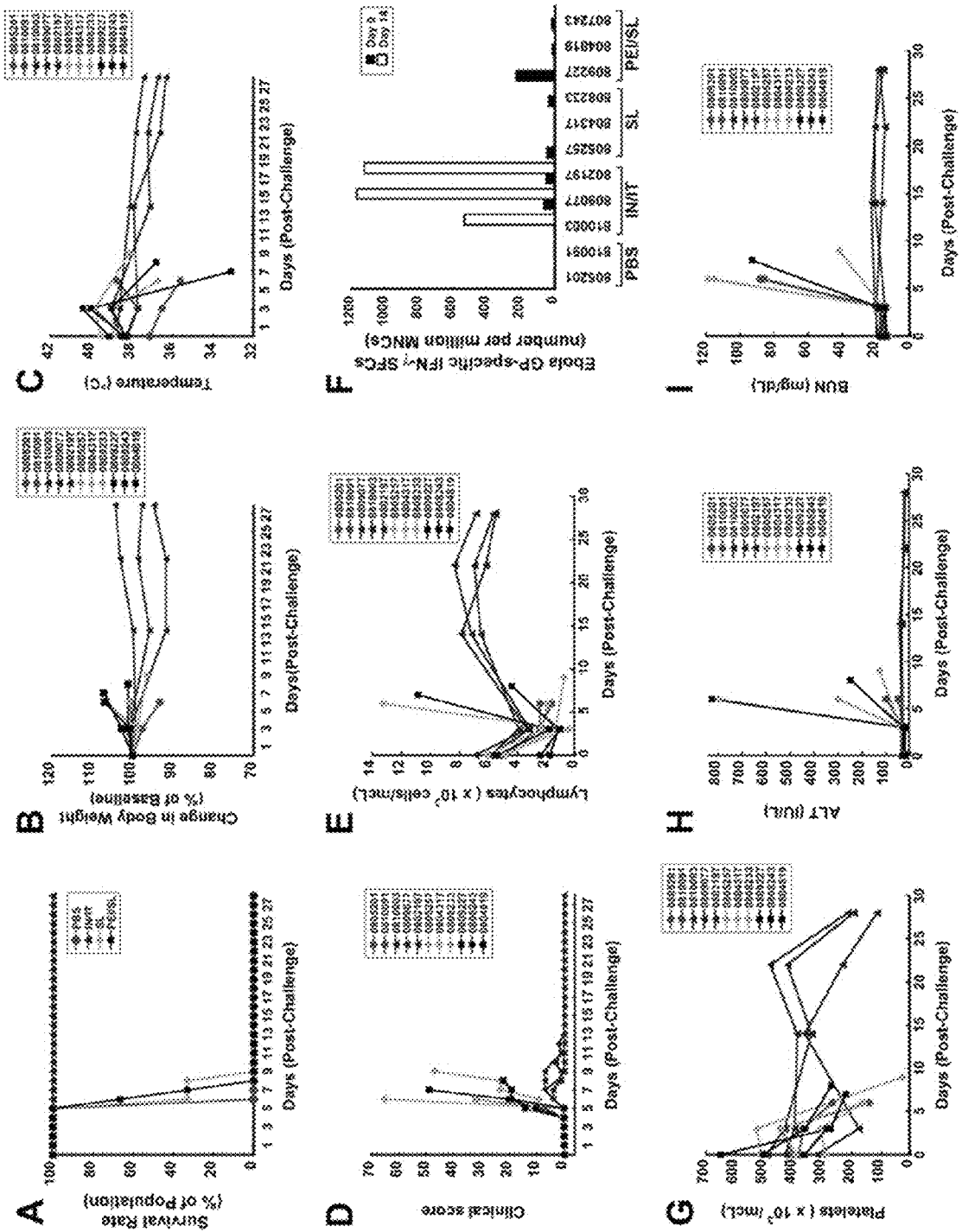
FIGS. 21A-21I: Primate Study 2: A single dose of a formulated adenovirus-based vaccine protects from lethal challenge 150 days after immunization. (21A) Kaplan-Meier survival curve. Cynomolgus macaques were given a single dose of $1.4 \times 10^9$ ivp of Ad-CAGoptZGP in a formulation containing sucrose (10 mg/ml), mannitol (40 mg/ml) and mg/mL poly(maleic anhydride-alt-1-octadecene) substituted with 3-(dimethylamino)propylamine, in phosphate buffered saline. Every animal immunized with this preparation survived lethal challenge. (21B) Body weight profiles of immunized animals challenged with Ebola. Animals succumbing to infection experienced a change of ±10% of body weight during the active infection period. (21C) Body temperature of primates during challenge. Body temperature declined in each animal during challenge with the most dramatic drops observed in animals that were not protected from infection. (21D) Clinical scores. Primates were observed on a daily basis during the challenge period. Clinical scores were recorded for each primate by a blinded technician using a standard, approved scoring methodology. (21E) Lymphocyte profiles. Lymphocytes of surviving animals recovered from an initial drop 3 days after challenge and remained stable throughout the remainder of the study. (21F) ELISpot analysis of the cellular immune response in surviving animals 14 days after challenge. PBMCs were isolated from whole blood and stimulated with a peptide pool spanning the Ebola glycoprotein. (21G) Platelet counts of primates during challenge. A notable drop in platelets was observed in all animals during challenge. (21H) Serum alanine aminotransferase (ALT) levels during challenge. Samples were collected from animals on day 3 and day 14 and at the time of death. (21I) Blood urea nitrogen (BUN) profile of immunized animals during challenge. This parameter remained unchanged in immunized animals that survived challenge. Red lines/circles: saline controls. Blue lines/triangles: IN/IT immunization. Orange lines/diamonds: SL immunization. Black lines/squares: animals with pre-existing immunity to adenovirus immunized by the SL route.
Figures 22A, 22B, 22C, 22D, 22E, 22F:
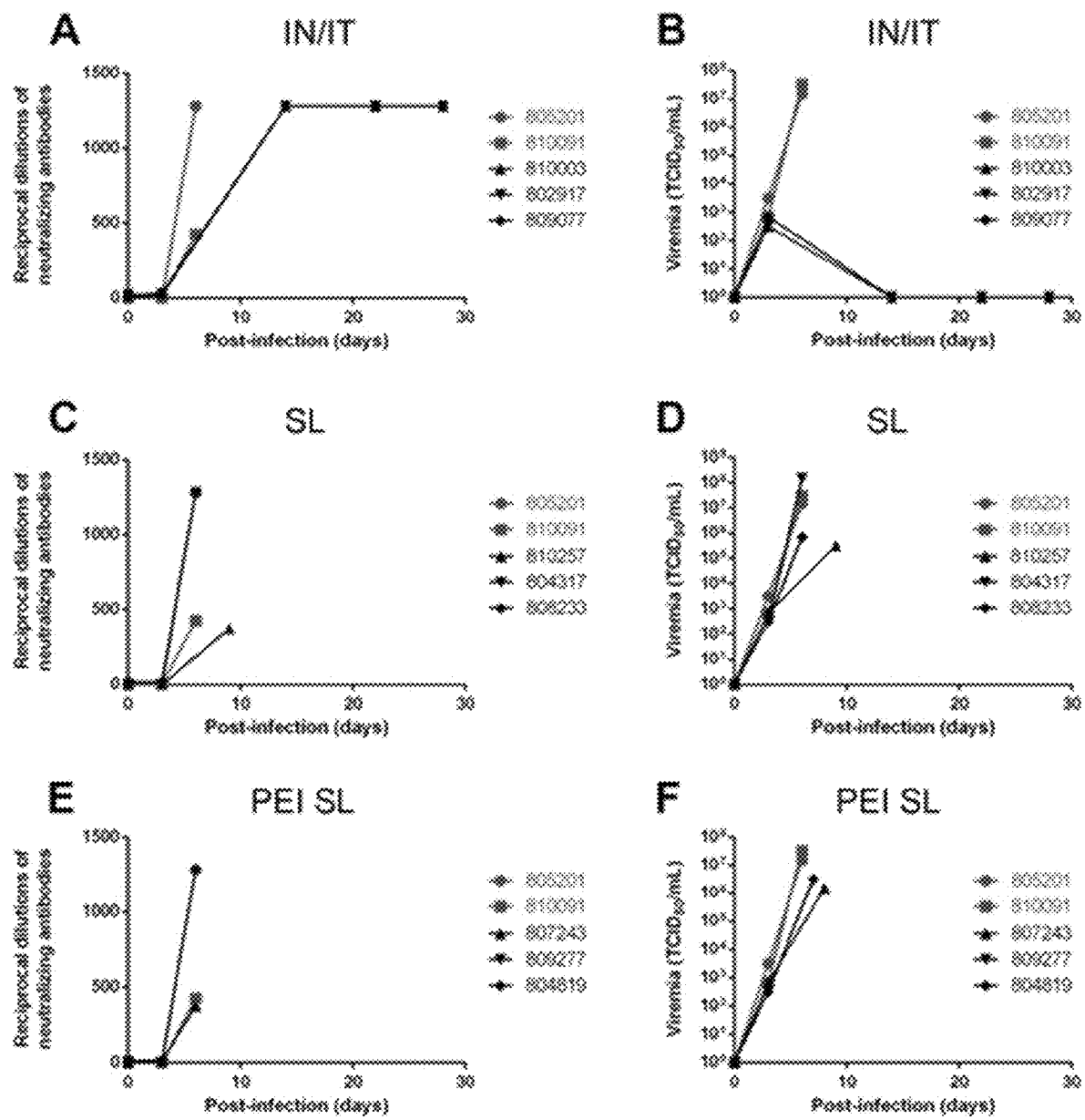
FIGS. 22A-22F: Anti-Ebola GP antibodies generated by a formulated adenovirus-based respiratory vaccine are neutralizing while those produced by an unformulated sublingual vaccine are partially neutralizing. The neutralizing capacity of antibodies in serum collected from each primate was assessed using a fluorescence neutralization assay (FIGS. 22A, 22C, and 22E). The amount of Ebola virus present in the serum of animals during challenge was determined using a standard infectious titer assay (FIGS. 22B, 22D, and 22F). In each panel, data obtained from animals given saline prior to challenge with Ebola are included as red symbols and lines for reference. $TCID_{50}$=median tissue culture infectious dose 50 or the amount of virus that will produce pathological change in 50% of cells that are infected in culture. These assays were performed under BSL-4 conditions at the National Microbiology Laboratory in Winnipeg.

Lethal Challenge with Ebola Virus 150 days after immunization, animals were challenged with 1,000 pfu of Ebola virus (1995, Kikwit). Six days after challenge, both primates given saline, two animals immunized by the SL route (804317, 808233), and one animal with pre-existing immunity to adenovirus immunized by the SL route (809227) expired from infection (FIG. 21A). The remaining primates with pre-existing immunity succumbed to infection on days 7 (804819) and 8 (807243) respectively. The remaining animal given the vaccine by the SL route (805257) expired on day 9. Each animal immunized by the respiratory route survived challenge. These animals experienced minimal changes in body weight (FIG. 21B) and temperature (FIG. 21C) during the course of infection with their clinical scores peaking at about 4-7 days after challenge (FIG. 21D).

A notable drop in lymphocyte levels of all animals was observed 3 days after challenge (FIG. 21E). Lymphocytes abruptly spiked in one animal immunized by the SL route (808233) and another with pre-existing immunity to adenovirus (804819) 6 days after challenge. Lymphocyte levels of primates immunized by the IN/IT route slowly increased to day 14 where they remained constant. Lymphocytes of all other animals remained low until the time of death. ELISpot analysis revealed that a significant amount of MNCs capable of producing IFN-$\gamma$ in response to stimulation with Ebola GP peptides were present in PBMCs isolated from whole blood of surviving animals 14 days after challenge (FIG. 21F). A sharp drop in platelet counts was noted in all animals that did not survive challenge (FIG. 21G). Mild drops in platelet counts were observed in animals immunized by the IN/IT route 3 days after challenge. These values continued to drop through day 28. ALT (FIG. 21H) and BUN (FIG. 21I) sharply rose to values as high as 24 and 6 times baseline respectively in animals that succumbed to Ebola infection. These values remained unchanged throughout Ebola infection in surviving animals.

Assessment of sera taken during challenge revealed that primates immunized by the IN/IT route had very high levels of circulating anti-Ebola GP antibodies (FIG. 22A). These were neutralizing since very low levels of infectious Ebola were found in samples taken from two primates 3 days postchallenge (FIG. 22B). Infectious Ebola virus was not detected in any samples collected from the third animal in this treatment group (809077). Ebola virus genomes were also not detected in samples taken from any of the animals immunized by the respiratory route (Table 4). Although samples from two animals immunized by the sublingual route also contained high levels of anti-Ebola neutralizing antibody (804317, 808233, 1,280 reciprocal dilution, FIG. 22C), they were only partially neutralizing since a concentration of 316 $TCID_{50}$/mL was found in samples collected from both primates at the 3 day time point that escalated to $1.47\times10^8$ and $6.81\times10^8$ TCID50/mL respectively by the 6 day time point (FIG. 22D). The number of circulating virus genomes in these animals followed a similar trend (Table 4). One animal that was exposed to the adenovirus serotype 5 host range mutant prior to immunization by the SL route (804819) also had high levels of anti-Ebola GP circulating antibodies (1,280 reciprocal dilution, FIG. 22E), however, Ebola virus RNA was detected in samples collected from this animal at a concentration of $8.19\times10^6$ genome copies/mL (Table 4). This animal expired before any infectious virus could be detected in its serum (FIG. 22F).

TABLE 4

Primate Study 2: Circulating Ebola Virus Genomes in Primates Challenged with Ebola Virus 150 Days after Immunization with a Single Dose of AdCAGoptZGP[a].

| animal no. | treatment/ route | day 0 | day 3 | day 3.8 | day 14 | day 21 | day 28 |
|---|---|---|---|---|---|---|---|
| 0810091 | KPBS | —[b] | 880[c] | 1.84 × 10⁵ | d | N.A.[e] | N.A. |
| 0805201 | KPBS | — | — | 7.79 × 10⁵ | d | N.A. | N.A. |
| 0802197 | IN/IT | — | — | N.A. | — | — | — |
| 0809077 | IN/IT | — | — | N.A. | — | — | — |
| 0810003 | IN/IT | — | — | N.A. | — | — | — |
| 0805257 | SL | — | — | N.A. | d | N.A. | N.A. |
| 0804317 | SL | — | 1.74 × 10⁴ | 9.84 × 10⁶ | d | N.A. | N.A. |
| 0808233 | SL | — | 1.01 × 10³ | 1.14 × 10⁶ | d | N.A. | N.A. |
| 0809227 | PEI-SL | — | 2.08 × 10⁴ | 1.57 × 10⁴ | d | N.A. | N.A. |
| 0804819 | PEI-SL | — | — | 8.19 × 10⁶ | d | N.A. | N.A. |
| 0807243 | PEI-SL | — | 3.33 × 10⁴ | 3.3 × 10⁵ | d | N.A. | N.A. |

[a]Data were obtained by quantitative RT-PCR on RNA isolated from whole blood as described.
[b]None detected. Sample fell below the detection limit of the assay (86 viral genomes/mL).
[c]Units are genome copies per milliliter of whole blood (GC/mL).
d - Animal expired prior to sample collection at this time point.
e - Not assayed at this time point.

EXAMPLE 12

Flexible Film Technology

Biologicals can be stabilized in small, unit dose films useful for administration to a variety of animal models and for evaluation of long-term stability of vaccines during long-term storage (see FIG. 23A). Several thousand doses of a given biological substance can be stabilized in large films that can be divided into single-use doses (see FIG. 23B).

A supersaturated solution was created by adding sufficient stabilizers (sugars and sugar derivatives, polymers) and permeability enhancers (surfactants) to a solvent system (distilled deionized water, tris buffer, ethanol, methanol) such that the total amount of solid components added to the solvent were within the concentration of 10-90% w/w. In some embodiments, the solution was formulated comprising potassium phosphate buffered saline (pH 7.4), a detergent (10 mg/ml PMAL-C16 in certain aspects) and, optionally, one or more sugars.

This suspension was prepared by stirring, homogenization, mixing and/or blending these compounds with the solvent. Small portions of each component (~1/10 the total amount) were added to the solvent and the solution was mixed before adding additional portions of the same agent or a new agent.

Once each stabilizer and permeability enhancer was added, the bulk solution was placed at 4° C. for a period of time between 2-24 hours. After this time, the bulk solution was subject to sonication for a period of 5-120 minutes to remove trapped air bubbles in the preparation.

After sonication was complete, the recombinant adenovirus vector was added to the preparation. The amount of adenovirus ranged from of 0.1-30% of the total solid concentration. Adjuvants, in some aspects, were added at this time. The amount of these compounds ranged from 0.005-10% of the total solid concentration. These agents were added by gentle stirring (10-50 rpm) so as to not induce air pockets and bubble formation in the final preparation.

The preparation was then slowly piped into molds of a shape suitable for the application. In certain aspects, the molds can be constructed of stainless steel, glass, silicone, polystyrene, polypropylene and other pharmaceutical grade plastics. In some aspects, the preparation can be placed in the molds by slowly pouring by hand or by pushing the preparation through a narrow opening on a collective container at a slow controlled rate (0.25 ml/min) to prevent early hardening and/or bubble formation in the final film product. Films were poured to a thickness of 12.5-1000 µm.

Molds for casting of films were sterilized by autoclaving and placed in laminar air flow hoods prior to casting. Molds were also sometimes lined with a peelable backing material suitable for protection of the film product. Suitable backings can be made of aluminum, gelatin, polyesters, polyethylene, polyvinyl and poly lactic co-glycolide polymers and/or any other pharmaceutically acceptable plastic polymer.

Cast films remained at ambient temperature (20-25° C.) in a laminar flow hood for 2-24 hours after which time a thin, peelable film was formed. Some films were opaque or, preferably, translucent (see FIGS. 23A-23B). Films were then stored at room temperature under controlled humidity conditions. Some films were stored at 4° C. under controlled humidity as well.

Figure 25:
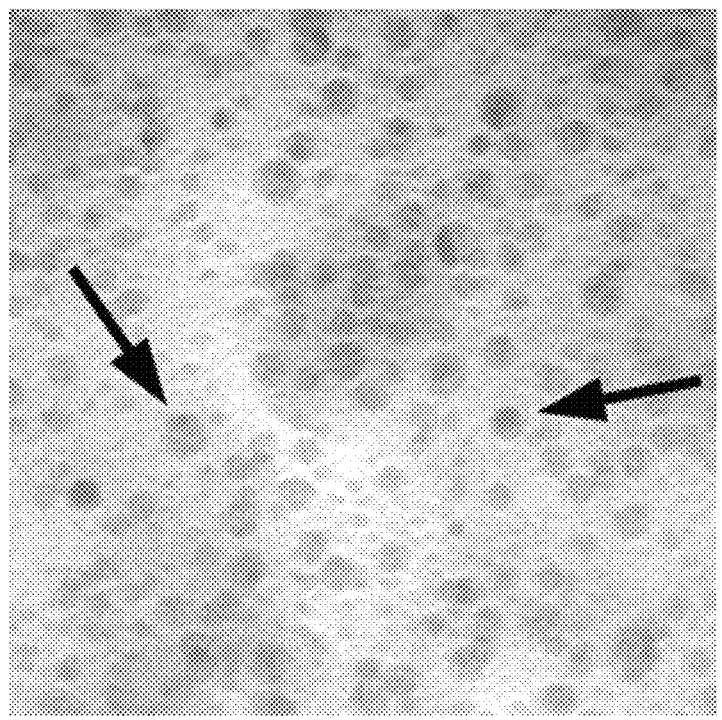
FIG. 25: Films Retain 3 Dimensional Shape of Embedded Virus After 12 months of Storage at Room Temperature. Virus particles (70 nm, shaded areas, arrows) embedded in film (Formulation 2 in FIG. 2) and stored in the dry state for one year. Film was embedded in epoxy resin, sectioned frozen and transferred directly to the electron microscope under osmium vapor. (Magnification 20,000×).

Films were porous, amorphous solids that stabilized the recombinant adenovirus vector in their native three-dimensional shape (see FIGS. 24A-24D). The films retained the shape of the embedded virus after twelve months of storage at room temperature (FIG. 25).

Multilayer films can also be created at this time by applying a second coating of a supersaturated solution containing the same antigen as the first layer or another different adjuvant/antigen system to the thin film in a laminar flow hood. This will remain at ambient temperature (20-25° C.) in a laminar flow hood for an additional 2-24 hours after which time a thin, peelable film will be formed. This film may be opaque. It may also be translucent. In certain aspects the films may likewise comprise multiple film layers.

Films were dissolved in saline or simulated human saliva warmed to 37° C. (body temperature) and time needed for full dissolution noted immediately upon drying and at various times during storage. The resulting solutions were screened for antigen confirmation and activity to determine the effectiveness of the formulation to retain the potency of the preparation over time. The results are shown in FIGS. 26-40.

Figure 26:
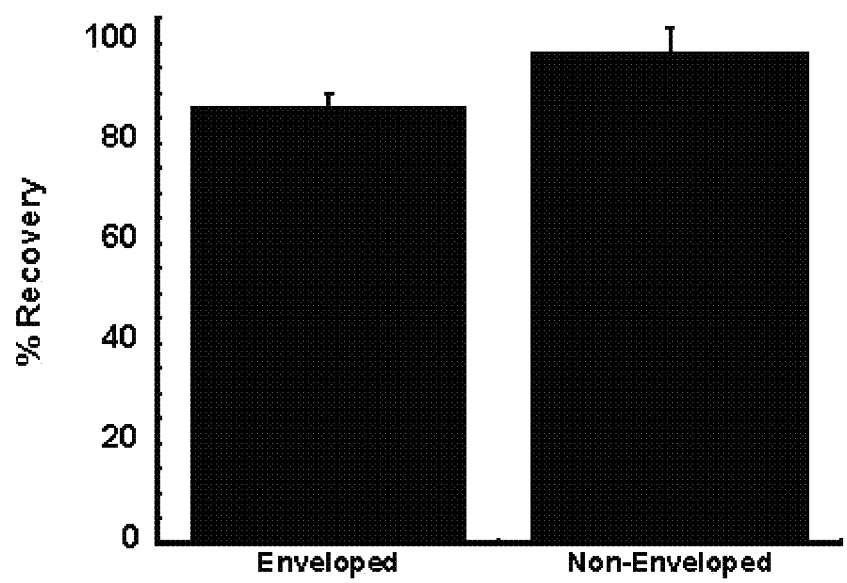
FIG. 26: Infectious Enveloped and Non-Enveloped Viruses Can Be Recovered from Dried Film. Infectious titers of recombinant adenovirus expressing the Ebola Virus glycoprotein (a non-enveloped virus) and PR8 (H1N1 influenza) were evaluated in liquid formulations, dried and reconstituted 48 hours after storage in the dry state at 20° C. Data is recorded as the difference in titers of each preparation prior to drying and after reconstitution.

Both infectious enveloped and non-enveloped viruses were found to be recoverable from dried film (FIG. 26). Infectious titers of recombinant adenovirus expressing the Ebola Virus glycoprotein (a non-enveloped virus) and PR8 (H1N1 influenza) were added to liquid formulations, dried and reconstituted 48 hours after storage in the dry state at 20° C. Percent recovery was between 85% and 95% for both viruses (FIG. 26).

Figure 27:
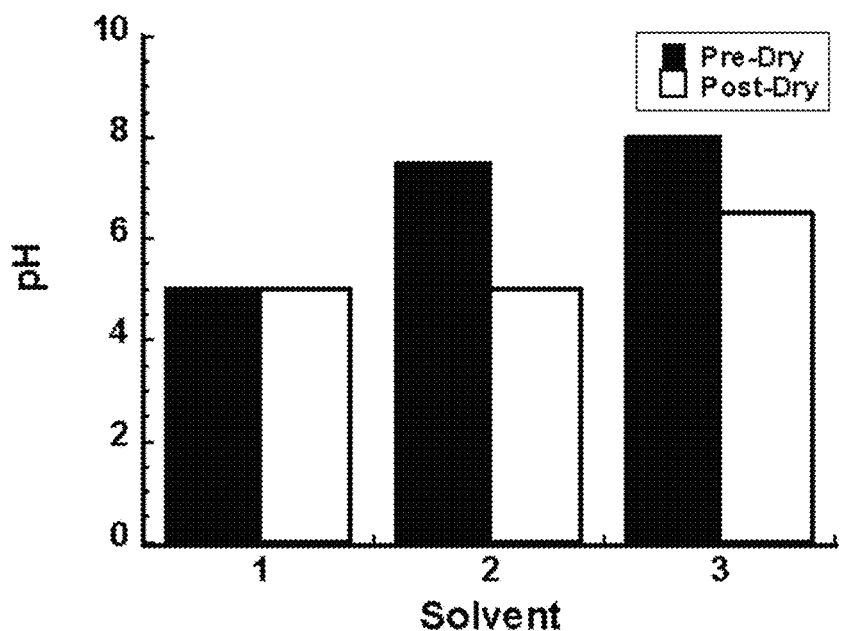
FIG. 27: Solvent System Influences Changes in Film pH During the Drying Process. The pH of each formulation in the liquid (pre-dry) and dry state was recorded according to the method described in Croyle et al. (2001) *Gene Ther.* 8: 1281-1290. Prior to drying, 10 microliters of Universal pH Indicator Solution (Fisher Scientific) was added to each formulation and the pH visually recorded. When drying was complete, films were visually inspected and the pH compared to pre-drying values. On the x-axis, 1 is distilled, deionized water, 2 is 120 mM PBS (phosphate buffered saline), and 3 is 10 mM Tris (Tris(hydroxymethyl)aminomethane). Formulations evaluated in this study consisted of 0.1-15% hydroxypropyl methylcellulose, 0.1-0.8% tragacanth gum, 1-5% sorbitol and 1-100 mg/ml melezitose.
Figures 28A, 28B, 28C:
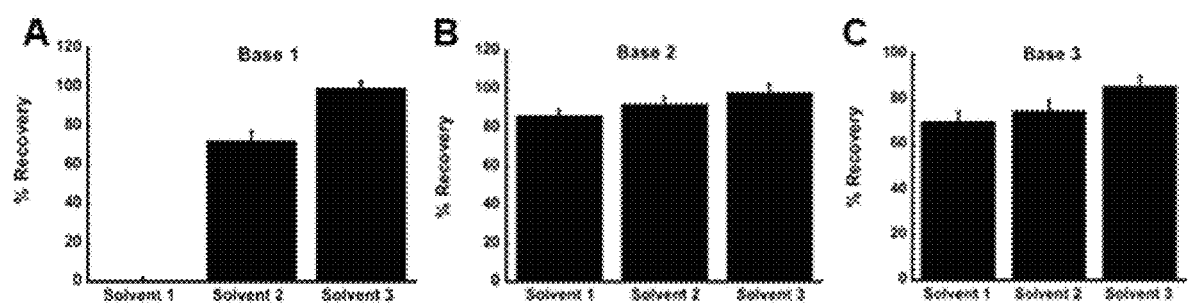
FIGS. 28A-28C: Solvent System Dictates Recovery of Virus from Dried Film. Three different aqueous solvent systems were utilized in formulations containing: Low (Base 1, 0.5%) (28A), Medium (Base 2, 1.5%) (28B), and High (Base 3, 3%) (28C) concentrations of hydroxypropyl methylcellulose, (Base in figure). Films were dried at ambient temperature and pressure for 5 hours. Twenty four hours later, each film was reconstituted with sterile saline and infectious titer of virus embedded in the preparation determined by serial dilution, infection of HeLa cells and visual tallying of cells staining positive for virus. Percent recovery was calculated using the following formula.

Different solvent systems influenced changes in film pH during the drying process (FIG. 27). Solvents such as distilled, deionized water (1), PBS (phosphate buffered saline (2)), and Tris (Tris(hydroxymethyl)aminomethane (3)) were used (see FIG. 27). The solvent system also dictated recovery of virus from dried film (FIGS. 28A-28C). The pH of the dried film significantly impacted recovery of infectious virus after reconstitution (FIG. 29). The lower the pH, the lower the percent recovery; when the pH was higher, percent recovery was higher (FIG. 29). The addition of detergent to the formulation was found to prevent a drop in film pH after drying (FIG. 30).

Figure 33:
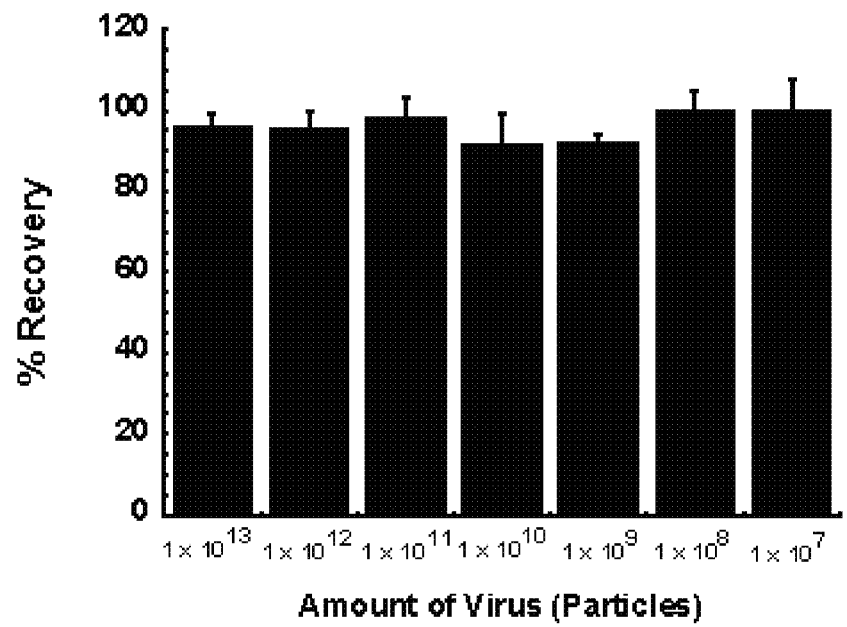
Figure 34:
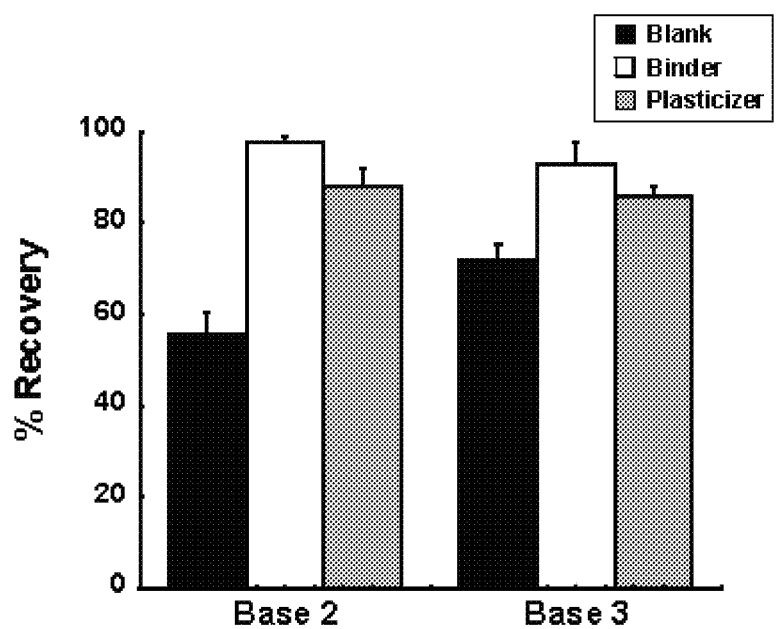
Figure 35:
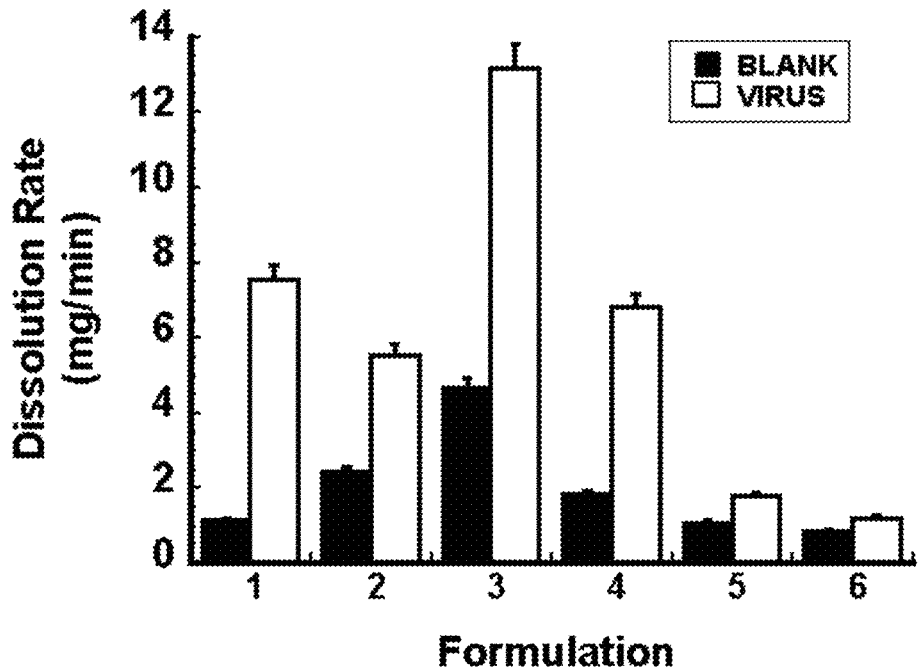
Figure 36:
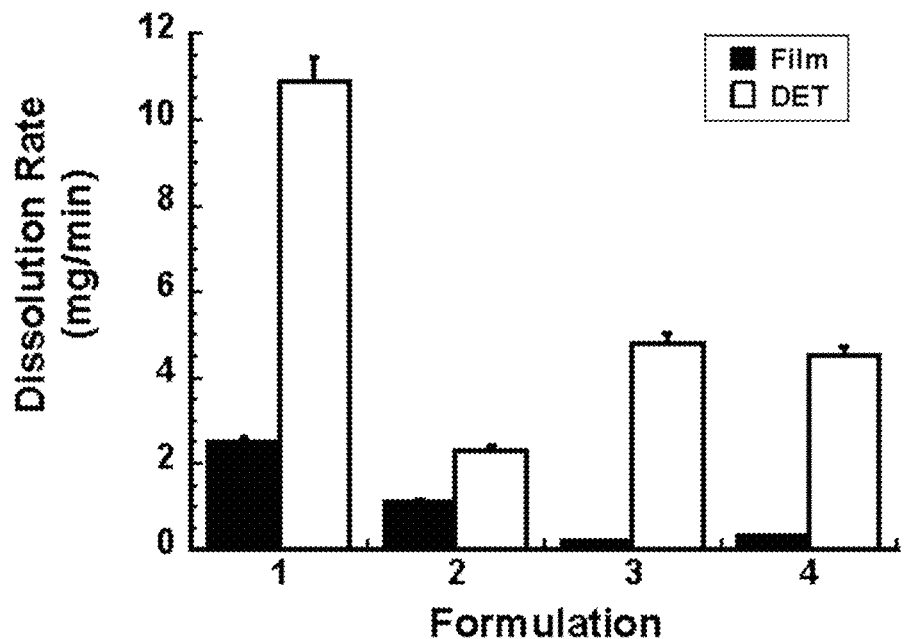
Figure 37:
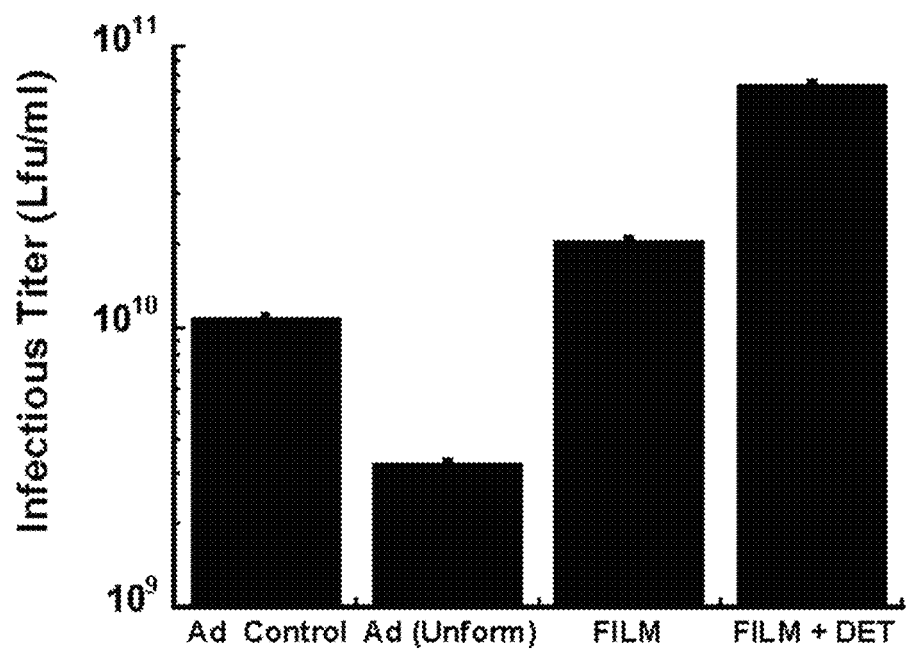
Figure 38:
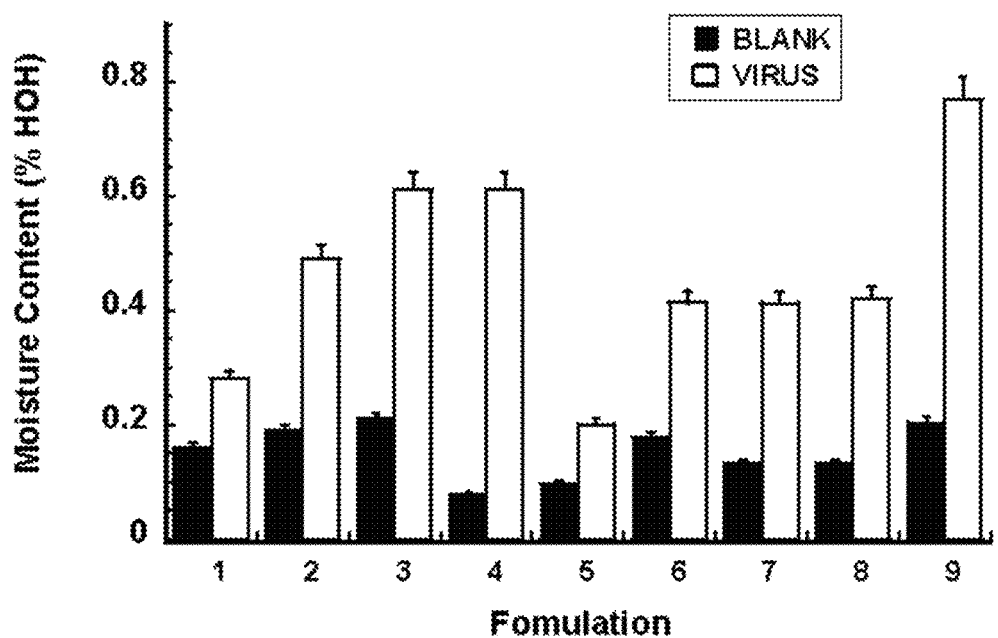
Figure 39:
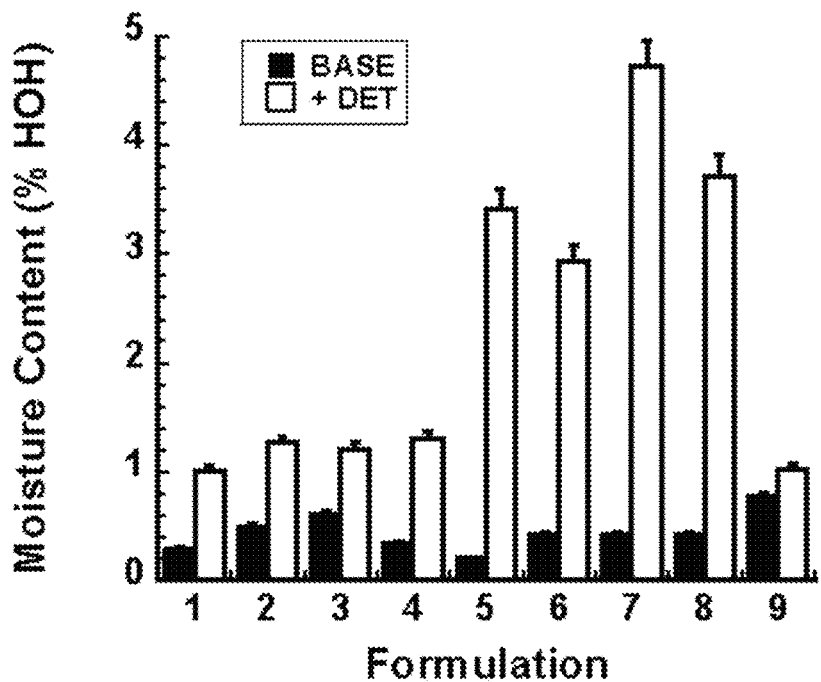

Base formulations also played a role in recovery of virus from dried film. Three different stabilizer concentrations were evaluated for their ability to retain infectious titer of virus after drying in two different solvent systems with varying results (FIGS. 31A-31B). In addition to affecting pH levels, detergent was found to significantly improve recovery of infectious virus from the films (FIG. 32). However, the amount of virus embedded in film formulation did not impact recovery (FIG. 33). The use of binding agents improved recovery of recombinant virus film (FIG. 34).

When compared to blank controls, the virus presence was found to significantly impact dissolution rate of films in simulated human saliva (FIG. 35). The addition of a detergent to the film then significantly improved dissolution time (FIG. 36). Film formulations with and without detergent were shown to protect adenovirus from degradation in saliva (FIG. 37).

The presence of virus in the film significantly increased the moisture retention in dried film formulations when compared to blank controls (FIG. 38). The addition of detergent profoundly increased moisture content in dried film containing virus (FIG. 39). Additionally, it was found that recombinant adenovirus can be evenly distributed across large films that can then be divided into equal unit doses (FIG. 40).

Examples of formulations used in these experiments are shown below in Table 5.

TABLE 5

| All formulations contained 0.2% w/v tragacanth gum. | |
|---|---|
| 1 | .5 |
| 2 | .5/2S |
| 3 | .5/2G |
| 4 | 1.5 |
| 5 | 1.5/2S |
| 6 | 1.5/2G |
| 7 | 3 |
| 8 | 3/2S |
| 9 | 3/2G |

0.5 = 0.5% (w/w) HPMC, 1.5 = 1.5% (w/w) HPMC, 3 = 3% (w/w) HPMC, 2S = 2% (w/w) Sorbitol, 2G = 2% (v/v) Glycerol.

The stability of viral particles in a formulation of the embodiments is shown in FIGS. 41A-41B. As can be seen in FIG. 41B, even when in a liquid form, the adenovirus retained nearly all its starting infectivity after 8 months of storage. Importantly, when stored in a solid formulation detailed herein nearly all infectivity can be maintained for longer than 36 months (see FIG. 41A).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

Abbink, P., Lemckert, A. A., Ewald, B. A., Lynch, D. M., Denholtz, M., Smits, S., Holterman, L., Damen, I., Vogels, R., Thorner, A. R., O'Brien, K. L., Orville, A., Mansfield, K. G., Goudsmit, J., Havenga, M. J., and Barouch, D. H. (2007). Comparative seroprevalence and immunogenicity of six rare serotype recombinant adenovirus vaccine vectors from subgroups B and D. J. Virol. 81(9): 4654-4663.

Ahmed, N.; Gottschalk, S.How to Design Effective Vaccines: Lessons from an Old Success Story Expert Rev. Vaccines. 2009, 8 (5) 543-546

AVMA Guidelines on Euthanasia (Formerly Report of the AVMA Panel on Euthanasia) June 2007. Available from: avma.org/resources/euthanasia.pdf Bachmann, M. F., Jennings, G. T., Vaccine Delivery: A Matter of Size, Geometry, Kinetics and Molecular Patterns. Nat. Rev. Immunol., 2010 10(11): 787-796.

Bae, K., Choi, J., Jang, Y., Ahn, S., and Hur, B. (2009). Innovative vaccine production technologies: the evolution and value of vaccine production technologies. Arch. Pharm. Res. 32(4): 465-480.

Barouch, D. H., Kik, S. V., Weverling, G. J., Dilan, R., King, S. L., Maxfield, L. F., Clark, S., Nganga, D., Brandariz, K. L., Abbink, P., Sinangil, F., De Bruyn, G., Gray, G. E., Roux, S., Bekker, L. G., Dilraj, A., Kibuuka, H., Robb, M. L., Michael, N. L., Anzala, O., Amornkul, P. N., Gilmour, J., Hural, J., Buchbinder, S. P., Seaman, M. S., Dolin, R., Baden, L. R., Carville, A., Mansfield, K. G., Pau, M. G., and Goudsmit, J., International Seroepidemiology of Adenovirus Serotypes 5, 26, 35, and 48 in Pediatric and Adult Populations. Vaccine, 2011 29(32): 5203-5209.

Beilin, B., Martin, F. C., Shavit, Y., Gale, R. P., and Liebeskind, J. C. (1989). Suppression of natural killer cell activity by high-dose narcotic anesthesia in rats. Brain Behav Immun. 3, 129-137.

Bolhassani, A., Javanzad, S., Saleh, T., Hashemi, M., Aghasadeghi, M. R., and Sadat, S. M., Polymeric Nanoparticles: Potent Vectors for Vaccine Delivery Targeting Cancer and Infectious Diseases. Hum. Vaccin. Immunother., 2014 10(2): 321-332.

Bolton, D. L., and Roederer, M. (2009). Flow cytometry and the future of vaccine development. Expert Rev. Vaccines. 8(6): 779-789.

Bolton, S. (1997). Pharmaceutical Statistics Practical and Clinical Applications. New York, N. Y., Marcel Dekker, Inc.

Bray, M., Davis, K., Geisbert, T., Schmaljohn, C., and Huggins, J. (1998). A mouse model for evaluation of prophylaxis and therapy of Ebola hemorrhagic fever. J Infect Dis. 178, 651-661.

Bray, M., Davis, K., Geisbert, T., Schmaljohn, C., and Huggins, J., A Mouse Model for Evaluation of Prophylaxis and Therapy of Ebola Hemorrhagic Fever. J. Infect. Dis; 1999 179(Suppl. 1): S248-S258.

Bray, M., Hatfill, S., Hensley, L., and Huggins, J. W. (2001). Haematological, biochemical and coagulation changes in mice, guinea-pigs and monkeys infected with a mouse-adapted variant of Ebola Zaire virus. J. Comp. Pathol. 125, 243-253.

Brito, L. A. and O'Hagan, D. T., Designing and Building the Next Generation of Improved Vaccine Adjuvants. J. Control. Release, 2014 190(C): 563-579.

Buge, S. L.; Richardson, E.; Alipanah, S.; Markham, P.; Cheng, S.; Kalyan, N.; Miller, C. J.; Lubeck, M.; Udem, S.; Eldridge, J.; Robert-Guroff, M.An Adenovirus-Simian Immunodeficiency Virus Env Vaccine Elicits Humoral, Cellular, and Mucosal Immune Responses in Rhesus Macaques and Decreases Viral Burden Following Vaginal Challenge J. Virol. 1997, 71 (11) 8531-8541

Bukh, I.; Calcedo, R.; Roy, S.; Carnathan, D. G.; Grant, R.; Qin, Q.; Boyd, S.; Ratcliffe, S. J.; Veeder, C. L.; Bellamy, S. L.; Betts, M. R.; Wilson, J. M.Increased Mucosal CD4+ T Cell Activation in Rhesus Macaques Following Vaccination with an Adenoviral Vector J. Virol. 2014, 88 (15) 8468-8478

Callahan, S. M., Boquet, M. P., Ming, X., Brunner, L. J., and Croyle, M. A., Impact of Transgene Expression on Drug Metabolism Following Systemic Adenoviral Vector Administration. J. Gene Med., 2006 8(5): 566-576.

Callahan, S. M., Wonganan, P., Obenauer-Kutner, L. J., Sutjipto, S., Dekker, J. D., and Croyle, M. A., Controlled Inactivation of Recombinant Viruses with Vitamin B2. J. Virol. Methods., 2008 148(1-2): 132-145.

Capone, S.; D'alise, A. M.; Ammendola, V.; Colloca, S.; Cortese, R.; Nicosia, A.; Folgori, A.Development of Chimpanzee Adenoviruses as Vaccine Vectors: Challenges and Successes Emerging from Clinical Trials Expert. Rev. Vaccines 2013, 12 (4) 379-393

Carter, N. J., Curran, M. P., Live Attenuated Influenza Vaccine (Flumist®; Fluenz™): A Review of Its Use in the Prevention of Seasonal Influenza in Children and Adults. Drugs 2011 71(12): 1591-1622.

Cerboni, S., Gentili, M., and Manel, N., Diversity of Pathogen Sensors in Dendritic Cells. Adv. Immunol., 2013 120: 211-237.

Chan, M.Ebola Virus Disease in West Africa-No Early End to the Outbreak N. Engl. J. Med. 2014,371(13) 1183-1185

Chen, D., and Kristensen, D. (2009). Opportunities and challenges of developing thermostable vaccines. Expert Rev. Vaccines. 8(5): 547-557.

Choi, J. H.; Croyle, M. A.Emerging Targets and Novel Approaches to Ebola Virus Prophylaxis and Treatment BioDrugs 2013, 27 (6) 565-583

Choi, J. H.; Schafer, S. C.; Freiberg, A. L.; Croyle, M. A. Bolstering Components of the Immune Response Compromised by Prior Exposure to Adenovirus: Guided Formulation Development for a Nasal Ebola Vaccine. Mol. Pharmaceutics 2014, submitted Choi, J. H.; Schafer, S. C.; Zhang, L.; Juelich, T.; Freiberg, A. N.; Croyle, M. A.Modeling Pre-Existing Immunity to Adenovirus in Rodents: Immunological Requirements for Successful Development of a Recombinant Adenovirus Serotype 5-Based Ebola Vaccine Mol. Pharmaceutics 2013, 10 (9) 3342-3355

Choi, J. H.; Schafer, S. C.; Zhang, L.; Kobinger, G. P.; Juelich, T.; Freiberg, A. N.; Croyle, M. A. A Single Sublingual Dose of an Adenovirus-Based Vaccine Protects against Lethal Ebola Challenge in Mice and Guinea Pigs Mol. Pharmaceutics 2012, 9 (1) 156-167

Choi, J. H., Croyle, M. A., Development of Intranasal Formulations for a Human Adenovirus Serotype 5-Based Vaccine with Potential to Bypass Pre-Existing Immunity. Mol. Ther., 2012 20 (Supplement 1): S176.

Choi, J. H., Dekker, J., Schafer, S. C., John, J., Whitfill, C. E., Petty, C. S., Haddad, E. E., and Croyle, M. A., Optimized Adenovirus-Antibody Complexes Stimulate Strong Cellular and Humoral Immune Responses against an Encoded Antigen in Naive Mice and Those with Preexisting Immunity. Clin. Vaccine Immunol., 2012 19(1): 84-95.

Choi, J. H., Jonsson-Schmunk, K., Qiu, X., Shedlock, D. J., Strong, J., Xu, J. X., Michie, K. L., Audet, J., Fernando, L., Myers, M. J., Weiner, D., Bajrovic, I., Tran, L. Q., Wong, G., Bello, A., Kobinger, G. P., Schafer, S. C., and Croyle, M. A., A Single Dose Respiratory Recombinant Adenovirus-Based Vaccine Provides Long-Term Protection for Non-Human Primates from Lethal Ebola Infection. Mol. Pharm., 2014 Nov. 14: ePub ahead of print DOI: 10.1021/mp500646d.

Choi, J. H., Schafer, S. C., Zhang, L., Juelich, T., Freiberg, A. N., and Croyle, M. A., Modeling Pre-Existing Immunity to Adenovirus in Rodents: Immunological Requirements for Successful Development of a Recombinant Adenovirus Serotype 5-Based Ebola Vaccine. Mol. Pharm., 2013 3(10): 3342-3355.

Choi, J. H., Schafer, S. C., Zhang, L., Kobinger, G. P., Juelich, T., Freiberg, A. N., and Croyle, M. A., A Single Sublingual Dose of an Adenovirus-Based Vaccine Protects against Lethal Ebola Challenge in Mice and Guinea Pigs. Mol. Pharm., 2012 9(1): 156-167.

Clark, D. V.; Jahrling, P. B.; Lawler, J. V.Clinical Management of Filovirus-Infected Patients Viruses 2012, 4 (9) 1668-1688

Coffman, R. L., Sher, A., and Seder, R. A., Vaccine Adjuvants: Putting Innate Immunity to Work. Immunity, 2010 33(4): 492-503.

Cohen, J. Infectious Disease. Ebola Vaccines Racing Forward at Record Pace Science 2014, 345 (6202) 1228-1229

Colloca, S.; Barnes, E.; Folgori, A.; Ammendola, V.; Capone, S.; Cirillo, A.; Siani, L.; Naddeo, M.; Grazioli, F.; Esposito, M. L.; Ambrosio, M.; Sparacino, A.; Bartiromo, M.; Meola, A.; Smith, K.; Kurioka, A.; O'hara, G. A.; Ewer, K. J.; Anagnostou, N.; Bliss, C.; Hill, A. V.; Traboni, C.; Klenerman, P.; Cortese, R.; Nicosia, A.Vaccine Vectors Derived from a Large Collection of Simian Adenoviruses Induce Potent Cellular Immunity across Multiple Species Sci. Transl. Med. 2012, 4 (115) 115ra2

Connolly, B. M., Steele, K. E., Davis, K. J., Geisbert, T. W., Kell, W. M., Jaax, N. K., and Jahrling, P. B. (1999). Pathogenesis of experimental Ebola virus infection in guinea pigs. J. Infect. Dis. 1999 February; 179 Suppl 1:S203-17. 179, S203-S207.

Cook, J. D., Lee, J. E., The Secret Life of Viral Entry Glycoproteins: Moonlighting in Immune Evasion PLoS Pathog., 2013 9(5): e1003258.

Costantino, H. R., Ilium, L., Brandt, G., Johnson, P. H., and Quay, S. C. (2007). Intranasal delivery: physicochemical and therapeutic aspects. Int. J. Pharm. 337(1-2): 1-24.

Croyle, M. A., Patel, A., Tran, K. N., Gray, M., Zhang, Y., Strong, J. E., Feldmann, H., and Kobinger, G. P. (2008). Nasal delivery of an adenovirus-based vaccine bypasses pre-existing immunity to the vaccine carrier and improves the immune response in mice. PLoS One 3(10): e3548.

Croyle, M. A., Le, H. T., Linse, K. D., Cerullo, V., Toietta, G., Beaudet, A., and Pastore, L., PEGylated Helper- Dependent Adenoviral Vectors: Highly Efficient Vectors with an Enhanced Safety Profile. Gene Ther., 2005 12(7): 579-587.

Croyle, M. A., Cheng, X., Sandhu, A., and Wilson, J. M., Development of Novel Formulations That Enhance Adenoviral-Mediated Gene Expression in the Lung in Vitro and in Vivo. Mol. Ther., 2001 4.(1): 22-28.

Croyle, M. A., Chirmule, N., Zhang, Y., and Wilson, J. M., "Stealth" Adenoviruses Blunt Cell-Mediated and Humoral Immune Responses against the Virus and Allow for Significant Gene Expression Upon Readministration in the Lung. J. Virol., 2001 75(10): 4792-4801.

Croyle, M. A., Patel, A., Tran, K. N., Gray, M., Zhang, Y., Strong, J. E., Feldmann, H., and Kobinger, G. P., Nasal Delivery of an Adenovirus-Based Vaccine Bypasses Pre-Existing Immunity to the Vaccine Carrier and Improves the Immune Response in Mice. PLoS One, 2008 3(10): e3548.

Croyle, M. A., Yu, Q. C., and Wilson, J. M., Development of a Rapid Method for the PEGylation of Adenoviruses with Enhanced Transduction and Improved Stability under Harsh Storage Conditions. Hum. Gene Ther., 2000 11(12): 1713-1722.

Czerkinsky, C.; Holmgren, J.Mucosal Delivery Routes for Optimal Immunization: Targeting Immunity to the Right Tissues Curr. Top. Microbiol. Immunol. 2012, 354, 1-18

Danhier, F., Ansorena, E., Silva, J. M., Coco, R., Le Breton, A., and Préat, V., PLGA-Based Nanoparticles: An Overview of Biomedical Applications. J. Control. Release, 2012 161(2): 505-522.

De Gregorio, E., Rappuoli, R., From Empiricism to Rational Design: A Personal Perspective of the Evolution of Vaccine Development. Nat. Rev. Immunol., 2014 4(7): 505-514.

Dejupesland, P. G., Nasal Drug Delivery Devices: Characteristics and Performance in a Clinical Perspective—a Review. Drug Deliv. and Transl. Res., 2013 3(1): 42-62.

Delany, I., Rappuoli, R., and De Gregorio, E., Vaccines for the 21st Century. EMBO Mol. Med., 2014 6(6): 708-720.

Della Pia, E. A., Hansen, R. W., Zoonens, M., and Martinez, K. L., Functionalized Amphipols: A Versatile Toolbox Suitable for Applications of Membrane Proteins in Synthetic Biology. J. Membr. Biol., 2014 247(9-10): 815-826.

Desvignes, C., Esteves, F., Etchart, N., Bella, C., Czerkinsky, C., and Kaiserlian, D. (1998). The murine buccal mucosa is an inductive site for priming class I-restricted CD8+ effector T cells in vivo. Clin. Exp. Immunol. 113(3): 386-393.

Dhere, R., Yeolekar, L., Kulkarni, P., Menon, R., Vaidya, V., Ganguly, M., Tyagi, P., Barde, P., and Jadhav, S., A Pandemic Influenza Vaccine in India: From Strain to Sale within 12 Months. Vaccine, 2011 29 (Suppl. 1): A16-A21.

Djupesland, P. G.Nasal Drug Delivery Devices: Characteristics and Performance in a Clinical Perspective—a Review Drug Deliv. Transl. Res. 2013, 3 (1) 42-62

Ducusin, J., Narvaez, D., Wilburn, S., Mahmoudi, F., Orris, P., Sobel, H., Bersola, E., and Ricardo, M. (2004). Waste Management and Disposal During the Philippine Follow-Up Measles Campaign. Washington, D.C., U.S.A. and Manilla, Phillipines, Health Care without Harm and the Philippine Department of Health: 1-112.

Duerr, A.; Huang, Y.; Buchbinder, S.; Coombs, R. W.; Sanchez, J.; Del Rio, C.; Casapia, M.; Santiago, S.; Gilbert, P.; Corey, L.; Robertson, M. N.; STEP/HVTN 504 Study Team.Extended Follow-up Confirms Early Vaccine-Enhanced Risk of HIV Acquisition and Demonstrates Waning Effect over Time among Participants in a Randomized Trial of Recombinant Adenovirus HIV Vaccine (STEP Study) J. Infect. Dis. 2012, 206 (2) 258-266

Ebola Haemmorrhagic Fever in Zaire, 1976. Bull. W.H.O. 1978, 56 (2), 271-292.

Ebola Outbreak in West Africa. 2014; Centers for Disease Control and Prevention: Atlanta, Ga., cdc.gov/vhf/ebola/outbreaks/guinea/index.html.

Expert Rev. Vaccines. 8(8): 1083-1097.

Fanning, S. L., Appel, M. Y., Berger, S. A., Korngold, R., Friedman, T. M., The Immunological Impact of Genetic Drift in the B10.Br Congenic Inbred Mouse Strain. J. Immunol., 2009 183(7): 4261-4272.

Fenimore, P. W., Muhammad, M. A., Fischer, W. M., Foley, B. T., Bakken, R. R., Thurmond, J. R., Yusim, K., Yoon, H., Parker, M., Hart, M. K., Dye, J. M., Korber, B., and Kuiken, C., Designing and Testing Broadly-Protective Filoviral Vaccines Optimized for Cytotoxic T-Lymphocyte Epitope Coverage. PLoS One, 2012 7(10): e44769.

Fortuna, A., Alves, G., Serralheiro, A., Sousa, J., and Falcao, A., Intranasal Delivery of Systemic-Acting Drugs: Small-Molecules and Biomacromolecules. Eur. J. Pharm. Biopharm., 2014 Mar. 28(ePub ahead of print).

Fowler, R. A.; Fletcher, T.; Fischer, I.; W. A; Lamontagne, F.; Jacob, S.; Brett-Major, D.; Lawler, J. V.; Jacquerioz, F. A.; Houlihan, C.; O'Dempsey, T.; Ferri, M.; Adachi, T.; Lamah, M. C.; Bah, E. I.; Mayet, T.; Schieffelin, J.; Mclellan, S. L.; Senga, M.; Kato, Y.; Clement, C.; Mardel, S.; Vallenas Bejar De Villar, R. C.; Shindo, N.; Bausch, D.Caring for Critically Ill Patients with Ebola Virus Disease: Perspectives from West Africa Am. J. Respir. Crit. Care Med. 2014, 90 (7) 733-737

Fraser, K. A., Schenkel, J. M., Jameson, S. C., Vezys, V., and Masopust, D., Pre-Existing High Frequencies of Memory CD8+ T Cells Favor Rapid Memory Differentiation and Preservation of Proliferative Potential Upon Boosting. Immunity, 2013 39(1): 171-183.

Ftika, L.; Maltezou, H. C.Viral Haemorrhagic Fevers in Healthcare Settings J. Hosp. Infect. 2013, 83 (3) 185-192

Geber, W. F., Lefkowitz, S. S., and Hung, C. Y. (1977). Duration of interferon inhibition following single and multiple injections of morphine. J. Toxicol. Environ. Health. 2, 577-582.

Geisbert, T. W., Pushko, P., Anderson, K., Smith, J., Davis, K. J., and Jahrling, P. B. (2002). Evaluation in nonhuman primates of vaccines against Ebola virus. Emerg Infect Dis 8, 503-507.

Geisbert, T. W., Bailey, M., Hensley, L., Asiedu, C., Geisbert, J., Stanley, D., Honko, A., Johnson, J., Mulangu, S., Pau, M. G., Custers, J., Vellinga, J., Hendriks, J., Jahrling, P., Roederer, M., Goudsmit, J., Koup, R., and Sullivan, N. J., Recombinant Adenovirus Serotype 26 (Ad26) and Ad35 Vaccine Vectors Bypass Immunity to Ad5 and Protect Nonhuman Primates against Ebolavirus Challenge. J. Virol., 2011 85(9): 4222-4233.

General Chapter <71> Sterility Tests. In The United States Pharmacopiea (37th Rev.) and the National Formulary, 32nd ed.; The United States Pharmacopeial Convention: Rockville, Md., 2014; pp 71-77.

Gerdes, J.; Schwab, U.; Lemke, H.; Stein, H.Production of a Mouse Monoclonal Antibody Reactive with a Human Nuclear Antigen Associated with Cell Proliferation Int. J. Cancer 1983, 31 (1) 13-20

Gilbert, R.; Guilbault, C.; Gagnon, D.; Bernier, A.; Bourget, L.; Elahi, S. M.; Kamen, A.; Massie, B.Establishment and Validation of New Complementing Cells for Production of E1-Deleted Adenovirus Vectors in Serum-Free Suspension Culture J. Virol. Methods 2014, 208, 177-178

Giudice, E. L., and Campbell, J. D. (2006). Needle-free vaccine delivery. Adv. Drug Deliv. Rev. 58(1): 68-89.

Gray, G. E.; Moodie, Z.; Metch, B.; Gilbert, P. B.; Bekker, L. G.; Churchyard, G.; Nehabeleng, M.; Mlisana, K.; Laher, F.; Roux, S.; Mngadi, K.; Innes, C.; Mathebula, M.; Allen, M.; Mcelrath, M. J.; Robertson, M.; Kublin, J.; Corey, L.; HVTN 503/Phambili Study Team.Recombinant Adenovirus Type 5 HIV Gag/Pol/Nef Vaccine in South Africa: Unblinded, Long-Term Follow-up of the Phase 2b HVTN 503/Phambili Study Lancet Infect. Dis. 2014, 14 (5) 388-396

Gregory, A. E., Titball, R., and Williamson, D., Vaccine Delivery Using Nanoparticles. Front. Cell Infect. Microbiol., 2013 3: 13.

Hassan, N., Ahad, A., Ali, M., and Ali, J. (2010). Chemical permeation enhancers for transbuccal drug delivery.Expert Opin Drug Deliv. 7(1): 97-112.

Hill, M. W. (1984). Cell Renewal in Oral Epithelia. The Structure and Function of Oral Mucosa. J. Meyer, Squier, C. A., Gerson, S. J., Eds. New York, Pergamon.

Hoenen, T., Groseth, A., and Feldmann, H., Current Ebola Vaccines. Expert. Opin. Biol. Ther., 2012 12(7): 859-872.

Hokey, D. A.; Johnson, F. B.; Smith, J.; Weber, J. L.; Yan, J.; Hirao, L.; Boyer, J. D.; Lewis, M. G.; Makedonas, G.; Betts, M. R.; Weiner, D. B.Activation Drives PD-1 Expression During Vaccine-Specific Proliferation and Following Lentiviral Infection in Macaques Eur. J. Immunol. 2008, 38 (5) 1435-1445

Holmgren, J., Svennerholm, A. M., Vaccines against Mucosal Infections. Curr. Opin. Immunol; 2012 24(3): 343-353.

Hung, C. Y., Lefkowitz, S. S, and Geber, W. F. (1973). Interferon inhibition by narcotic analgesics. Proc. Soc. Exp. Biol. Med. 142, 106-111.

Hurwitz, J. L., Respiratory Syncytial Virus Vaccine Development. Expert Rev. Vaccines, 2011 10(10): 1415-1433.

Hutton, G., and Tediosi, F. (2006). The costs of introducing a malaria vaccine through the expanded program on immunization in Tanzania. Am. J. Trop. Med. Hyg. 75(2 Suppl.): 119-130.

Ibrahim, J., Gerson, S. J., and Meyer, J. (1985). Frequency and distribution of binucleate cells in oral epithelium of several species of laboratory rodents. Arch. Oral Biol. 30(8): 627-633.

Ingulli, E. (2007). Tracing tolerance and immunity in vivo by CFSE-labeling of administered cells. Methods Mol. Biol. 380: 365-376.

Jacobsen, J., Nielsen, E. B., Brondum-Nielsen, K., Christensen, M. E., Olin, H. B., Tommerup, N., Rassing, M. R. (1999). Filter-grown TR146 cells as an in vitro model of human buccal epithelial permeability. Eur. J. Oral Sci. 107(2): 138-146.

Jacobson, R. M., Swan, A., Adegbenro, A., Ludington, S. L., Wollan, P. C., and Poland, G. A. (2001). Making vaccines more acceptable—methods to prevent and minimize pain and other common adverse events associated with vaccines. Vaccine 19(17-19): 2418-2427.

Jain, S., O'Hagan, D. T., and Singh, M., The Long-Term Potential of Biodegradable Poly(Lactide-Co-Glycolide) Microparticles as the Next-Generation Vaccine Adjuvant. Expert Rev. Vaccines., 2011 10(12): 1731-1742.

Johnson, K. M.; Lange, J. V.; Webb, P. A.; Murphy, F. A.Isolation and Partial Characterisation of a New Virus Causing Acute Haemorrhagic Fever in Zaire Lancet 1977, 1 (8011) 569-571

Kane, A., Lloyd, J., Zaffran, M., Simonsen, L., and Kane, M. (1999). Transmission of hepatitis B, hepatitis C and human immunodeficiency viruses through unsafe injections in the developing world: model-based regional estimates.Bull. World Health Organ. 77(10): 801-807.

Klessig, D. F.; Grodzicker, T.Mutations That Allow Human Ad2 and Ad5 to Express Late Genes in Monkey Cells Map in the Viral Gene Encoding the 72k DNA Binding Protein Cell 1979, 17 (4) 957-966

Kobinger, G. P., Feldmann, H., Zhi, Y., Schumer, G., Gao, G., Feldmann, F., Jones, S., and Wilson, J. M. (2006). Chimpanzee adenovirus vaccine protects against Zaire Ebola virus. Virology 346(2): 394-401.

Kolate, A., Baradia, D., Patil, S., Vhora, I., Kore, G., and Misra, A., PEG—A Versatile Conjugating Ligand for Drugs and Drug Delivery Systems. J. Control. Release, 2014 192(C): 67-81.

Kraan, H.; Vrieling, H.; Czerkinsky, C.; Jiskoot, W.; Kersten, G.; Amorij, J. P.Buccal and Sublingual Vaccine Delivery J. Controlled Release 2014, 190, 580-592

Kupferschmidt, K.Infectious Disease. Estimating the Ebola Epidemic Science 2014, 345 (6201) 1108

Langer, R., Polymeric Delivery Systems for Controlled Drug Release. Chem. Eng. Communicat., 1980 6(1-3): 1-48.

Le Bon, C., Popot, J. L., and Giusti, F., Labeling and Functionalizing Amphipols for Biological Applications. J. Mebr. Biol., 2014 247(9-10): 797-814.

Ledgerwood, J. E., Dezure, A. D., Stanley, D. A., Novik, L., Enama, M. E., Berkowitz, N. M., Hu, Z., Joshi, G., Ploquin, A., Sitar, S., Gordon, I. J., Plummer, S. A., Holman, L. A., Hendel, C. S., Yamshchikov, G., Roman, F., Nicosia, A., Colloca, S., Cortese, R., Bailer, R. T., Schwartz, R. M., Roederer, M., Mascola, J. R., Koup, R. A., Sullivan, N. J., Graham, B. S. And the VRC 207 Study Team., Chimpanzee Adenovirus Vector Ebola Vaccine— Preliminary Report. N. Engl. J. Med., 2014 Nov. 26: ePub ahead of print.

Lee, J. E., Fusco, M. L., and Ollman-Saphire, E., An Efficient Platform for Screening Expression and Crystallization of Glycoproteins Produced in Human Cells. Nat. Protoc., 2009 4(4): 592-604.

Lerner, S. P., Anderson, C. P., Harrison, D. E., Walford, R. L., and Finch, C. E., Polygenic Influences on the Length of Oestrous Cycles in Inbred Mice Involve MHC Alleles. Eur. J. Immunogenet., 1992 19(6): 361-371.

Levine, M. M., and Robins-Browne, R. (2009). Vaccines, global health and social equity. Immunol. Cell Biol. 87(4): 274-278.

Littman, R. J., The Plauge of Athens: Epidemiology and Paleopathology. Mt. Siani J. Med., 2009 76(5): 456-467.

MacNeil, A. and Rollin, P. E., Ebola and Marburg Hemorrhagic Fevers: Neglected Tropical Diseases? PLoS Negl. Trop. Dis., 2012 6(6): e1546.

Majhen, D.; Calderon, H.; Chandra, N.; Fajardo, C. A.; Rajan, A.; Alemany, R.; Custers, J.Adenovirus-Based Vaccines for Fighting Infectious Diseases and Cancer: Progress in the Field Hum. Gene Ther. 2014, 25 (4) 301-317

Makedonas, G.; Betts, M. R.Polyfunctional Analysis of Human T Cell Responses: Importance in Vaccine Immunogenicity and Natural Infection Springer Semin. Immunopathol. 2006, 28 (3) 209-219

Mao, S., Cun, D., and Kawaashima, Y. (2009). Novel Non-Injectable Formulation Approaches of Peptides and Proteins. Delivery Technologies for Biopharmaceuticals Peptides, Proteins, Nucelic Acids and Vaccines. L. Jorgensen, and Nielsen, H. M., Eds. West Sussex, United Kingdom, John Wiley & Sons Ltd.: 29-67.

Marie, E., Sagan, S., Cribier, S., and Tribet, C., Amphiphilic Macromolecules on Cell Membranes: From Protective Layers to Controlled Permeabilization. J. Mebr. Biol., 2014 47(9-10): 861-881.

Marone, G., Stellato, C., Mastronardi, P., Mazzarella, B. (1993). Mechanisms of activation of human mast cells and basophils by general anesthetic drugs. Ann. Fr. Anesth. Reanim. 12, 116-125.

Marzi, A., Engelmann, F., Feldmann, F., Haberthur, K., Shupert, W. L., Brining, D., Scott, D. P., Geisbert, T. W., Kawaoka, Y., Katze, M. G., Feldmann, H., and Messaoudi, I., Antibodies Are Necessary for rVSV/ZEBOV-GP-Mediated Protection against Lethal Ebola Virus Challenge in Nonhuman Primates. Proc. Natl. Acad. Sci. U.S.A, 2013 110(5): 1893-1898.

Marzi, A.; Feldmann, H.Ebola Virus Vaccines: An Overview of Current Approaches Expert Rev. Vaccines 2014, 13 (4) 521-531

Matthias, D. M., Robertson, J., Garrison, M. M., Newland, S., and Nelson, C. (2007). Freezing temperatures in the vaccine cold chain: a systematic literature review. Vaccine 25(20): 3980-3986.

Mcallister, S. C., Schleiss, M. R., Prospects and Perspectives for Development of a Vaccine against Herpes Simplex Virus Infections. Expert Rev. Vaccines, 2014 13(11): 1349-1360

Meltzer, M. I.; Atkins, C. Y.; Santibanez, S.; Knust, B.; Petersen, B. W.; Ervin, E. D.; Nichol, S. T.; Damon, I. K.; Washington, M. L.Estimating the Future Number of Cases in the Ebola Epidemic-Liberia and Sierra Leone, 2014-2015 MMWR Surveill. Summ. 2014, 63 (3) 1-14

Mutsch, M., Zhou, W., Rhodes, P., Bopp, M., Chen, R. T., Linder, T., Spyr, C., and Steffen, R. (2004). Use of the inactivated intranasal influenza vaccine and the risk of Bell's palsy in Switzerland. N. Engl. J. Med. 350(9): 896-903.

Nakayama, E., Saijo, M., Animal Models for Ebola and Marburg Virus Infections. Front. Microbiol., 2013 4(267).

Nir, Y., Paz, A., Sabo, E., and Potasman, 1. (2003). Fear of injections in young adults: prevalence and associations. Am. J. Trop. Med. Hyg. 68(3): 341-344.

Nwanegbo, E., Vardas, E., Gao, W., Whittle, H., Sun, H., Rowe, D., Robbins, P. D., and Gambotto, A. (2004). Prevalence of neutralizing antibodies to adenoviral serotypes 5 and 35 in the adult populations of The Gambia, South Africa, and the United States. Clin. Diagn. Lab Immunol. 11(2): 351-357.

Ong, H. X., Traini, D., and Young, P. M., Pharmaceutical Applications of the Calu-3 Lung Epithelia Cell Line. Expert Opin. Drug Deliv., 2013 10(9): 1287-1302.

Patel, A., Zhang, Y., Croyle, M., Tran, K., Gray, M., Strong, J., Feldmann, H., Wilson, J. M., and Kobinger, G. P., Mucosal Delivery of Adenovirus-Based Vaccine Protects against Ebola Virus Infection in Mice. J. Infect. Dis., 2007 96(Suppl. 2): S413-S420.

Pather, S. I., Rathbone, M. J., and Senel, S. (2008). Current status and the future of buccal drug delivery systems. Expert Opin. Drug Deliv. 5(5): 531-542.

Pavot, V.; Rochereau, N.; Genin, C.; Verrier, B.; Paul, S.New Insights in Mucosal Vaccine Development Vaccine 2012, 30 (2) 142-154

Piersma, F. E., Daemen, M. A., Bogaard, A. E., and Buurman, W. A. (1999). Interference of pain control employing opioids in in vivo immunological experiments. Lab Animal 33, 328-333.

Pratheek, B. M., Saha, S., Maiti, P. K., Chattopadhyay, S., and Chattopadhyay, S., Immune Regulation and Evasion of Mammalian Host Cell Immunity During Viral Infection. Indian J. Virol., 2013 24(1): 1-15.

Prüss-Ustün, A., Rapiti, E., and Hutin, Y. (2005). Estimation of the global burden of disease attributable to contaminated sharps injuries among health-care workers. Am. J. Ind. Med. 48(6): 482-490.

Qiu, X., Audet, J., Wong, G., Pillet, S., Bello, A., Cabral, T., Strong, J. E., Plummer, F., Corbett, C. R., Alimonti, J. B., and Kobinger, G. P., Successful Treatment of Ebola Virus-Infected Cynomolgus Macaques with Monoclonal Antibodies. Sci. Transl. Med., 2012 4(138): 138ra81.

Qiu, X.; Wong, G.; Fernando, L.; Audet, J.; Bello, A.; Strong, J.; Alimonti, J. B.; Kobinger, G. P.Mabs and Ad-Vectored IFN-α Therapy Rescue Ebola-Infected Nonhuman Primates when Administered after the Detection of Viremia and Symptoms Sci. Transl. Med. 2013, 5 (207) 207ra143

Qureshi, H.; Genescà, M.; Fritts, L.; Mcchesney, M. B.; Robert-Guroff, M.; Miller, C. J.Infection with Host-Range Mutant Adenovirus 5 Suppresses Innate Immunity and Induces Systemic CD4+ T Cell Activation in Rhesus Macaques PLoS One 2014, 9 (9) e106004

Rao, M., Matyas, G. R., Grieder, F., Anderson, K., Jahrling, P. B., and Alving, C. R., Cytotoxic T Lymphocytes to Ebola Zaire Virus Are Induced in Mice by Immunization with Liposomes Containing Lipid A. Vaccine 1999 17(23-24): 2991-2998.

Rao, V. R., Upadhyay, A. K., and Kompella, U. B., pH Shift Assembly of Adenoviral Serotype 5 Capsid Protein Nanosystems for Enhanced Delivery of Nanoparticles, Proteins and Nucleic Acids. J. Control. Release, 2013 172(1): 341-350.

Reddick, L. E., Alto, N. M., Bacteria Fighting Back: How Pathogens Target and Subvert the Host Innate Immune System. Mol. Cell, 2014 54(2): 321-328.

Reed, L. J., Muench, H., A Simple Method of Estimating Fifty Percent Endpoints. Am. J. Hyg., 1938 27: 493-497.

Renteria, S. S., Clemens, C. C., and Croyle, M. A., Development of a Nasal Adenovirus-Based Vaccine: Effect of Concentration and Formulation on Adenovirus Stability and Infectious Titer During Actuation from Two Delivery Devices. Vaccine, 2010 28(9): 2137-2148.

Richardson, J. S.; Abou, M. C.; Tran, K. N.; Kumar, A.; Sahai, B. M.; Kobinger, G. P.Impact of Systemic or Mucosal Immunity to Adenovirus on Ad-Based Ebola Virus Vaccine Efficacy in Guinea Pigs J. Infect. Dis. 2011, 204 (Suppl. 3) S1032-S1042

Richardson, J. S.; Pillet, S.; Bello, A. J., and Kobinger, G. P., Airway Delivery of an Adenovirus-Based Ebola Virus Vaccine Bypasses Existing Immunity to Homologous Adenovirus in Nonhuman Primates. J. Virol., 2013 87(7): 3668-3677.

Richardson, J. S., Yao, M. K., Tran, K. N., Croyle, M. A., Strong, J. E., Feldmann, H., and Kobinger, G. P., Enhanced Protection against Ebola Virus Mediated by an Improved Adenovirus-Based Vaccine. PLoS One, 2009 4(4): e5308.

Riese, P., Sakthivel, P., Trittel, S., and Guzman, C. A., Intranasal Formulations: Promising Strategy to Deliver Vaccines. Expert Opin. Drug Deliv., 2014 Jun. 25(ePub ahead of print): 1-16.

Riese, P., Schulze, K., Ebensen, T., Prochnow, B., and Guzman, C. A., Vaccine Adjuvants: Key Tools for Innovative Vaccine Design. Current Top. Med. Chem., 2013 13(20): 2562-2580.

Rothe, C.; Schlaich, C.; Thompson, S.Healthcare-Associated Infections in Sub-Saharan Africa J. Hosp. Infect. 2013, 85 (4) 257-267

Rupniak, H. T., Rowlatt, C., Lane, E. B., Steele, J. G., Trejdosicwicz, L. K., Laskiewicz, B., Povey, S., Hill, B. T. (1985). Characteristics of four new human cell lines derived from squamous cell carcinomas of the head and neck. J. Natl. Cancer Inst. 75(4): 621-635.

Russell, K. L., Hawksworth, A. W., Ryan, M. A., Strickler, J., Irvine, M., Hansen, C. J., Gray, G. C., and Gaydos, J. C. (2006). Vaccine-preventable adenoviral respiratory illness in US military recruits, 1999-2004. Vaccine 24(15): 2835-2842.

Sallusto, F., Lanzavecchia, A., Araki, K., and Ahmed, R., From Vaccines to Memory and Back. Immunity, 2010 33(4): 451-63.

Saphire, E. O., An Update on the Use of Antibodies against the Filoviruses. Immunotherapy, 2013 5(11): 1221-1233.

Saxena, M., Van, T. T., Baird, F. J., Coloe, P. J., and Smooker, P. M., Pre-Existing Immunity against Vaccine Vectors—Friend or Foe?. Microbiology, 2013 159(1): 1-11.

Schäfer, B., Holzer, G. W., Joachimsthaler, A., Coulibaly, S., Schwendinger, M., Crowe, B. A., Kreil, T. R., Barrett, P. N., and Falkner, F. G., Pre-Clinical Efficacy and Safety of Experimental Vaccines Based on Non-Replicating Vaccinia Vectors against Yellow Fever. PLoS One, 2011 6(9): e24505.

Schieffelin, J. S.; Shaffer, J. G.; Goba, A.; Gbakie, M.; Gire, S. K.; Colubri, A.; Sealfon, R. S.; Kanneh, L.; Moigboi, A.; Momoh, M.; Fullah, M.; Moses, L. M.; Brown, B. L.; Andersen, K. G.; Winnicki, S.; Schaffner, S. F.; Park, D. J.; Yozwiak, N. L.; Jiang, P. P.; Kargbo, D.; Jalloh, S.; Fonnie, M.; Sinnah, V.; French, I.; Kovoma, A.; Kamara, F. K.; Tucker, V.; Konuwa, E.; Sellu, J.; Mustapha, I.; Foday, M.; Yillah, M.; Kanneh, F.; Saffa, S.; Massally, J. L.; Boisen, M. L.; Branco, L. M.; Vandi, M. A.; Grant, D. S.; Happi, C.; Gevao, S. M.; Fletcher, T. E.; Fowler, R. A.; Bausch, D. G.; Sabeti, P. C.; Khan, S. H.; Garry, R. F.; KGH Lassa Fever Program; Viral Hemorrhagic Fever Consortium; WHO Clinical Response Team.Clinical Illness and Outcomes in Patients with Ebola in Sierra Leone N. Engl. J. Med. 2014, Scott, L. J., Carter, N. J., and Curran, M. P., Live Attenuated Influenza Vaccine (Fluenz™): A Guide to Its Use in the Prevention of Seasonal Influenza in Children in the Eu. Paediatr. Drugs, 2012 14(4): 271-279.

Seder, R. A., Darrah, P. A., and Roederer, M., T-Cell Quality in Memory and Protection: Implications for Vaccine Design. Nat. Rev. Immunol., 2008 8(4): 247-258.

Shedlock, D. J.; Talbott, K. T.; Morrow, M. P.; Ferraro, B.; Hokey, D. A.; Muthumani, K.; Weiner, D. B.Ki-67 Staining for Determination of Rhesus Macaque T Cell Proliferative Responses Ex Vivo Cytometry A 2010, 77 (3) 275-284

Shiferaw, Y.; Abebe, T.; Mihret, A.Sharps Injuries and Exposure to Blood and Bloodstained Body Fluids Involving Medical Waste Handlers Waste Manage. Res. 2012, 30 (12) 1299-1305

Shim, B. S.; Choi, Y.; Cheon, I. S.; Song, M. K.Sublingual Delivery of Vaccines for the Induction of Mucosal Immunity Immune Network 2013, 13 (3) 81-85

Shojaei, A. H. (1998). Buccal Mucosa as a Route for Systemic Drug Delivery: A Review. J. Pharm. Pharmaceut. Sci. 1(1): 15-30.

Simonsen, L., Kane, A., Lloyd, J., Zaffran, M., and Kane, M. (1999). Unsafe injections in the developing world and transmission of bloodborne pathogens: a review. Bull. World Health Organ. 77(10): 789-800.

Soloff, A. C., Barratt-Boyes, S. M., Enemy at the Gates: Dendritic Cells and Immunity to Mucosal Pathogens Cell Res., 2010 20(8): 872-885.

Soma, L. R. (1983). Anesthetic and analgesic considerations in the experimental animal. Ann NY Acad Sci 406, 32-47.

Stanley, D. A.; Honko, A. N.; Asiedu, C.; Trefry, J. C.; Lau-Kilby, A. W.; Johnson, J. C.; Hensley, L.; Ammendola, V.; Abbate, A.; Grazioli, F.; Foulds, K. E.; Cheng, C.; Wang, L.; Donaldson, M. M.; Colloca, S.; Folgori, A.; Roederer, M.; Nabel, G. J.; Mascola, J.; Nicosia, A.; Cortese, R.; Koup, R. A.; Sullivan, N. J.Chimpanzee Adenovirus Vaccine Generates Acute and Durable Protective Immunity against Ebolavirus Challenge Nat. Med. 2014, 20 (10) 1126-1129

Stellato, C., Cirillo, R., de Paulis, A., et al. (1992). Human basophil/mast cell releasability. IX. Heterogeneity of the effects of opioids on mediator release. Anesthesiology. 77, 932-940.

Stroher, U., and Feldmann, H. (2006). Progress towards the treatment of Ebola haemorrhagic fever. Expert Opin Investig Drugs 15, 1523-1535.

Sullivan, N. J.; Hensley, L.; Asiedu, C.; Geisbert, T. W.; Stanley, D.; Johnson, J.; Honko, A.; Olinger, G.; Bailey, M.; Geisbert, J. B.; Reimann, K. A.; Bao, S.; Rao, S.; Roederer, M.; Jahrling, P. B.; Koup, R. A.; Nabel, G. J.CD8+ Cellular Immunity Mediates Rad5 Vaccine Protection against Ebola Virus Infection of Nonhuman Primates Nat. Med. 2011, 17 (9) 1128-1131

Sullivan, N. J., Geisbert, T. W., Geisbert, J. B., Xu, L., Yang, Z. Y., Roederer, M., Koup, R. A., Jahrling, P. B., and Nabel, G. J., Accelerated Vaccination for Ebola Virus Haemorrhagic Fever in Non-Human Primates. Nature, 2003 424(6949): 681-684.

Thacker, E. E., Timares, L., Matthews, Q. L. (2009). Strategies to overcome host immunity to adenovirus vectors in vaccine development. Expert Rev. Vaccines. 8(6): 761-777.

Vasconcelos, J. R.; Dominguez, M. R.; Araújo, A. F.; Ersching, J.; Tararam, C. A.; Bruna-Romero, O.; Rodrigues, M. M.Relevance of Long-Lived CD8(+) T Effector Memory Cells for Protective Immunity Elicited by Heterologous Prime-Boost Vaccination Front. Immunol. 2012, 3, 358

Weaver, E. A., Barry, M. A., Effects of Shielding Adenoviral Vectors with Polyethylene Glycol on Vector Specific and Vaccine Mediated Immune Responses. Hum. Gene Ther., 2008 19(12): 1369-1382.

Wertz, P. W., and Squier, C. A. (1991). Cellular and molecular basis of barrier function in oral epithelium. Crit. Rev. Ther. Drug Carrier Syst. 8(3): 237-269.

Wong, G., Kobinger, G., and Qiu, X., Characterization of Host Immune Responses in Ebola Virus Infections. Expert Rev. Clin. Immunol., 2014 10(6): 781-790.

Wong, G., Richardson, J. S., Pillet, S., Patel, A., Qiu, X., Alimonti, J., Hogan, J., Zhang, Y., Takada, A., Feldmann, H., and Kobinger, G. P., Immune Parameters Correlate with Protection against Ebola Virus Infection in Rodents and Nonhuman Primates. Sci. Transl.Med., 2012 4(158): 158ra146.

Wong, G.; Audet, J.; Fernando, L.; Fausther-Bovendo, H.; Alimonti, J. B.; Kobinger, G. P.; Qiu, X.Immunization with Vesicular Stomatitis Virus Vaccine Expressing the Ebola Glycoprotein Provides Sustained Long-Term Protection in Rodents Vaccine 2014, 32 (43) 5722-5729

Wong, G.; Qiu, X.; Olinger, G. G.; Kobinger, G. P.Post-Exposure Therapy of Filovirus Infections Trends Microbiol. 2014, 22 (8) 456-463

Wonganan, P., Clemens, C. C., Brasky, K., Pastore, L., and Croyle, M. A., Species Differences in the Pharmacology and Toxicology of PEGylated Helper-Dependent Adenovirus. Mol. Pharm., 2011 8(1): 78-92.

Wonganan, P., Croyle, M. A., PEGylated Adenoviruses: From Mice to Monkeys. Viruses, 2010 2(2):468-502(2): 468-502.

World Health Organization, (2005). Management of solid health-care waste at primary health-care centres: a decision-making guide. Department of Immunization, Vaccines and Biologicals (IVB), Protection of the Human Environment Water, Sanitation and Health (WSH) Immunization, Protection of the Human Environment Water, Sanitation and Health (WSH). Geneva, Switzerland, World Health Organization: 1-53.

World Health Organization, UNICEF, and World Bank. (2009). State of the World's Vaccines and Immunization. Geneva, Switzerland, World Health Organization.

World Health Organization. Ebola Response Roadmap Situation Report 29 Oct. 2014; World Health Organization: Geneva, Switzerland, 2014; pp 1-10.

Yuki, Y., and Kiyono, H. (2009). Mucosal vaccines: novel advances in technology and delivery.

Zaman, M., Chandrudu, S., and Toth, I., Strategies for Intranasal Delivery of Vaccines. Drug Deliv. and Transl. Res., 2013 3(1): 100-109.

Zhou, W., Pool, V., DeStefano, F., Iskander, J. K., Haber, P., and Chen, R. T. (2004). A potential signal of Bell's palsy after parenteral inactivated influenza vaccines: reports to the Vaccine Adverse Event Reporting System (VAERS)—United States, 1991-2001. Pharmacoepidemiol. Drug Saf. 13(8): 505-510.

Zielinski, C. E., Corti, D., Mele, F., Pinto, D., Lanzavecchia, A., and Sallusto, F., Dissecting the Human Immunologic Memory for Pathogens. Immunol. Rev., 2011 240(1): 40-51.

---

What is claimed is:

1. A composition comprising a recombinant viral vector comprising an expression cassette encoding a heterologous polypeptide, said recombinant viral vector formulated in a substantially solid carrier that is dissolvable upon contact with an aqueous solution, comprising: (i) PMAL-C16 or (ii) from about 0.1% to 10% of a zwitterionic surfactant.

2. The composition of claim 1, wherein the aqueous solution is saliva.

3. A method for inducing long-term immunity to a pathogen in a subject comprising administering an effective amount of a recombinant viral vector comprising an expression cassette encoding an antigen of the pathogen, formulated in a pharmaceutically acceptable liquid carrier comprising: (i) PMAL-C16 or (ii) from about 0.1% to 10% of a zwitterionic surfactant, to the subject.

4. The method of claim 3, wherein the subject has pre-existing immunity to the viral vector.

5. The method of claim 3, wherein the pathogen is a virus or a bacteria.

6. A method for delivering a recombinant viral vector encoding a heterologous polypeptide to a subject, comprising administering to the subject the recombinant viral vector formulated in a pharmaceutically acceptable liquid carrier comprising: (i) PMAL-C16 or (ii) from about 0.1% to 10% of a zwitterionic surfactant.

7. The method of claim 6, wherein the subject is a primate.

8. The method of claim 6, wherein the subject has pre-existing immunity to the viral vector.

9. A method for generating an immune response to an antigen in a primate comprising, administering to the primate an effective amount of a recombinant viral vector comprising an expression cassette encoding the antigen formulated in a pharmaceutically acceptable liquid carrier comprising: (i) PMAL-C16 or (ii) from about 0.1% to 10% of a zwitterionic surfactant.

10. The method of claim 9, wherein the primate has pre-existing immunity to the recombinant viral vector.

11. The method of claim 9, wherein the antigen is derived from a virus or bacteria.

12. A method of increasing transduction efficiency of a recombinant viral vector in a subject comprising, administering to the subject the recombinant viral vector formulated in a pharmaceutically acceptable carrier comprising (i) PMAL-C16 or (ii) from about 0.1% to 10% of a zwitterionic surfactant.

13. The method of claim 12, wherein the subject is a primate.

14. The method of claim 12, wherein the carrier is a liquid carrier.

15. The method of claim 12, wherein the carrier is a substantially solid carrier.

16. A method of making a stabilized recombinant viral vector composition comprising:

(a) formulating a solution comprising the recombinant viral vector comprising an expression cassette encoding a heterologous antigen, derived from a virus or a bacteria, in a pharmaceutically acceptable carrier said carrier comprising:

(i) PMAL-C16; or (ii) from about 0.1% to 10% of a zwitterionic surfactant; and (b) drying the solution to provide a stabilized recombinant viral vector composition in a substantially solid amorphous carrier.

17. The method of claim 16, wherein the recombinant viral vector is an enveloped virus.

18. The method of claim 16, wherein the recombinant viral vector is a non-enveloped virus.

19. The method of claim 16, wherein the virus from which the heterologous antigen is derived is selected from the group consisting of Arenavirus, Arterivirus, Astrovirus, Birnavirus, Bunyavirus, Calicivirus, Coronavirus, Deltavirus, Filovirus, Flavivirus, Hepadnavirus, Herpesvirus, Orthomyxovirus, Papovavirus, Paramyxovirus, Picornavirus, Poxyiridae, Reovirus, Retrovirus, Rhabdovirus, and Togavirus.

20. The method of claim 16, wherein the bacteria from which the heterologous antigen is derived is selected from the group consisting of *Streptococcus* agalacaae, *Legionella* pneumophilia, *Streptococcus pyogenes, Escherichia coli, Neisseria gonorrhosae, Neisseria meningitidis*, Pneumococcus, Hemophilis *influenzae* B, *Treponema pallidum*, Lyme disease spirochetes, *Pseudomonas aeruginosa, Mycobacterium leprae, Brucella abortus, Mycobacterium tuberculosis, Plasmodium falciparum, Plasmodium vivax, Toxoplasma gondii*, Trypanosoma *rangeli*, Trypanosoma *cruzi*, Trypanosoma rhodesiensei, Trypanosoma *brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium, M. pneumoniae, Candida albicans, Cryptococcus neoformans, Histoplasma capsulatum, Coccidioides immitis, Blastomyces dermatitidis, Aspergillus fumigatus, Penicillium marneffei, Bacillus anthracis, Bartonella, Bordetella pertussis, Brucella, Chlamydia trachomatis, Chlamydia pneumoniae, Clostridium botulinum, Haemophilus influenzae, Helicobacter pylori, Klebsiella, Legionella, Listeria, Mycobacterium, Mycoplasma, Rickettsia, Shigella, Staphylococcus aureus, Streptcoccus pneumoniae, S. pyogenes, Vibrio cholera, Yersinia enterocolitica*, and *Yersinia pestis*.

* * * * *